(12) United States Patent
Rockway et al.

(10) Patent No.: US 8,741,914 B2
(45) Date of Patent: Jun. 3, 2014

(54) ANTIVIRAL COMPOUNDS AND USES THEREOF

(75) Inventors: Todd W. Rockway, Gurnee, IL (US); David A. Betebenner, Grayslake, IL (US); David A. DeGoey, Salem, WI (US); Charles A. Flentge, Salem, WI (US); Douglas K. Hutchinson, Antioch, IL (US); Warren M. Kati, Gurnee, IL (US); Allan C. Krueger, Gurnee, IL (US); Dachun Liu, Vernon Hills, IL (US); Kenton L. Longenecker, Grayslake, IL (US); John K. Pratt, Kenosha, WI (US); Kent D. Stewart, Gurnee, IL (US); Rolf Wagner, Antioch, IL (US); Clarence J. Maring, Palatine, IL (US)

(73) Assignee: AbbVie Inc., North Chicago, IL (US)

( * ) Notice: Subject to any disclaimer, the term of this patent is extended or adjusted under 35 U.S.C. 154(b) by 296 days.

(21) Appl. No.: 13/260,206

(22) PCT Filed: Mar. 25, 2010

(86) PCT No.: PCT/US2010/028561
§ 371 (c)(1),
(2), (4) Date: Dec. 9, 2011

(87) PCT Pub. No.: WO2010/111437
PCT Pub. Date: Sep. 30, 2010

(65) Prior Publication Data
US 2012/0100104 A1 Apr. 26, 2012

Related U.S. Application Data

(60) Provisional application No. 61/163,157, filed on Mar. 25, 2009.

(51) Int. Cl.
*C07D 401/04* (2006.01)
*C07D 403/04* (2006.01)
*A61K 31/513* (2006.01)

(52) U.S. Cl.
USPC .................. 514/266.2; 514/266.24; 514/270; 514/274; 544/284; 544/310

(58) Field of Classification Search
USPC .......... 544/284, 310; 514/266.2, 266.24, 270, 514/274
See application file for complete search history.

(56) References Cited

U.S. PATENT DOCUMENTS 7,074,925 B1 * 7/2006 Ashkinazi ..................... 544/299

FOREIGN PATENT DOCUMENTS

WO 03062211 A1 7/2003

OTHER PUBLICATIONS

De Francesco R., et al., "Approaching a new era for Hepatitis C virus Therapy: Inhibitors of the NS3-4A Serine Protease and the NS5B RNA-Dependent RNA Polymerase," Antiviral Research, 2003, vol. 58 (1), pp. 1-16.
De Francesco R., et al., "Challenges and Successes in Developing New Therapies for Hepatitis C," Nature, 2005, vol. 436 (7053), pp. 953-960.
International Preliminary Report on Patentability and Written Opinion for Application No. PCT/US2010/028561, mailed on Sep. 27, 2011, 6 pages.
International Search Report for Application No. PCT/US2010/028561, mailed on Jul. 27, 2010, 4 pages.
Koch U., et al., "2-(2-Thienyl)-5,6-dihydroxy-4-carboxypyrimidines as Inhibitors of the Hepatitis C Virus NS5B Polymerase: Discovery, SAR, Modeling, and Mutagenesis," Journal of Medicinal Chemistry, 2006, vol. 49 (5), pp. 1693-1705.

* cited by examiner

*Primary Examiner* — Deepak Rao
(74) *Attorney, Agent, or Firm* — Bradley E. Davis

(57) ABSTRACT

This invention relates to: (a) compounds and salts thereof that, inter alia, inhibit HCV; (b) intermediates useful for the preparation of such compounds and salts; (c) compositions comprising such compounds and salts; (d) methods for preparing such intermediates, compounds, salts, and compositions; (e) methods of use of such compounds, salts, and compositions; and (f) kits comprising such compounds, salts, and compositions.

27 Claims, No Drawings

SEQUENCE LISTING

<160> NUMBER OF SEQ ID NOS: 1

<210> SEQ ID NO 1
<211> LENGTH: 171
<212> TYPE: RNA
<213> ORGANISM: Artificial Sequence
<220> FEATURE:
<223> OTHER INFORMATION: Synthetic polynucleotide

<400> SEQUENCE: 1

```
gggcgaauug ggcccucuag augcaugcuc gagcggccgc cagugugaug gauaucugca      60
gaauucgccc uugguggcuc caucuuagcc cuagucacgg cuagcuguga aagguccgug     120
agccgcuuga cugcagagag ugcugauacu ggccucucug cagaucaagu c              171
```

ANTIVIRAL COMPOUNDS AND USES THEREOF

CROSS-REFERENCE TO RELATED PATENT APPLICATIONS

This patent application claims priority to U.S. Provisional Patent Application No. 61/163,157 (filed Mar. 25, 2009). The entire text of that application is incorporated by reference into this patent application.

FIELD OF THE INVENTION

This invention is directed to: (a) compounds and salts thereof that, inter alia, are useful as hepatitis C virus (HCV) inhibitors; (b) intermediates useful for the preparation of such compounds and salts; (c) compositions comprising such compounds and salts; (d) methods for preparing such intermediates, compounds, salts, and compositions; (e) methods of use of such compounds, salts, and compositions; and (f) kits comprising such compounds, salts, and compositions.

BACKGROUND OF THE INVENTION

Hepatitis C is a blood-borne, infectious, viral disease that is caused by a hepatotropic virus called HCV. At least six different HCV genotypes (with several subtypes within each genotype) are known to date. In North America, HCV genotype 1a predominates, followed by HCV genotypes 1b, 2a, 2b, and 3a. In the United States, HCV genotypes 1, 2, and 3 are the most common, with about 80% of the hepatitis C patients having HCV genotype 1. In Europe, HCV genotype 1b is predominant, followed by HCV genotypes 2a, 2b, 2c, and 3a. HCV genotypes 4 and 5 are found almost exclusively in Africa. As discussed below, the patient's HCV genotype is clinically important in determining the patient's potential response to therapy and the required duration of such therapy.

An HCV infection can cause liver inflammation (hepatitis) that is often asymptomatic, but ensuing chronic hepatitis can result in cirrhosis of the liver (fibrotic scarring of the liver), liver cancer, and/or liver failure. The World Health Organization estimates that about 170 million persons worldwide are chronically infected with HCV, and from about three to about four million persons are newly infected globally each year. According to the Centers for Disease Control and Prevention, about four million people in the United States are infected with HCV. Co-infection with the human immunodeficiency virus (HIV) is common, and rates of HCV infection among HIV positive populations are higher.

There is a small chance of clearing the virus spontaneously, but the majority of patients with chronic hepatitis C will not clear it without treatment. Indications for treatment typically include proven HCV infection and persistent abnormal liver function tests. There are two treatment regimens that are primarily used to treat hepatitis C: monotherapy (using an interferon agent—either a "conventional" or longer-acting pegylated interferon) and combination therapy (using an interferon agent and ribavirin). Interferon, which is injected into the bloodstream, works by bolstering the immune response to HCV; and ribavirin, which is taken orally, is believed to work by preventing HCV replication. Taken alone, ribavirin does not effectively suppress HCV levels, but an interferon/ribavirin combination is more effective than interferon alone. Typically, hepatitis C is treated with a combination of pegylated interferon alpha and ribavirin for a period of 24 or 48 weeks, depending on the HCV genotype.

The goal of treatment is sustained viral response—meaning that HCV is not measurable in the blood after therapy is completed. Following treatment with a combination of pegylated interferon alpha and ribavirin, sustained cure rates (sustained viral response) of about 75% or better occur in people with HCV genotypes 2 and 3 in 24 weeks of treatment, about 50% in those with HCV genotype 1 with 48 weeks of treatment, and about 65% in those with HCV genotype 4 in 48 weeks of treatment.

Treatment may be physically demanding, particularly for those with prior history of drug or alcohol abuse, because both interferon and ribavirin have numerous side effects. Common interferon-associated side effects include flu-like symptoms, extreme fatigue, nausea, loss of appetite, thyroid problems, high blood sugar, hair loss, and skin reactions at the injection site. Possible serious interferon-associated side effects include psychoses (e.g., suicidal behavior), heart problems (e.g., heart attack, low blood pressure), other internal organ damage, blood problems (e.g., blood counts falling dangerously low), and new or worsening autoimmune disease (e.g., rheumatoid arthritis). Ribavirin-associated side effects include anemia, fatigue, irritability, skin rash, nasal stuffiness, sinusitis, and cough. Ribavirin can also cause birth defects, so pregnancy in female patients and female partners of male patients must be avoided during treatment and for six months afterward.

Some patients do not complete treatment because of the serious side effects discussed above; other patients (non-responders) continue to have measurable HCV levels despite treatment; and yet other patients (relapsers) "clear" the virus during therapy, but the virus returns sometime after completion of the treatment regimen. Thus, there continues to be a need for alternative compounds, compositions, and methods of treatment (used either in combination with or in lieu of an interferon agent and/or ribavirin) to alleviate the symptoms of hepatitis C, thereby providing partial or complete relief. This invention provides compounds (including salts thereof), compositions, and methods of treatment that generally address such a need.

SUMMARY OF THE INVENTION

This invention is directed to compounds that correspond in structure to formula (I):

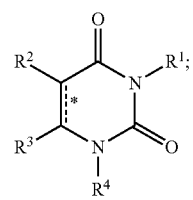

(I)

In formula (I):

⸺ is selected from the group consisting of single carbon-carbon bond and double carbon-carbon bond;

$R^1$ is selected from the group consisting of hydrogen, methyl, and nitrogen-protecting group;

$R^2$ is selected from the group consisting of hydrogen, halo, hydroxy, methyl, cyclopropyl, and cyclobutyl;

$R^3$ is selected from the group consisting of hydrogen, halo, oxo, and methyl;

$R^4$ is selected from the group consisting of

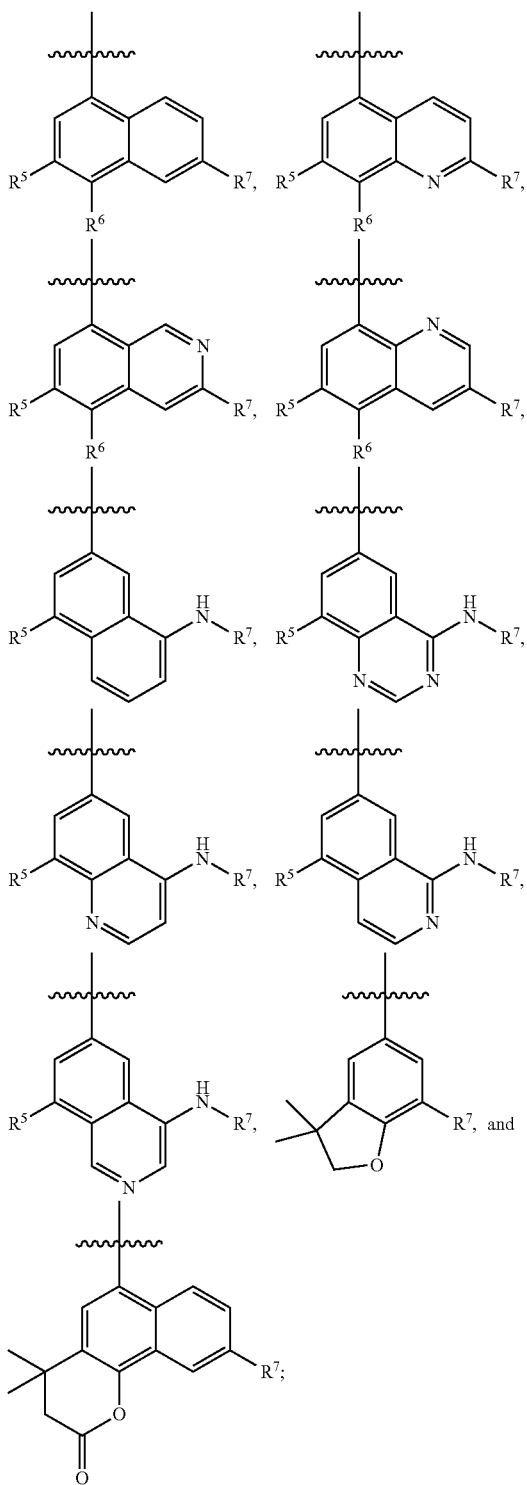

$R^5$ is selected from the group consisting of halo, alkyl, alkenyl, alkynyl, nitro, cyano, azido, alkyloxy, alkenyloxy, alkynyloxy, amino, aminocarbonyl, aminosulfonyl, alkylsulfonyl, carbocyclyl, and heterocyclyl, wherein:
 (a) the amino, aminocarbonyl, and aminosulfonyl optionally are substituted with:
  (1) one or two substituents independently selected from the group consisting of alkyl, alkenyl, alkynyl, and alkylsulfonyl, or
  (2) two substituents that, together with the amino nitrogen, form a single-ring heterocyclyl, and
 (b) the alkyl, alkenyl, alkynyl, alkyloxy, alkenyloxy, alkynyloxy, and alkylsulfonyl, optionally are substituted with one or more substituents independently selected from the group consisting of halo, oxo, nitro, cyano, azido, hydroxy, alkyl, amino, alkyloxy, carbocyclyl, and heterocyclyl, wherein:
  the amino optionally is substituted with:
   (1) one or two substituents independently selected from the group consisting of alkyl, alkenyl, alkynyl, alkylcarbonyl, alkylsulfonyl, alkyloxycarbonyl, carbocyclyl, heterocyclyl, carbocyclylalkyl, and heterocyclylalkyl, or
   (2) two substituents that, together with the amino nitrogen, form a single-ring heterocyclyl, and
 (c) the carbocyclyl and heterocyclyl optionally are substituted with up to three substituents independently selected from the group consisting of alkyl, alkenyl, alkynyl, halo, oxo, nitro, cyano, azido, hydroxy, amino, alkyloxy, trimethylsilyl, carbocyclyl, and heterocyclyl, wherein:
  the amino optionally is substituted with:
   (1) one or two substituents independently selected from the group consisting of alkyl, alkenyl, alkynyl, alkylcarbonyl, alkylsulfonyl, alkyloxycarbonyl, carbocyclyl, heterocyclyl, carbocyclylalkyl, and heterocyclylalkyl, or
   (2) two substituents that, together with the amino nitrogen, form a single-ring heterocyclyl;

$R^6$ is selected from the group consisting of hydrogen, hydroxy, alkyl, alkenyl, alkynyl, alkyloxy, alkenyloxy, alkynyloxy, alkylsulfonyloxy, amino, carbocyclylsulfonyloxy, haloalkylsulfonyloxy, and halo;

$R^7$ is selected from the group consisting of hydrogen, $C_5$-$C_6$-carbocyclyl, 5-6-membered heterocyclyl, fused 2-ring carbocyclyl, and fused 2-ring heterocyclyl, wherein:
 the $C_5$-$C_6$-carbocyclyl, 5-6-membered heterocyclyl, fused 2-ring carbocyclyl, and fused 2-ring heterocyclyl optionally are substituted with one or more substituents independently selected from the group consisting of $R^E$, $R^F$, $R^G$, $R^H$, $R^I$, $R^J$, and $R^K$;

each $R^E$ is independently selected from the group consisting of halo, nitro, hydroxy, oxo, carboxy, cyano, amino, imino, azido, and aldehydro, wherein:
 the amino optionally is substituted with one or two substituents independently selected from the group consisting of alkyl, alkenyl, and alkynyl;

each $R^F$ is independently selected from the group consisting of alkyl, alkenyl, and alkynyl, wherein:
 each such substituent optionally is substituted with one or more substituents independently selected from the group consisting of carboxy, hydroxy, halo, amino, imino, nitro, azido, oxo, aminosulfonyl, alkylsulfonyl, alkyloxycarbonyl, alkenyloxycarbonyl, alkynyloxycarbonyl, alkylcarbonyloxy, alkenylcarbonyloxy, alkynylcarbonyloxy, alkyloxy, alkenyloxy, alkynyloxy, carbocyclyl, heterocyclyl, cyano, and aminocarbonyl, wherein:
  the amino, imino, aminosulfonyl, aminocarbonyl, carbocyclyl, and heterocyclyl optionally are substituted with one or two substituents independently selected from the group consisting of alkyl, alkenyl, alkynyl, alkylsulfonyl, alkenylsulfonyl, alkynylsulfonyl, alkylsulfonylamino, hydroxy, and alkyloxy, wherein:
  amino portion of the alkylsulfonylamino optionally is substituted with a substituent selected from the group consisting of alkyl, alkenyl, and alkynyl;

each $R^G$ is independently selected from the group consisting of carbocyclyl and heterocyclyl, wherein:
  each such substituent optionally is substituted with one or more substituents independently selected from the group consisting of alkyl, alkenyl, alkynyl, carboxy, hydroxy, halo, amino, nitro, azido, oxo, aminosulfonyl, alkyloxycarbonyl, alkenyloxycarbonyl, alkynyloxycarbonyl, alkylcarbonyloxy, alkenylcarbonyloxy, alkynylcarbonyloxy, alkyloxy, alkenyloxy, alkynyloxy, carbocyclyl, heterocyclyl, cyano, and aminocarbonyl, wherein:
    the amino, aminosulfonyl, and aminocarbonyl optionally are substituted with one or two substituents independently selected from the group consisting of alkyl, alkenyl, alkynyl, alkylsulfonyl, alkenylsulfonyl, and alkynylsulfonyl;

each $R^H$ is independently selected from the group consisting of alkyloxy, alkenyloxy, alkynyloxy, alkylsulfonyloxy, alkenylsulfonyloxy, and alkynylsulfonyloxy, wherein:
  each such substituent optionally is substituted with one or more substituents independently selected from the group consisting of carboxy, hydroxy, halo, amino, nitro, azido, oxo, aminosulfonyl, alkyloxycarbonyl, alkenyloxycarbonyl, alkynyloxycarbonyl, alkylcarbonyloxy, alkenylcarbonyloxy, alkynylcarbonyloxy, alkyloxy, alkenyloxy, alkynyloxy, carbocyclyl, heterocyclyl, cyano, and aminocarbonyl, wherein:
    the amino, aminosulfonyl, and aminocarbonyl optionally are substituted with one or two substituents independently selected from the group consisting of alkyl, alkenyl, alkynyl, alkylsulfonyl, alkenylsulfonyl, and alkynylsulfonyl;

each $R^I$ is independently selected from the group consisting of alkylcarbonyl, alkenylcarbonyl, alkynylcarbonyl, aminocarbonyl, alkyloxycarbonyl, carbocyclylcarbonyl, and heterocyclylcarbonyl, wherein:
  (a) the alkylcarbonyl, alkenylcarbonyl, and alkynylcarbonyl optionally are substituted with one or more substituents independently selected from the group consisting of carboxy, hydroxy, halo, amino, nitro, azido, oxo, aminosulfonyl, alkyloxycarbonyl, alkenyloxycarbonyl, alkynyloxycarbonyl, alkylcarbonyloxy, alkenylcarbonyloxy, alkynylcarbonyloxy, alkyloxy, alkenyloxy, alkynyloxy, carbocyclyl, heterocyclyl, cyano, and aminocarbonyl, and
  (b) the aminocarbonyl optionally is substituted with one or two substituents independently selected from the group consisting of alkyl, alkenyl, alkynyl, alkyloxyalkyl, carbocyclyl, heterocyclyl, alkylsulfonyl, and alkylsulfonylamino, wherein:
    the carbocyclyl and heterocyclyl optionally are substituted with one or two substituents independently selected from the group consisting of halo, alkyl, and oxo;

each $R^J$ is independently selected from the group consisting of carbocyclylsulfonylamino, heterocyclylsulfonylamino, alkylcarbonylamino, alkenylcarbonylamino, alkynylcarbonylamino, alkyloxycarbonylamino, alkenyloxycarbonylamino, alkynyloxycarbonylamino, alkylsulfonylamino, alkenylsulfonylamino, alkynylsulfonylamino, aminocarbonylamino, alkyloxycarbonylaminoimino, alkylsulfonylaminoimino, alkenylsulfonylaminoimino, and alkynylsulfonylaminoimino, wherein:
  (a) the amino portion of such substituents optionally is substituted with a substituent independently selected from the group consisting of carbocyclylalkyl, heterocyclylalkyl, alkylcarbonyloxy, aminocarbonylalkyl, alkyl, alkenyl, alkynyl, alkylcarbonyl, alkenylcarbonyl, alkynylcarbonyl, alkyloxycarbonyl, alkyloxyalkyloxycarbonyl, alkylcarbonyloxyalkyl, and alkylsulfonyl, wherein:
    (1) the carbocyclyl portion of the carbocyclylalkyl and the heterocyclyl portion of the heterocyclylalkyl optionally are substituted with one or more substituents independently selected from the group consisting of alkyl, alkenyl, alkynyl, carboxy, hydroxy, alkyloxy, alkenyloxy, alkynyloxy, halo, nitro, cyano, azido, oxo, and amino, and
    (2) the amino portion of the aminocarbonylalkyl optionally is substituted with one or two substituents independently selected from the group consisting of alkyl, alkenyl, and alkynyl,
  (b) the alkyl, alkenyl, and alkynyl portion of such substituents optionally is substituted with one or more substituents independently selected from the group consisting of carboxy, halo, oxo, amino, alkyloxycarbonyl, alkylcarbonyloxy, hydroxy, alkyloxy, carbocyclyl, heterocyclyl, and cyano, wherein:
    the amino optionally is substituted with one or two substituents independently selected from the group consisting of alkyl, alkenyl, alkynyl, alkyloxy, alkenyloxy, and alkynyloxy, wherein:
      the alkyl optionally is substituted with one or more hydroxy;
  (c) the carbocyclyl and heterocyclyl portions of such substituents optionally are substituted with one or more substituents independently selected from the group consisting of alkyl, alkenyl, alkynyl, carboxy, hydroxy, alkyloxy, alkenyloxy, alkynyloxy, halo, nitro, cyano, azido, and amino, wherein:
    the amino optionally is substituted with one or two substituents independently selected from the group consisting of alkyl, alkenyl, and alkynyl; and each $R^K$ is independently selected from the group consisting of aminosulfonyl, alkylsulfonyl, alkenylsulfonyl, and alkynylsulfonyl, wherein:
  (a) the alkylsulfonyl, alkenylsulfonyl, and alkynylsulfonyl optionally are substituted with one or more substituents independently selected from the group consisting of carboxy, hydroxy, halo, amino, nitro, azido, oxo, aminosulfonyl, alkyloxycarbonyl, alkenyloxycarbonyl, alkynyloxycarbonyl, alkylcarbonyloxy, alkenylcarbonyloxy, alkynylcarbonyloxy, alkyloxy, alkenyloxy, alkynyloxy, carbocyclyl, heterocyclyl, cyano, and aminocarbonyl, wherein:
    the amino, aminosulfonyl, and aminocarbonyl optionally are substituted with one or two substituents independently selected from the group consisting of alkyl, alkenyl, and alkynyl; and
  (b) the aminosulfonyl optionally is substituted with one or two substituents independently selected from the group consisting of alkyl, alkenyl, and alkynyl.

This invention also is directed to the salts (including pharmaceutically acceptable salts) of the compounds of the invention.

This invention also is directed to compositions (including pharmaceutical compositions) that comprise one or more compounds and/or salts of the invention, and, optionally, one or more additional therapeutic agents.

This invention also is directed to kits that comprise one or more compounds and/or salts of the invention, and, optionally, one or more additional therapeutic agents.

This invention also is directed to methods of use of the compounds, salts, compositions, and/or kits of the invention to, for example, inhibit replication of an RNA virus (including HCV), treat a disease treatable by inhibiting HCV ribonucleic acid (RNA) polymerase (including hepatitis C).

This invention also is directed to a use of one or more compounds and/or salts of the invention to prepare a medicament. The medicament optionally can comprise one or more additional therapeutic agents. In some embodiments, the medicament is useful for treating hepatitis C.

Further benefits of Applicants' invention will be apparent to one skilled in the art from reading this patent application.

DETAILED DESCRIPTION OF THE INVENTION

This detailed description is intended only to acquaint others skilled in the art with Applicants' invention, its principles, and its practical application so that others skilled in the art may adapt and apply the invention in its numerous forms, as they may be best suited to the requirements of a particular use. This description and its specific examples are intended for purposes of illustration only. This invention, therefore, is not limited to the embodiments described in this patent application, and may be variously modified.

A. Definitions

The term "alkyl" (alone or in combination with another term(s)) means a straight- or branched-chain saturated hydrocarbyl substituent typically containing from 1 to about 20 carbon atoms, more typically from 1 to about 8 carbon atoms, and even more typically from 1 to about 6 carbon atoms. Examples of such substituents include methyl, ethyl, n-propyl, isopropyl, n-butyl, isobutyl, sec-butyl, tert-butyl, pentyl, iso-amyl, and hexyl. As in this definition, throughout this detailed description Applicants have provided illustrative examples. The provision of such illustrative examples should not be interpreted as if the provided illustrative examples are the only options available to one skilled in the art.

The term "alkenyl" (alone or in combination with another term(s)) means a straight- or branched-chain hydrocarbyl substituent containing one or more double bonds and typically from 2 to about 20 carbon atoms, more typically from about 2 to about 8 carbon atoms, and even more typically from about 2 to about 6 carbon atoms. Examples of such substituents include ethenyl (vinyl), 2-propenyl, 3-propenyl, 1,4-pentadienyl, 1,4-butadienyl, 1-butenyl, 2-butenyl, and 3-butenyl.

The term "alkynyl" (alone or in combination with another term(s)) means a straight- or branched-chain hydrocarbyl substituent containing one or more triple bonds and typically from 2 to about 20 carbon atoms, more typically from about 2 to about 8 carbon atoms, and even more typically from about 2 to about 6 carbon atoms. Examples of such substituents include ethynyl, 2-propynyl, 3-propynyl, 2-butynyl, and 3-butynyl.

The term "carbocyclyl" (alone or in combination with another term(s)) means a saturated cyclic (i.e., "cycloalkyl"), partially saturated cyclic (i.e., "cycloalkenyl"), or completely unsaturated (i.e., "aryl") hydrocarbyl substituent containing from 3 to 14 carbon ring atoms ("ring atoms" are the atoms bound together to form the ring or rings of a cyclic substituent). A carbocyclyl may be a single ring, which typically contains from 3 to 6 ring atoms. Examples of such single-ring carbocyclyls include cyclopropyl (cyclopropanyl), cyclobutyl (cyclobutanyl), cyclopentyl (cyclopentanyl), cyclopentenyl, cyclopentadienyl, cyclohexyl (cyclohexanyl), cyclohexenyl, cyclohexadienyl, and phenyl. A carbocyclyl alternatively may be 2 or 3 rings fused together, such as naphthalenyl, tetrahydronaphthalenyl (tetralinyl), indenyl, indenyl (dihydroindenyl), anthracenyl, phenanthrenyl, and decalinyl.

The term "cycloalkyl" (alone or in combination with another term(s)) means a saturated cyclic hydrocarbyl substituent containing from 3 to 14 carbon ring atoms. A cycloalkyl may be a single carbon ring, which typically contains from 3 to 6 carbon ring atoms. Examples of single-ring cycloalkyls include cyclopropyl, cyclobutyl, cyclopentyl, and cyclohexyl. A cycloalkyl alternatively may be 2 or 3 carbon rings fused together, such as, decalinyl.

The term "aryl" (alone or in combination with another term(s)) means an aromatic carbocyclyl containing from 6 to 14 carbon ring atoms. Examples of aryls include phenyl, naphthalenyl, and indenyl.

In some instances, the number of carbon atoms in a hydrocarbyl substituent (e.g., alkyl, alkenyl, alkynyl, or cycloalkyl) is indicated by the prefix "$C_x$-$C_y$-", wherein x is the minimum and y is the maximum number of carbon atoms in the substituent. Thus, for example, "$C_1$-$C_6$-alkyl" refers to an alkyl substituent containing from 1 to 6 carbon atoms. Illustrating further, $C_3$-$C_6$-cycloalkyl means a saturated hydrocarbyl ring containing from 3 to 6 carbon ring atoms.

The term "hydrogen" (alone or in combination with another term(s)) means a hydrogen radical, and may be depicted as —H.

The term "hydroxy" (alone or in combination with another term(s)) means —OH.

The term "nitro" (alone or in combination with another term(s)) means —$NO_2$.

The term "cyano" (alone or in combination with another term(s)) means —CN, which also may be depicted as —C≡N.

The term "keto" (alone or in combination with another term(s)) means an oxo radical, and may be depicted as =O.

The term "carboxy" (alone or in combination with another term(s)) means —C(O)—OH.

The term "amino" (alone or in combination with another term(s)) means —$NH_2$.

The term "amino" (alone or in combination with another term(s)) means =NH.

The term "aminoimino" (alone or in combination with another term(s)) means =$NNH_2$.

The term "halogen" or "halo" (alone or in combination with another term(s)) means a fluorine radical (which may be depicted as —F), chlorine radical (which may be depicted as —Cl), bromine radical (which may be depicted as —Br), or iodine radical (which may be depicted as —I).

A substituent is "substitutable" if it comprises at least one carbon or nitrogen atom that is bonded to one or more hydrogen atoms. Thus, for example, hydrogen, halogen, and cyano do not fall within this definition. In addition, a sulfur atom in a heterocyclyl containing such atom is substitutable with one or two oxo substituents.

If a substituent is described as being "substituted", a non-hydrogen radical is in the place of hydrogen radical on a carbon or nitrogen of the substituent. Thus, for example, a substituted alkyl substituent is an alkyl substituent in which at least one non-hydrogen radical is in the place of a hydrogen radical on the alkyl substituent. To illustrate, monofluoroalkyl is alkyl substituted with a fluoro radical, and difluoroalkyl is alkyl substituted with two fluoro radicals. It should be recognized that if there are more than one substitution on a substituent, each non-hydrogen radical may be identical or different (unless otherwise stated).

If a substituent is described as being "optionally substituted", the substituent may be either (1) not substituted or (2) substituted. If a substituent is described as being optionally substituted with up to a particular number of non-hydrogen radicals, that substituent may be either (1) not substituted; or (2) substituted by up to that particular number of non-hydrogen radicals or by up to the maximum number of substitutable positions on the substituent, whichever is less. Thus, for example, if a substituent is described as a heteroaryl optionally substituted with up to 3 non-hydrogen radicals, then any heteroaryl with less than 3 substitutable positions would be optionally substituted by up to only as many non-hydrogen radicals as the heteroaryl has substitutable positions. To illustrate, tetrazolyl (which has only one substitutable position) would be optionally substituted with up to one non-hydrogen radical. To illustrate further, if an amino nitrogen is described as being optionally substituted with up to 2 non-hydrogen radicals, then a primary amino nitrogen will be optionally substituted with up to 2 non-hydrogen radicals, whereas a secondary amino nitrogen will be optionally substituted with up to only 1 non-hydrogen radical.

This patent application uses the terms "substituent" and "radical" interchangeably.

The prefix "halo" indicates that the substituent to which the prefix is attached is substituted with one or more independently selected halogen radicals. For example, haloalkyl means an alkyl substituent in which at least one hydrogen radical is replaced with a halogen radical. Examples of haloalkyls include chloromethyl, 1-bromoethyl, fluoromethyl, difluoromethyl, trifluoromethyl, and 1,1,1-trifluoroethyl. It should be recognized that if a substituent is substituted by more than one halogen radical, those halogen radicals may be identical or different (unless otherwise stated).

The prefix "perhalo" indicates that every hydrogen radical on the substituent to which the prefix is attached is replaced with independently selected halogen radicals, i.e., each hydrogen radical on the substituent is replaced with a halogen radical. If all the halogen radicals are identical, the prefix typically will identify the halogen radical. Thus, for example, the term "perfluoro" means that every hydrogen radical on the substituent to which the prefix is attached is substituted with a fluorine radical. To illustrate, the term "perfluoroalkyl" means an alkyl substituent wherein a fluorine radical is in the place of each hydrogen radical.

The term "carbonyl" (alone or in combination with another term(s)) means —C(O)—.

The term "aminocarbonyl" (alone or in combination with another term(s)) means —C(O)—NH$_2$.

The term "oxy" (alone or in combination with another term(s)) means an ether substituent, and may be depicted as —O—.

The term "alkyloxy" or "alkoxy" (alone or in combination with another term(s)) means an alkylether substituent, i.e., —O-alkyl. Examples of such a substituent include methoxy (—O—CH$_3$), ethoxy, n-propoxy, isopropoxy, n-butoxy, iso-butoxy, sec-butoxy, and tert-butoxy.

The term "alkylcarbonyl" (alone or in combination with another term(s)) means —C(O)-alkyl.

The term "aminoalkylcarbonyl" (alone or in combination with another term(s)) means C(O)-alkyl-NH$_2$.

The term "alkyloxycarbonyl" (alone or in combination with another term(s)) means —C(O)—O-alkyl.

The term "carbocyclylcarbonyl" (alone or in combination with another term(s)) means —C(O)-carbocyclyl.

Similarly, the term "heterocyclylcarbonyl" (alone or in combination with another term(s)) means —C(O)-heterocyclyl.

The term "carbocyclylalkylcarbonyl" (alone or in combination with another term(s)) means —C(O)-alkyl-carbocyclyl.

Similarly, the term "heterocyclylalkylcarbonyl" (alone or in combination with another term(s)) means —C(O)-alkyl-heterocyclyl.

The term "carbocyclyloxycarbonyl" (alone or in combination with another term(s)) means —C(O)—O-carbocyclyl.

The term "carbocyclylalkyloxycarbonyl" (alone or in combination with another term(s)) means —C(O)—O-alkyl-carbocyclyl.

The term "thio" or "this" (alone or in combination with another term(s)) means a thiaether substituent, i.e., an ether substituent wherein a divalent sulfur atom is in the place of the ether oxygen atom. Such a substituent may be depicted as —S—. This, for example, "alkyl-thio-alkyl" means alkyl-5-alkyl (alkyl-sulfanyl-alkyl).

The term "thiol" or "sulfhydryl" (alone or in combination with another term(s)) means a sulfhydryl substituent, and may be depicted as —SH.

The term "(thiocarbonyl)" (alone or in combination with another term(s)) means a carbonyl wherein the oxygen atom has been replaced with a sulfur. Such a substituent may be depicted as —C(S)—.

The term "sulfonyl" (alone or in combination with another term(s)) means —S(O)$_2$—.

The term "aminosulfonyl" (alone or in combination with another term(s)) means —S(O)$_2$—NH$_2$.

The term "sulfinyl" or "sulfoxido" (alone or in combination with another term(s)) means —S(O)—.

The term "heterocyclyl" (alone or in combination with another term(s)) means a saturated (i.e., "heterocycloalkyl"), partially saturated (i.e., "heterocycloalkenyl"), or completely unsaturated (i.e., "heteroaryl") ring structure containing a total of 3 to 14 ring atoms. At least one of the ring atoms is a heteroatom (i.e., oxygen, nitrogen, or sulfur), with the remaining ring atoms being independently selected from the group consisting of carbon, oxygen, nitrogen, and sulfur.

A heterocyclyl may be a single ring, which typically contains from 3 to 7 ring atoms, more typically from 3 to 6 ring atoms, and even more typically 5 to 6 ring atoms. Examples of single-ring heterocyclyls include furanyl, dihydrofuranyl, tetrahydrofuranyl, thiophenyl (thiofuranyl), dihydrothiophenyl, tetrahydrothiophenyl, pyrrolyl, pyrrolinyl, pyrrolidinyl, imidazolyl, imidazolinyl, imidazolidinyl, pyrazolyl, pyrazolinyl, pyrazolidinyl, triazolyl, tetrazolyl, oxazolyl, oxazolidinyl, isoxazolidinyl, isoxazolyl, thiazolyl, isothiazolyl, thiazolinyl, isothiazolinyl, thiazolidinyl, isothiazolidinyl, thiodiazolyl, oxadiazolyl (including 1,2,3-oxadiazolyl, 1,2,4-oxadiazolyl, 1,2,5-oxadiazolyl (furazanyl), or 1,3,4-oxadiazolyl), oxatriazolyl (including 1,2,3,4-oxatriazolyl or 1,2,3,5-oxatriazolyl), dioxazolyl (including 1,2,3-dioxazolyl, 1,2,4-dioxazolyl, 1,3,2-dioxazolyl, or 1,3,4-dioxazolyl), oxathiazolyl, oxathiolyl, oxathiolanyl, pyranyl, dihydropyranyl, thiopyranyl, tetrahydrothiopyranyl, pyridinyl (azinyl), piperidinyl, diazinyl (including pyridazinyl (1,2-diazinyl), pyrimidinyl (1,3-diazinyl), or pyrazinyl (1,4-diazinyl)), piperazinyl, triazinyl (including 1,3,5-triazinyl, 1,2,4-triazinyl, and 1,2,3-triazinyl)), oxazinyl (including 1,2-oxazinyl, 1,3-oxazinyl, or 1,4-oxazinyl)), oxathiazinyl (including 1,2,3-oxathiazinyl, 1,2,4-oxathiazinyl, 1,2,5-oxathiazinyl, or 1,2,6-oxathiazinyl)), oxadiazinyl (including 1,2,3-oxadiazinyl, 1,2, 4-oxadiazinyl, 1,4,2-oxadiazinyl, or 1,3,5-oxadiazinyl)), morpholinyl, azepinyl, oxepinyl, thiepinyl, and diazepinyl.

A heterocyclyl alternatively may be 2 or 3 rings fused together, such as, for example, indolizinyl, pyranopyrrolyl, 4H-quinolizinyl, purinyl, naphthyridinyl, pyridopyridinyl (including pyrido[3,4-b]-pyridinyl, pyrido[3,2-b]-pyridinyl, or pyrido[4,3-b]-pyridinyl), and pteridinyl. Other examples of fused-ring heterocyclyls include benzo-fused heterocyclyls, such as indolyl, isoindolyl (isobenzazolyl, pseudoisoindolyl), indoleninyl (pseudoindolyl), isoindazolyl (benzpyrazolyl), benzazinyl (including quinolinyl (1-benzazinyl) or isoquinolinyl (2-benzazinyl)), phthalazinyl, quinoxalinyl, quinazolinyl, benzodiazinyl (including cinnolinyl (1,2-benzodiazinyl) or quinazolinyl (1,3-benzodiazinyl)), benzopyranyl (including chromanyl or isochromanyl), benzoxazinyl (including 1,3,2-benzoxazinyl, 1,4,2-benzoxazinyl, 2,3,1-benzoxazinyl, or 3,1,4-benzoxazinyl), and benzisoxazinyl (including 1,2-benzisoxazinyl or 1,4-benzisoxazinyl).

The term "2-fused ring" heterocyclyl (alone or in combination with another term(s)) means a saturated, partially saturated, or aryl heterocyclyl containing 2 fused rings. Examples of 2-fused-ring heterocyclyls include indolizinyl, quinolizinyl, purinyl, naphthyridinyl, pteridinyl, indolyl, isoindolyl, indoleninyl, isoindazolyl, phthalazinyl, quinoxalinyl, quinazolinyl, benzodiazinyl, benzopyranyl, benzothiopyranyl, benzoxazolyl, anthranilyl, benzodioxolyl, benzodioxanyl, benzoxadiazolyl, benzofuranyl, isobenzofuranyl, benzothiazolyl, benzothiadiazolyl, benzimidazolyl, benzotriazolyl, benzoxazinyl, and tetrahydroisoquinolinyl.

The term "heteroaryl" (alone or in combination with another term(s)) means an aromatic heterocyclyl containing from 5 to 14 ring atoms. A heteroaryl may be a single ring or 2 or 3 fused rings. Examples of heteroaryl substituents include 6-membered ring substituents such as pyridyl, pyrazyl, pyrimidinyl, pyridazinyl, and 1,3,5-, 1,2,4- or 1,2,3-triazinyl; 5-membered ring substituents such as imidazyl, furanyl, thiophenyl, pyrazolyl, oxazolyl, isoxazolyl, thiazolyl, 1,2,3-, 1,2,4-, 1,2,5-, or 1,3,4-oxadiazolyl and isothiazolyl; 6/5-membered fused ring substituents such as benzothiofuranyl, benzisoxazolyl, benzoxazolyl, purinyl, and anthranilyl; and 6/6-membered fused rings such as benzopyranyl, quinolinyl, isoquinolinyl, cinnolinyl, quinazolinyl, and benzoxazinyl.

A prefix attached to a multi-component substituent only applies to the first component. To illustrate, the term "alkylcycloalkyl" contains two components: alkyl and cycloalkyl. Thus, the $C_1$-$C_6$-prefix on $C_1$-$C_6$-alkylcycloalkyl means that the alkyl component of the alkylcycloalkyl contains from 1 to 6 carbon atoms; the $C_1$-$C_6$-prefix does not describe the cycloalkyl component. To illustrate further, the prefix "halo" on haloalkoxyalkyl indicates that only the alkoxy component of the alkoxyalkyl substituent is substituted with one or more halogen radicals. If halogen substitution may alternatively or additionally occur on the alkyl component, the substituent would instead be described as "halogen-substituted alkoxyalkyl" rather than "haloalkoxyalkyl." And finally, if the halogen substitution may only occur on the alkyl component, the substituent would instead be described as "alkoxyhaloalkyl."

If substituents are described as being "independently selected" from a group, each substituent is selected independent of the other. Each substituent therefore may be identical to or different from the other substituent(s).

When words are used to describe a substituent, the rightmost-described component of the substituent is the component that has the free valence.

When a chemical formula is used to describe a substituent, the dash on the left side of the formula indicates the portion of the substituent that has the free valence.

When a chemical formula is used to describe a linking element between two other elements of a depicted chemical structure, the leftmost dash of the substituent indicates the portion of the substituent that is bound to the left element in the depicted structure. The rightmost dash, on the other hand, indicates the portion of the substituent that is bound to the right element in the depicted structure. To illustrate, if the depicted chemical structure is X-L-Y and L is described as —C(O)—NH—, then the chemical would be X—C(O)—NH—Y.

With reference to the use of the words "comprise" or "comprises" or "comprising" in this patent application (including the claims), Applicants note that unless the context requires otherwise, those words are used on the basis and clear understanding that they are to be interpreted inclusively, rather than exclusively, and that Applicants intend each of those words to be so interpreted in construing this patent application, including the claims below.

ChemDraw software has been used to generate the compound names in this patent application.

The term "purity", unless otherwise qualified, means the chemical purity of a compound according to conventional HPLC assay.

B. Compounds

As discussed above, this invention is directed, in part, to compounds that correspond in structure to formula (I):

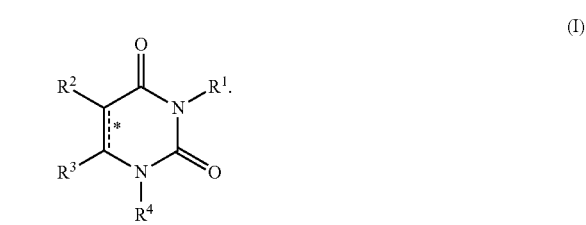

(I)

In these compounds, ═ is selected from the group consisting of single carbon-carbon bond and double carbon-carbon bond.

In some embodiments, ═ is a single carbon-carbon bond. In these embodiments, the compounds of formula (I) correspond in structure to the following formula (i.e., formula IA):

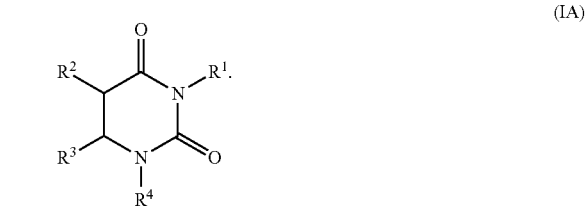

(IA)

In other embodiments, ═ is a double carbon-carbon bond. In these embodiments, the compounds of formula (I) correspond in structure to the following formula (i.e., formula IB):

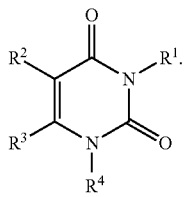

(IB)

B1. Substituent $R^1$ $R^1$ is selected from the group consisting of hydrogen, methyl, and nitrogen-protecting group.

In some embodiments, $R^1$ is hydrogen.

In some embodiments, $R^1$ is methyl.

In some embodiments, $R^1$ is selected from the group consisting of hydrogen and methyl.

In some embodiments, $R^1$ is a nitrogen-protecting group. In these embodiments, the compounds are useful as intermediates for the preparation of compounds of formula (I). Nitrogen-protecting groups suitable for preparing compounds of formula (I) are known to those skilled in the art.

B2. Substituent $R^2$ $R^2$ is selected from the group consisting of hydrogen, halo, hydroxy, methyl, cyclopropyl, and cyclobutyl.

In some embodiments, $R^2$ is hydrogen.

In some embodiments, $R^2$ is halo. In some such embodiments, $R^2$ is selected from the group consisting of fluoro and chloro. In other such embodiments, $R^2$ is fluoro. In yet other such embodiments, $R^2$ is chloro. In yet other such embodiments, $R^2$ is bromo. In further such embodiments, $R^2$ is iodo.

In some embodiments, $R^2$ is hydroxy.

In some embodiments, $R^2$ is methyl.

In some embodiments, $R^2$ is cyclopropyl.

In some embodiments, $R^2$ is cyclobutyl.

In some embodiments, $R^2$ is selected from the group consisting of hydrogen, methyl, hydroxy, and halo. In some such embodiments, $R^2$ is selected from the group consisting of hydrogen, methyl, hydroxy, fluoro, and chloro. In other such embodiments, $R^2$ is selected from the group consisting of hydrogen, methyl, hydroxy, and fluoro. In yet other such embodiments, $R^2$ is selected from the group consisting of hydrogen, methyl, hydroxy, and chloro. In yet other such embodiments, $R^2$ is selected from the group consisting of hydrogen, methyl, hydroxy, and bromo. In further such embodiments, $R^2$ is selected from the group consisting of hydrogen, methyl, hydroxy, and iodo.

In some embodiments, $R^2$ is selected from the group consisting of hydrogen, methyl, and halo. In some such embodiments, $R^2$ is selected from the group consisting of hydrogen, methyl, fluoro, and chloro. In other such embodiments, $R^2$ is selected from the group consisting of hydrogen, methyl, and fluoro. In yet other such embodiments, $R^2$ is selected from the group consisting of hydrogen, methyl, and chloro. In yet other such embodiments, $R^2$ is selected from the group consisting of hydrogen, methyl, and bromo. In further such embodiments, $R^2$ is selected from the group consisting of hydrogen, methyl, and iodo.

In some embodiments, $R^2$ is selected from the group consisting of hydrogen and halo. In some such embodiments, $R^2$ is selected from the group consisting of hydrogen, fluoro, and chloro. In other such embodiments, $R^2$ is selected from the group consisting of hydrogen and fluoro. In yet other such embodiments, $R^2$ is selected from the group consisting of hydrogen and chloro. In yet other such embodiments, $R^2$ is selected from the group consisting of hydrogen and bromo. In further such embodiments, $R^2$ is selected from the group consisting of hydrogen and iodo.

B3. Substituent $R^3$ $R^3$ is selected from the group consisting of hydrogen, halo, oxo, and methyl. In some such embodiments, $R^3$ is selected from the group consisting of hydrogen, fluoro, oxo, and methyl. In other such embodiments, $R^3$ is selected from the group consisting of hydrogen, chloro, oxo, and methyl. In yet other such embodiments, $R^3$ is selected from the group consisting of hydrogen, bromo, oxo, and methyl. In yet other such embodiments, $R^3$ is selected from the group consisting of hydrogen, iodo, oxo, and methyl.

In some embodiments, $R^3$ is selected from the group consisting of hydrogen, halo, and oxo. In some such embodiments, $R^3$ is selected from the group consisting of hydrogen, fluoro, and oxo. In other such embodiments, $R^3$ is selected from the group consisting of hydrogen, chloro, and oxo. In yet other such embodiments, $R^3$ is selected from the group consisting of hydrogen, bromo, and oxo. In yet other such embodiments, $R^3$ is selected from the group consisting of hydrogen, iodo, and oxo.

In some embodiments, $R^3$ is selected from the group consisting of hydrogen and methyl.

In some embodiments, $R^3$ is hydrogen.

In some embodiments, $R^3$ is methyl.

In some embodiments, $R^3$ is oxo.

In some embodiments, $R^3$ is halo. In some such embodiments, $R^3$ is fluoro. In other such embodiments, $R^3$ is chloro. In yet other such embodiments, $R^3$ is bromo. In further such embodiments, $R^3$ is iodo.

B4. Substituent $R^4$ $R^4$ is selected from the group consisting of:

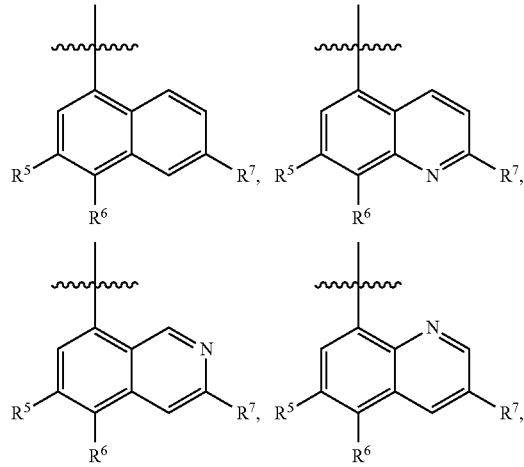

-continued
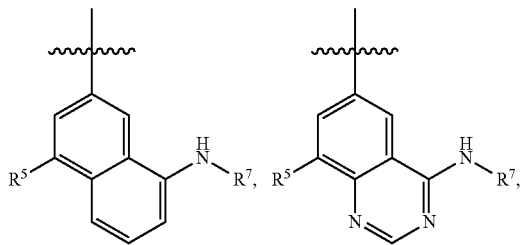
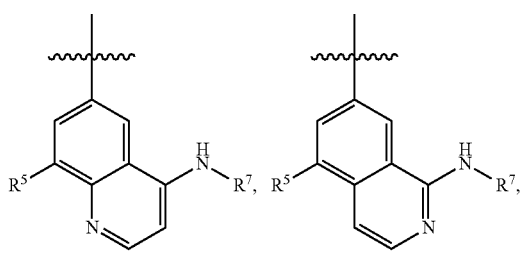
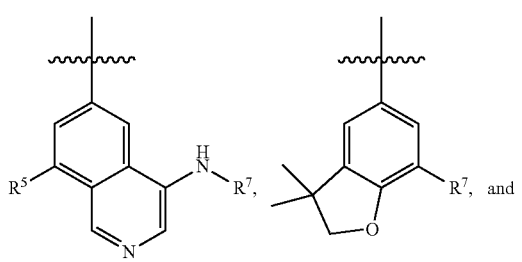
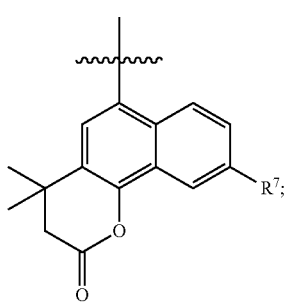
In some embodiments, R⁴ is
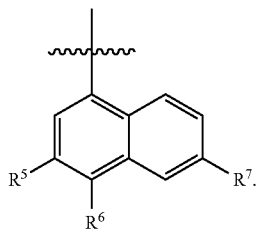
In these embodiments, the compounds of formula (I) correspond in structure to formula (I-1):
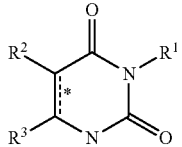
(I-1)
In some embodiments, R⁴ is
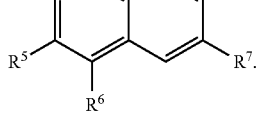
In these embodiments, the compounds of formula (I) correspond in structure to formula (I-2):
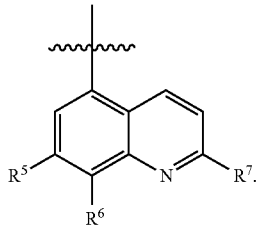
(I-2)
In some embodiments, R⁴ is
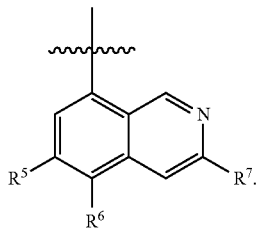

In these embodiments, the compounds of formula (I) correspond in structure to formula (I-3):

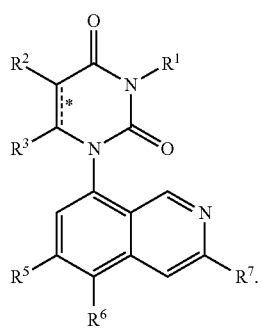
(I-3)

In some embodiments, $R^4$ is

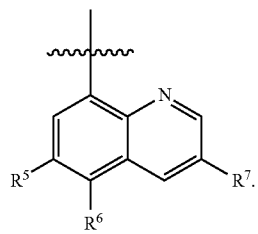

In these embodiments, the compounds of formula (I) correspond in structure to formula (I-4):

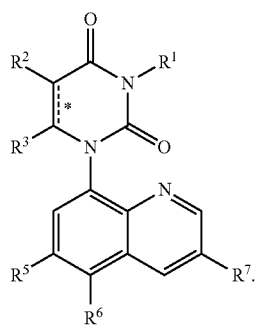
(I-4)

In some embodiments, $R^4$ is

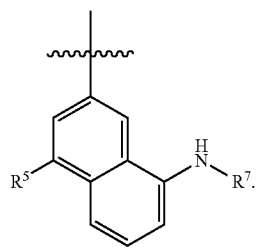

In these embodiments, the compounds of formula (I) correspond in structure to formula (I-5):

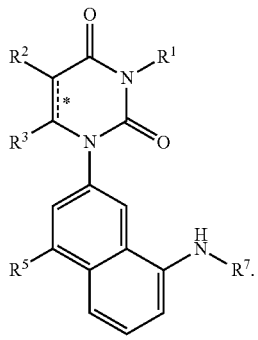
(I-5)

In some embodiments, $R^4$ is

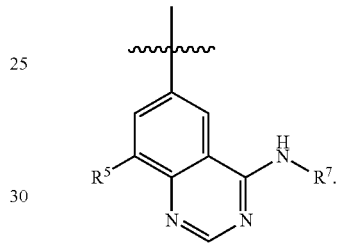

In these embodiments, the compounds of formula (I) correspond in structure to formula (I-6):

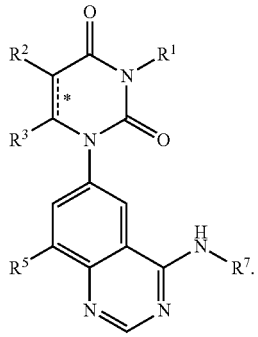
(I-6)

In some embodiments, $R^4$ is

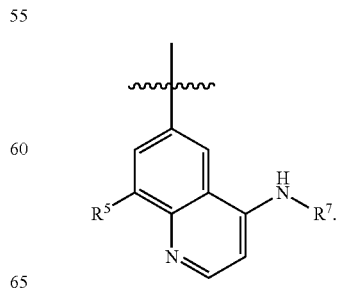

In these embodiments, the compounds of formula (I) correspond in structure to formula (I-7):

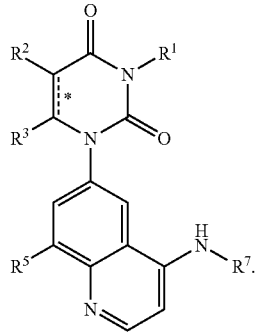
(I-7)

In some embodiments, $R^4$ is

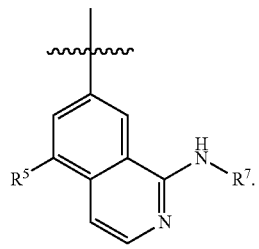

In these embodiments, the compounds of formula (I) correspond in structure to formula (I-8):

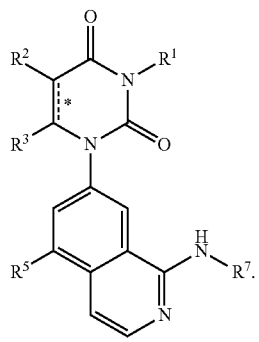
(I-8)

In some embodiments, $R^4$ is

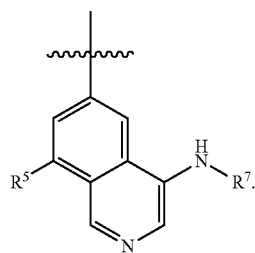

In these embodiments, the compounds of formula (I) correspond in structure to formula (I-9):

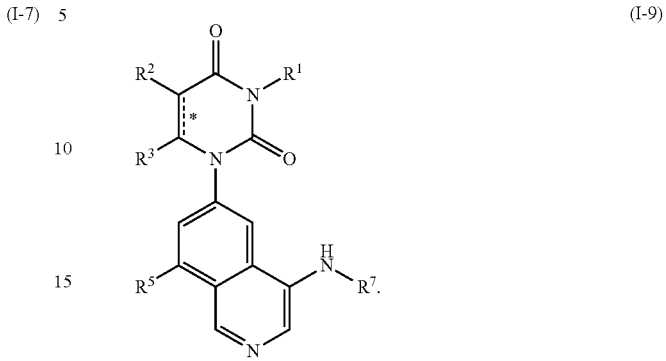
(I-9)

In some embodiments, $R^4$ is

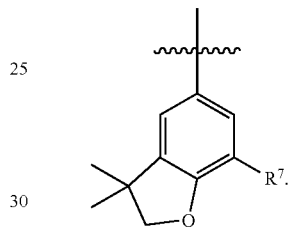

In these embodiments, the compounds of formula (I) correspond in structure to formula (I-10):

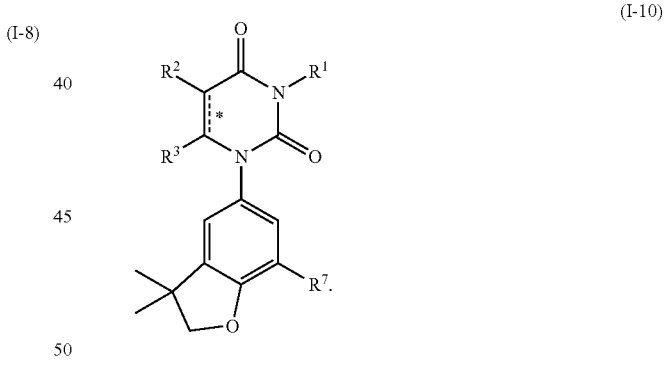
(I-10)

In some embodiments, $R^4$ is

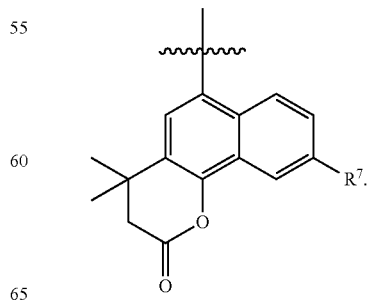

In these embodiments, the compounds of formula (I) correspond in structure to formula (I-11):

(I-11)

In some of the above embodiments, ⚌ is a single carbon-carbon bond. In other of the above embodiments, ⚌ is a double carbon-carbon bond.

B5. Substituent $R^5$ $R^5$ is selected from the group consisting of halo, alkyl, alkenyl, alkynyl, nitro, cyano, azido, alkyloxy, alkenyloxy, alkynyloxy, amino, aminocarbonyl, aminosulfonyl, alkylsulfonyl, carbocyclyl, and heterocyclyl, wherein:
- (a) the amino, aminocarbonyl, and aminosulfonyl optionally are substituted with:
    - (1) one or two substituents independently selected from the group consisting of alkyl, alkenyl, alkynyl, and alkylsulfonyl, or
    - (2) two substituents that, together with the amino nitrogen, form a single-ring heterocyclyl,
- (b) the alkyl, alkenyl, alkynyl, alkyloxy, alkenyloxy, alkynyloxy, and alkylsulfonyl, optionally are substituted with one or more substituents independently selected from the group consisting of halo, oxo, nitro, cyano, azido, hydroxy, amino, alkyloxy, trimethylsilyl, carbocyclyl, and heterocyclyl, wherein:
    the amino optionally is substituted with:
    - (1) one or two substituents independently selected from the group consisting of alkyl, alkenyl, alkynyl, alkylcarbonyl, alkylsulfonyl, alkyloxycarbonyl, carbocyclyl, heterocyclyl, carbocyclylalkyl, and heterocyclylalkyl, or
    - (2) two substituents that, together with the amino nitrogen, form a single-ring heterocyclyl, and
- (c) the carbocyclyl and heterocyclyl optionally are substituted with up to three substituents independently selected from the group consisting of alkyl, alkenyl, alkynyl, halo, oxo, nitro, cyano, azido, hydroxy, amino, alkyloxy, trimethylsilyl, carbocyclyl, and heterocyclyl, wherein:
    the amino optionally is substituted with:
    - (1) one or two substituents independently selected from the group consisting of alkyl, alkenyl, alkynyl, alkylcarbonyl, alkylsulfonyl, alkyloxycarbonyl, carbocyclyl, heterocyclyl, carbocyclylalkyl, and heterocyclylalkyl, or
    - (2) two substituents that, together with the amino nitrogen, form a single-ring heterocyclyl.

In some embodiments, $R^5$ is selected from the group consisting of halo, alkyl, alkenyl, alkynyl, nitro, cyano, azido, alkyloxy, alkenyloxy, alkynyloxy, amino, aminocarbonyl, aminosulfonyl, alkylsulfonyl, carbocyclyl, and heterocyclyl, wherein:
the amino, aminocarbonyl, and aminosulfonyl optionally are substituted with:
- (1) one or two substituents independently selected from the group consisting of alkyl, alkenyl, alkynyl, and alkylsulfonyl, or
- (2) two substituents that, together with the amino nitrogen, form a single-ring heterocyclyl.

In some embodiments, $R^5$ is selected from the group consisting of halo, alkyl, alkenyl, alkynyl, nitro, cyano, azido, alkyloxy, alkenyloxy, alkynyloxy, amino, aminocarbonyl, aminosulfonyl, alkylsulfonyl, carbocyclyl, and heterocyclyl, wherein:
the alkyl, alkenyl, alkynyl, alkyloxy, alkenyloxy, alkynyloxy, and alkylsulfonyl, optionally are substituted with one or more substituents independently selected from the group consisting of halo, oxo, nitro, cyano, azido, hydroxy, amino, alkyloxy, trimethylsilyl, carbocyclyl, and heterocyclyl, wherein:
the amino optionally is substituted with:
- (1) one or two substituents independently selected from the group consisting of alkyl, alkenyl, alkynyl, alkylcarbonyl, alkylsulfonyl, alkyloxycarbonyl, carbocyclyl, heterocyclyl, carbocyclylalkyl, and heterocyclylalkyl, or
- (2) two substituents that, together with the amino nitrogen, form a single-ring heterocyclyl.

In some embodiments, $R^5$ is selected from the group consisting of halo, alkyl, alkenyl, alkynyl, nitro, cyano, azido, alkyloxy, alkenyloxy, alkynyloxy, amino, aminocarbonyl, aminosulfonyl, alkylsulfonyl, carbocyclyl, and heterocyclyl, wherein:
the carbocyclyl and heterocyclyl optionally are substituted with up to three substituents independently selected from the group consisting of alkyl, alkenyl, alkynyl, halo, oxo, nitro, cyano, azido, hydroxy, amino, alkyloxy, trimethylsilyl, carbocyclyl, and heterocyclyl, wherein:
the amino optionally is substituted with:
- (1) one or two substituents independently selected from the group consisting of alkyl, alkenyl, alkynyl, alkylcarbonyl, alkylsulfonyl, alkyloxycarbonyl, carbocyclyl, heterocyclyl, carbocyclylalkyl, and heterocyclylalkyl, or
- (2) two substituents that, together with the amino nitrogen, form a single-ring heterocyclyl.

In some embodiments, $R^5$ is selected from the group consisting of halo, alkyl, alkenyl, alkynyl, nitro, cyano, azido, alkyloxy, alkenyloxy, alkynyloxy, amino, aminocarbonyl, aminosulfonyl, alkylsulfonyl, carbocyclyl, and heterocyclyl, wherein:
- (a) the amino, aminocarbonyl, and aminosulfonyl optionally are substituted with:
    - (1) one or two substituents independently selected from the group consisting of alkyl, alkenyl, and alkynyl, or,
    - (2) two substituents that, together with the amino nitrogen, form a single-ring heterocyclyl; and
- (b) the alkyl, alkenyl, alkynyl, alkyloxy, alkenyloxy, alkynyloxy, alkylsulfonyl, carbocyclyl, and heterocyclyl optionally are substituted with up to three substituents independently selected from the group consisting of halo, oxo, nitro, cyano, azido, hydroxy, amino, alkyloxy, carbocyclyl, and heterocyclyl, wherein the amino optionally is substituted with:

(1) one or two substituents independently selected from the group consisting of alkyl, alkenyl, alkynyl, alkylcarbonyl, alkylsulfonyl, alkyloxycarbonyl, carbocyclyl, heterocyclyl, carbocyclylalkyl, and heterocyclylalkyl, or, (2) two substituents that, together with the amino nitrogen, form a single-ring heterocyclyl.

In some embodiments, $R^5$ is selected from the group consisting of halo, alkyl, alkenyl, alkynyl, nitro, cyano, azido, alkyloxy, alkenyloxy, alkynyloxy, amino, aminocarbonyl, aminosulfonyl, alkylsulfonyl, carbocyclyl, and heterocyclyl, wherein:

the amino, aminocarbonyl, and aminosulfonyl optionally are substituted with:

(1) one or two substituents independently selected from the group consisting of alkyl, alkenyl, and alkynyl, or, (2) two substituents that, together with the amino nitrogen, form a single-ring heterocyclyl.

In some embodiments, $R^5$ is selected from the group consisting of halo, alkyl, alkenyl, alkynyl, nitro, cyano, azido, alkyloxy, alkenyloxy, alkynyloxy, amino, aminocarbonyl, aminosulfonyl, alkylsulfonyl, carbocyclyl, and heterocyclyl, wherein:

the alkyl, alkenyl, alkynyl, alkyloxy, alkenyloxy, alkynyloxy, alkylsulfonyl, carbocyclyl, and heterocyclyl optionally are substituted with up to three substituents independently selected from the group consisting of halo, oxo, nitro, cyano, azido, hydroxy, amino, alkyloxy, carbocyclyl, and heterocyclyl, wherein the amino optionally is substituted with:

(1) one or two substituents independently selected from the group consisting of alkyl, alkenyl, alkynyl, alkylcarbonyl, alkylsulfonyl, alkyloxycarbonyl, carbocyclyl, heterocyclyl, carbocyclylalkyl, and heterocyclylalkyl, or, (2) two substituents that, together with the amino nitrogen, form a single-ring heterocyclyl.

In some embodiments, $R^5$ is selected from the group consisting of halo, $C_1$-$C_4$-alkyl, $C_2$-$C_4$-alkenyl, $C_2$-$C_4$-alkynyl, amino, $C_1$-$C_4$-alkylsulfonyl, $C_3$-$C_6$-carbocyclyl, and 5-6-membered heterocyclyl, wherein:

(a) the amino optionally is substituted with one or two substituents independently selected from the group consisting of alkyl, alkenyl, alkynyl, and alkylsulfonyl, (b) the $C_1$-$C_4$-alkyl, $C_2$-$C_4$-alkenyl, and $C_2$-$C_4$-alkynyl optionally are substituted with one or more substituents independently selected from the group consisting of halo, oxo, hydroxy, alkyloxy, and trimethylsilyl, and (c) the $C_3$-$C_6$-carbocyclyl and 5-6-membered heterocyclyl optionally are substituted with up to three substituents independently selected from the group consisting of alkyl, alkenyl, alkynyl, halo, and amino, wherein:

the amino optionally is substituted with one or two substituents independently selected from the group consisting of alkyl, alkenyl, alkynyl, and alkylsulfonyl.

In some embodiments, $R^5$ is selected from the group consisting of $C_1$-$C_4$-alkyl, $C_2$-$C_4$-alkenyl, $C_2$-$C_4$-alkynyl, amino, $C_1$-$C_4$-alkylsulfonyl, $C_3$-$C_6$-carbocyclyl, and 5-6-membered heterocyclyl, wherein:

(a) the amino optionally is substituted with one or two substituents independently selected from the group consisting of alkyl, alkenyl, alkynyl, and alkylsulfonyl, (b) the $C_1$-$C_4$-alkyl, $C_2$-$C_4$-alkenyl, and $C_2$-$C_4$-alkynyl optionally are substituted with one or more substituents independently selected from the group consisting of halo, oxo, hydroxy, alkyloxy, and trimethylsilyl, and (c) the $C_3$-$C_6$-carbocyclyl and 5-6-membered heterocyclyl optionally are substituted with up to three substituents independently selected from the group consisting of alkyl, alkenyl, alkynyl, halo, and amino, wherein:

the amino optionally is substituted with one or two substituents independently selected from the group consisting of alkyl, alkenyl, alkynyl, and alkylsulfonyl.

In some embodiments, $R^5$ is selected from the group consisting of halo, $C_1$-$C_4$-alkyl, $C_3$-$C_6$-carbocyclyl, and 5-6-membered heterocyclyl, wherein:

(a) the $C_1$-$C_4$-alkyl optionally is substituted with up to three substituents independently selected from the group consisting of halo, oxo, hydroxy, alkyloxy, and trimethylsilyl, and (b) the $C_3$-$C_6$-carbocyclyl and 5-6-membered heterocyclyl optionally are substituted with one or two substituents independently selected from the group consisting of alkyl, halo, and alkylsulfonylamino.

In some embodiments, $R^5$ is selected from the group consisting of halo, $C_1$-$C_4$-alkyl, $C_3$-$C_6$-carbocyclyl, and 5-6-membered heterocyclyl, wherein:

(a) the $C_1$-$C_4$-alkyl optionally is substituted with one or two substituents independently selected from the group consisting of halo, oxo, hydroxy, alkyloxy, and trimethylsilyl, and (b) the $C_3$-$C_6$-carbocyclyl and 5-6-membered heterocyclyl optionally are substituted with a substituent selected from the group consisting of alkyl, halo, and alkylsulfonylamino.

In some embodiments, $R^5$ is selected from the group consisting of $C_1$-$C_4$-alkyl, $C_3$-$C_6$-carbocyclyl, and 5-6-membered heterocyclyl, wherein:

(a) the $C_3$-$C_4$-alkyl optionally is substituted with up to three substituents independently selected from the group consisting of halo, oxo, hydroxy, alkyloxy, and trimethylsilyl, and (b) the $C_3$-$C_6$-carbocyclyl and 5-6-membered heterocyclyl optionally are substituted with one or two substituents independently selected from the group consisting of alkyl, halo, and alkylsulfonylamino.

In some embodiments, $R^5$ is selected from the group consisting of halo, tert-butyl, $C_3$-$C_6$-carbocyclyl, and 5-6-membered heterocyclyl, wherein:

the $C_3$-$C_6$-carbocyclyl and 5-6-membered heterocyclyl optionally are substituted with a substituent selected from the group consisting of alkyl, halo, and alkylsulfonylamino.

In some embodiments, $R^5$ is selected from the group consisting of tert-butyl, $C_3$-$C_6$-carbocyclyl, and 5-6-membered heterocyclyl, wherein:

the $C_3$-$C_6$-carbocyclyl and 5-6-membered heterocyclyl optionally are substituted with a substituent selected from the group consisting of alkyl, halo, and alkylsulfonylamino.

In some embodiments, $R^5$ is selected from the group consisting of halo, alkyl, haloalkyl, carboxyalkyl, hydroxyalkyl, alkyloxyalkyl, trimethylsilylalkynyl, alkylcarbocyclyl, carbocyclyl, alkylheterocyclyl, heterocyclyl, halocarbocyclyl, alkylsulfonylamino, and alkylsulfonyl.

In some embodiments, $R^5$ is selected from the group consisting of halo, alkyl, alkenyl, alkynyl, nitro, cyano, azido, alkyloxy, alkenyloxy, alkynyloxy, amino, aminocarbonyl, aminosulfonyl, alkylsulfonyl, carbocyclyl, and heterocyclyl.

In some embodiments, $R^5$ is selected from the group consisting of halo, $C_1$-$C_4$-alkyl, $C_2$-$C_4$-alkenyl, $C_2$-$C_4$-alkynyl, amino, $C_1$-$C_4$-alkylsulfonyl, $C_3$-$C_6$-carbocyclyl, and 5-6-membered heterocyclyl. In some such embodiment, $R^5$ is selected from the group consisting of halo, $C_1$-$C_4$-alkyl, $C_2$-$C_4$-alkenyl, $C_2$-$C_4$-alkynyl, amino, $C_1$-$C_4$-alkylsulfonyl, $C_6$-carbocyclyl, and 5-6-membered heterocyclyl. In other such embodiment, $R^s$ is selected from the group consisting of halo, $C_1$-$C_4$-alkyl, $C_2$-$C_4$-alkenyl, $C_2$-$C_4$-alkynyl, amino, $C_1$-$C_4$-alkylsulfonyl, phenyl, and 5-6-membered heteroaryl.

In some embodiments, $R^5$ is selected from the group consisting of $C_1$-$C_4$-alkyl, $C_2$-$C_4$-alkenyl, $C_2$-$C_4$-alkynyl, amino, $C_1$-$C_4$-alkylsulfonyl, $C_3$-$C_6$-carbocyclyl, and 5-6-membered heterocyclyl. In some such embodiment, $R^5$ is selected from the group consisting of $C_1$-$C_4$-alkyl, $C_2$-$C_4$-alkenyl, $C_2$-$C_4$alkynyl, amino, $C_1$-$C_4$-alkylsulfonyl, $C_6$-carbocyclyl, and 5-6-membered heterocyclyl. In other such embodiment, $R^5$ is selected from the group consisting of $C_1$-$C_4$-alkyl, $C_2$-$C_4$-alkenyl, $C_2$-$C_4$-alkynyl, amino, $C_1$-$C_4$-alkylsulfonyl, phenyl, and 5-6-membered heteroaryl.

In some embodiments, $R^s$ is selected from the group consisting of halo, $C_1$-$C_4$-alkyl, $C_3$-$C_6$-carbocyclyl, and 5-6-membered heterocyclyl. In some such embodiments, $R^5$ is selected from the group consisting of halo, $C_1$-$C_4$-alkyl, $C_6$-carbocyclyl, and 5-6-membered heterocyclyl. In other such embodiments, $R^5$ is selected from the group consisting of halo, $C_1$-$C_4$-alkyl, phenyl, and 5-6-membered heteroaryl.

In some embodiments, $R^s$ is selected from the group consisting of $C_1$-$C_4$-alkyl, $C_3$-$C_6$-carbocyclyl, and 5-6-membered heterocyclyl. In some such embodiments, $R^5$ is selected from the group consisting of $C_1$-$C_4$-alkyl, $C_6$-carbocyclyl, and 5-6-membered heterocyclyl. In other such embodiments, $R^5$ is selected from the group consisting of $C_1$-$C_4$-alkyl, phenyl, and 5-6-membered heteroaryl.

In some embodiments, $R^5$ is selected from the group consisting of halo, tert-butyl, $C_3$-$C_6$-carbocyclyl, and 5-6-membered heterocyclyl. In some such embodiments, $R^5$ is selected from the group consisting of halo, tert-butyl, $C_6$-carbocyclyl, and 5-6-membered heterocyclyl. In other such embodiments, $R^5$ is selected from the group consisting of halo, tert-butyl, phenyl, and 5-6-membered heteroaryl.

In some embodiments, $R^5$ is selected from the group consisting of tert-butyl, $C_3$-$C_6$-carbocyclyl, and 5-6-membered heterocyclyl. In some such embodiments, $R^5$ is selected from the group consisting of tert-butyl, $C_6$-carbocyclyl, and 5-6-membered heterocyclyl. In other such embodiments, $R^5$ is selected from the group consisting of tert-butyl, phenyl, and 5-6-membered heteroaryl.

In some embodiments, $R^5$ is selected from the group consisting of $C_3$-$C_6$-carbocyclyl and 5-6-membered heterocyclyl. In some such embodiments, $R^5$ is selected from the group consisting of $C_6$-carbocyclyl, and 5-6-membered heterocyclyl. In other such embodiments, $R^5$ is selected from the group consisting of phenyl and 5-6-membered heteroaryl.

Suitable carbocyclyls for the above embodiments include, for example, cyclopropyl and phenyl.

Suitable heterocyclyls for the above embodiments include, for example, furanyl, thienyl, and pyridinyl.

In some embodiments, $R^5$ is selected from the group consisting of halo, alkyl, and alkyloxy.

In some embodiments, $R^5$ is alkyl.

In some embodiments, $R^5$ is tert-butyl.

Bb. Substituent $R^6$.

$R^6$ is selected from the group consisting of hydrogen, hydroxy, alkyl, alkenyl, alkynyl, alkyloxy, alkenyloxy, alkynyloxy, alkylsulfonyloxy, carbocyclylsulfonyloxy, haloalkylsulfonyloxy, and halo.

In some embodiments, $R^6$ is selected from the group consisting of hydrogen, hydroxy, alkyloxy, and halo. In some such embodiments, $R^6$ is selected from the group consisting of hydrogen, hydroxy, alkyloxy, and fluoro. In other such embodiments, $R^6$ is selected from the group consisting of hydrogen, hydroxy, alkyloxy, and fluoro. In yet other such embodiments, $R^6$ is selected from the group consisting of hydrogen, hydroxy, alkyloxy, and chloro. In yet other such embodiments, $R^6$ is selected from the group consisting of hydrogen, hydroxy, alkyloxy, and bromo. In further such embodiments, $R^6$ is selected from the group consisting of hydrogen, hydroxy, alkyloxy, and iodo.

In some embodiments, $R^6$ is selected from the group consisting of hydrogen, hydroxy, methoxy, and halo. In some such embodiments, $R^6$ is selected from the group consisting of hydrogen, hydroxy, methoxy, and fluoro. In other such embodiments, $R^6$ is selected from the group consisting of hydrogen, hydroxy, methoxy, and chloro. In yet other such embodiments, $R^6$ is selected from the group consisting of hydrogen, hydroxy, methoxy, and bromo. In further such embodiments, $R^6$ is selected from the group consisting of hydrogen, hydroxy, methoxy, and iodo.

In some embodiments, $R^6$ is selected from the group consisting of hydrogen, hydroxy, and alkyloxy. In some such embodiments, $R^6$ is selected from the group consisting of hydrogen, hydroxy, methoxy, and ethoxy.

In some embodiments, $R^6$ is s hydrogen.
In some embodiments, $R^6$ is hydroxy.
In some embodiments, $R^6$ is alkyloxy.
In some embodiments, $R^6$ is methoxy.
In some embodiments, $R^6$ is ethoxy.

B7. Substituent $R^7$.

$R^7$ is selected from the group consisting of hydrogen, $C_5$-$C_6$-carbocyclyl, 5-6-membered heterocyclyl, fused 2-ring carbocyclyl, and fused 2-ring heterocyclyl, wherein the $C_5$-$C_6$-carbocyclyl, 5-6-membered heterocyclyl, fused 2-ring carbocyclyl, and fused 2-ring heterocyclyl optionally are substituted with one or more substituents independently selected from the group consisting of $R^E$, $R^F$, $R^G$, $R^H$, $R^I$, $R^J$, and $R^K$, wherein $R^E$, $R^F$, $R^G$, $R^H$, $R^I$, and $R^K$ are as described below.

In some embodiments, $R^7$ is selected from the group consisting of $C_5$-$C_6$-carbocyclyl, 5-6-membered heterocyclyl, fused 2-ring carbocyclyl, and fused 2-ring heterocyclyl, wherein each such substituent optionally is substituted with one or more substituents independently selected from the group consisting of $R^E$, $R^F$, $R^G$, $R^H$, $R^I$, $R^J$, and $R^K$. In some such embodiments, the $C_5$-$C_6$-carbocyclyl, 5-6-membered heterocyclyl, fused 2-ring carbocyclyl, and fused 2-ring heterocyclyl are not substituted. In other such embodiments, the $C_5$-$C_6$-carbocyclyl, 5-6-membered heterocyclyl, fused 2-ring carbocyclyl, and fused 2-ring heterocyclyl are substituted with a substituent selected from the group consisting of $R^E$, $R^F$, $R^G$, $R^H$, $R^I$, $R^J$, and $R^K$. In other such embodiments, the $C_5$-$C_6$-carbocyclyl, 5-6-membered heterocyclyl, fused 2-ring carbocyclyl, and fused 2-ring heterocyclyl are substituted with a substituent selected from the group consisting of $R^E$, $R^F$, $R^I$, $R^J$, and $R^K$. In other such embodiments, the $C_5$-$C_6$-carbocyclyl, 5-6-membered heterocyclyl, fused 2-ring carbocyclyl, and fused 2-ring heterocyclyl are substituted with a substituent selected from the group consisting of $R^E$, $R^F$, and $R^J$. In other such embodiments, the $C_5$-$C_6$-carbocyclyl, 5-6-membered heterocyclyl, fused 2-ring carbocyclyl, and fused 2-ring heterocyclyl are substituted with a substituent selected from the group consisting of $R^F$ and R. In other such embodiments, the $C_5$-$C_6$-carbocyclyl, 5-6-membered heterocyclyl, fused 2-ring carbocyclyl, and fused 2-ring heterocyclyl are substituted with $R^J$. In yet other such embodiments, the $C_5$-$C_6$-carbocyclyl, 5-6-membered heterocyclyl, fused 2-ring carbocyclyl, and fused 2-ring heterocyclyl are substituted with two substituents independently selected from the group consisting of $R^E$, $R^F$, $R^G$, $R^H$, $R^I$, $R^J$, and $R^K$. In yet other such embodiments, the $C_5$-$C_6$-carbocyclyl, 5-6-membered heterocyclyl, fused 2-ring carbocyclyl, and fused 2-ring heterocyclyl are substituted with two substituents independently selected from the group consisting of $R^E$, $R^F$, $R^I$, $R^J$, and $R^K$. In yet other such embodiments, the $C_5$-$C_6$-carbocyclyl, 5-6-membered heterocyclyl, fused 2-ring carbocyclyl, and fused 2-ring heterocyclyl are substituted with two substituents independently selected from the group consisting of $R^E$, $R^F$, and In yet other such embodiments, the $C_5$-$C_6$-carbocyclyl, 5-6-membered heterocyclyl, fused 2-ring carbocyclyl, and fused 2-ring heterocyclyl are substituted with two substituents independently selected from the group consisting of $R^F$ and $R^J$. In further such embodiments, the $C_5$-$C_6$-carbocyclyl, 5-6-membered heterocyclyl, fused 2-ring carbocyclyl, and fused 2-ring heterocyclyl are substituted with three substituents independently selected from the group consisting of $R^E$, $R^F$, $R^G$, $R^H$, $R^I$, $R^J$, and $R^K$. In further such embodiments, the $C_5$-$C_6$-carbocyclyl, 5-6-membered heterocyclyl, fused 2-ring carbocyclyl, and fused 2-ring heterocyclyl are substituted with three substituents independently selected from the group consisting of $R^E$, $R^F$, $R^I$, $R^J$, and $R^K$. In further such embodiments, the $C_5$-$C_6$-carbocyclyl, 5-6-membered heterocyclyl, fused 2-ring carbocyclyl, and fused 2-ring heterocyclyl are substituted with three substituents independently selected from the group consisting of $R^E$, $R^F$, and $R^J$. In further such embodiments, the $C_5$-$C_6$-carbocyclyl, 5-6-membered heterocyclyl, fused 2-ring carbocyclyl, and fused 2-ring heterocyclyl are substituted with three substituents independently selected from the group consisting of $R^F$ and $R^J$. In further such embodiments, the $C_5$-$C_6$-carbocyclyl, 5-6-membered heterocyclyl, fused 2-ring carbocyclyl, and fused 2-ring heterocyclyl are substituted with one, two, or three substituents independently selected from the group consisting of $R^E$, $R^F$, $R^G$, $R^H$, $R^I$, $R^J$, and $R^K$. In further such embodiments, the $C_5$-$C_6$-carbocyclyl, 5-6-membered heterocyclyl, fused 2-ring carbocyclyl, and fused 2-ring heterocyclyl are substituted with one, two, or three substituents independently selected from the group consisting of $R^E$, $R^F$, $R^I$, $R^J$, and $R^K$. In further such embodiments, the $C_5$-$C_6$-carbocyclyl, 5-6-membered heterocyclyl, fused 2-ring carbocyclyl, and fused 2-ring heterocyclyl are substituted with one, two, or three substituents independently selected from the group consisting of $R^E$, $R^F$, and $R^J$. In further such embodiments, the $C_5$-$C_6$-carbocyclyl, 5-6-membered heterocyclyl, fused 2-ring carbocyclyl, and fused 2-ring heterocyclyl are substituted with one, two, or three substituents independently selected from the group consisting of $R^F$ and $R^J$.

In some embodiments, $R^7$ is selected from the group consisting of $C_5$-$C_6$-carbocyclyl and 5-6-membered heterocyclyl, wherein each such substituent optionally is substituted with one or more substituents independently selected from the group consisting of $R^E$, $R^F$, $R^G$, $R^H$, $R^I$, $R^J$, and $R^K$. In some such embodiments, the $C_5$-$C_6$-carbocyclyl and 5-6-membered heterocyclyl are not substituted. In other such embodiments, the $C_5$-$C_6$-carbocyclyl and 5-6-membered heterocyclyl are substituted with a substituent selected from the group consisting of $R^E$, $R^F$, $R^G$, $R^H$, $R^I$, $R^J$, and $R^K$. In yet other such embodiments, the $C_5$-$C_6$-carbocyclyl and 5-6-membered heterocyclyl are substituted with two substituents independently selected from the group consisting of $R^E$, $R^F$, $R^G$, $R^H$, $R^I$, $R^J$, and $R^K$. In further such embodiments, the $C_5$-$C_6$-carbocyclyl and 5-6-membered heterocyclyl are substituted with three substituents independently selected from the group consisting of $R^E$, $R^F$, $R^G$, $R^H$, $R^I$, $R^J$, and $R^K$. In further such embodiments, the $C_5$-$C_6$-carbocyclyl and 5-6-membered heterocyclyl are substituted with one, two or three substituents independently selected from the group consisting of $R^E$, $R^F$, $R^G$, $R^H$, $R^I$, $R^J$, and $R^K$.

In some embodiments, $R^7$ is $C_5$-$C_6$-carbocyclyl optionally substituted with one or more substituents independently selected from the group consisting of $R^E$, $R^F$, $R^G$, $R^H$, $R^I$, and $R^J$. In some such embodiments, the $C_5$-$C_6$-carbocyclyl is not substituted. In other such embodiments, the $C_5$-$C_6$-carbocyclyl is substituted with a substituent selected from the group consisting of $R^E$, $R^F$, $R^G$, $R^H$, $R^I$, $R^J$, and $R^K$. In yet other such embodiments, the $C_5$-$C_6$-carbocyclyl is substituted with two substituents independently selected from the group consisting of $R^E$, $R^F$, $R^G$, $R^H$, $R^I$, $R^J$, and $R^K$. In further such embodiments, the $C_5$-$C_6$-carbocyclyl is substituted with three substituents independently selected from the group consisting of $R^E$, $R^F$, $R^G$, $R^H$, $R^I$, $R^J$, and $R^K$. In further such embodiments, the $C_5$-$C_6$-carbocyclyl is substituted with one, two, or three substituents independently selected from the group consisting of $R^E$, $R^F$, $R^G$, $R^H$, $R^I$, $R^J$, and $R^K$.

In some embodiments, $R^7$ is 5-6-membered heterocyclyl optionally substituted with one or more substituents independently selected from the group consisting of $R^E$, $R^F$, $R^G$, $R^H$, $R^I$, $R^J$, and $R^K$. In some such embodiments, the 5-6-membered heterocyclyl is not substituted. In other such embodiments, the 5-6-membered heterocyclyl is substituted with a substituent selected from the group consisting of $R^E$, $R^F$, $R^G$, $R^H$, $R^I$, $R^J$, and $R^K$. In yet other such embodiments, the 5-6-membered heterocyclyl is substituted with two substituents independently selected from the group consisting of $R^E$, $R^F$, $R^G$, $R^H$, $R^I$, $R^J$, and $R^K$. In further such embodiments, the 5-6-membered heterocyclyl is substituted with three substituents independently selected from the group consisting of $R^E$, $R^F$, $R^G$, $R^H$, $R^I$, $R^J$, and $R^K$. In further such embodiments, the 5-6-membered heterocyclyl is substituted with one, two, or three substituents independently selected from the group consisting of $R^E$, $R^F$, $R^G$, $R^H$, $R^I$, $R^J$, and $R^K$.

In some embodiments, $R^7$ is selected from the group consisting of fused 2-ring carbocyclyl and fused 2-ring heterocyclyl, wherein each such substituent optionally is substituted with one or more substituents independently selected from the group consisting of $R^E$, $R^F$, $R^G$, $R^H$, $R^I$, $R^J$, and $R^K$. In some such embodiments, the fused 2-ring carbocyclyl and fused 2-ring heterocyclyl are not substituted. In other such embodiments, the fused 2-ring carbocyclyl and fused 2-ring heterocyclyl are substituted with a substituent selected from the group consisting of $R^E$, $R^F$, $R^G$, $R^H$, $R^I$, $R^J$, and $R^K$. In yet other such embodiments, the fused 2-ring carbocyclyl and fused 2-ring heterocyclyl are substituted with two substituents independently selected from the group consisting of $R^E$, $R^F$, $R^G$, $R^H$, $R^I$, $R^J$, and $R^K$. In further such embodiments, the fused 2-ring carbocyclyl and fused 2-ring heterocyclyl are substituted with three substituents independently selected from the group consisting of $R^E$, $R^F$, $R^G$, $R^H$, $R^I$, $R^J$, and $R^K$. In further such embodiments, the fused 2-ring carbocyclyl and fused 2-ring heterocyclyl are substituted with one, two, or three substituents independently selected from the group consisting of $R^E$, $R^F$, $R^G$, $R^H$, $R^I$, $R^J$, and $R^K$.

In some embodiments, $R^7$ is fused 2-ring carbocyclyl optionally substituted with one or more substituents independently selected from the group consisting of $R^E$, $R^F$, $R^G$, $R^H$, $R^I$, $R^J$, and $R^K$. In some such embodiments, the fused 2-ring carbocyclyl is not substituted. In other such embodiments, the fused 2-ring carbocyclyl is substituted with a substituent selected from the group consisting of $R^E$, $R^F$, $R^G$, $R^H$, $R^I$, $R^J$, and $R^K$. In yet other such embodiments, the fused 2-ring carbocyclyl is substituted with two substituents independently selected from the group consisting of $R^E$, $R^F$, $R^G$, $R^H$, $R^I$, $R^J$, and $R^K$. In further such embodiments, the fused 2-ring carbocyclyl is substituted with three substituents independently selected from the group consisting of $R^E$, $R^F$, $R^G$, $R^H$, $R^I$, $R^J$, and $R^K$. In further such embodiments, the fused 2-ring carbocyclyl is substituted with one, two, or three substituents independently selected from the group consisting of $R^E$, $R^F$, $R^G$, $R^H$, $R^I$, $R^J$, and $R^K$.

In some embodiments, $R^7$ is fused 2-ring heterocyclyl optionally substituted with one or more substituents independently selected from the group consisting of $R^E$, $R^F$, $R^G$, $R^H$, $R^I$, $R^J$, and $R^K$. In some such embodiments, the fused 2-ring heterocyclyl is not substituted. In other such embodiments, the fused 2-ring heterocyclyl is substituted with a substituent selected from the group consisting of $R^E$, $R^F$, $R^G$, $R^H$, $R^I$, $R^J$, and $R^K$. In yet other such embodiments, the fused 2-ring heterocyclyl is substituted with two substituents independently selected from the group consisting of $R^E$, $R^F$, $R^G$, $R^H$, $R^I$, $R^J$, and $R^K$. In further such embodiments, the fused 2-ring heterocyclyl is substituted with three substituents independently selected from the group consisting of $R^E$, $R^F$, $R^G$, $R^H$, $R^I$, $R^J$, and $R^K$. In further such embodiments, the fused 2-ring heterocyclyl is substituted with one, two, or three substituents independently selected from the group consisting of $R^E$, $R^F$, $R^G$, $R^H$, $R^I$, $R^J$, and $R^K$.

In some of the above embodiments, the optionally substituted $C_5$-$C_6$-carbocyclyl is selected from the group consisting of cyclopentyl, cyclopentenyl, cyclopentadienyl, cyclohexyl, cyclohexenyl, cyclohexadienyl, and phenyl. In some such embodiments, the optionally substituted $C_5$-$C_6$-carbocyclyl is phenyl.

In some of the above embodiments, the optionally substituted $C_5$-$C_6$-carbocyclyl is $C_5$-carbocyclyl. Examples of $C_5$-carbocyclyls include cyclopentyl, cyclopentenyl, and cyclopentadienyl.

In other of the above embodiments, the optionally substituted $C_5$-$C_6$-carbocyclyl is $C_6$-carbocyclyl. Examples of $C_6$-carbocyclyls include cyclohexyl, cyclohexenyl, cyclohexadienyl, and phenyl.

In some of the above embodiments, the optionally substituted 5-6-membered-heterocyclyl is selected from the group consisting of furanyl, dihydrofuranyl, tetrahydrofuranyl, thiophenyl (thiofuranyl), dihydrothiophenyl, tetrahydrothiophenyl, pyrrolyl, pyrrolinyl, pyrrolidinyl, oxazolyl, dihydrooxazolyl, isoxazolyl, dihydroisoxazolyl, oxazolidinyl, isoxazolidinyl, thiazolyl, isothiazolyl, thiazolinyl, isothiazolinyl, thiazolidinyl, isothiazolidinyl, imidazolyl, imidazolidinyl, pyrazolyl, pyrazolinyl, pyrazolidinyl, oxathiolyl, oxathiolanyl, triazolyl, oxadiazolyl, furazanyl, tetrazolyl, oxatriazolyl, dioxazolyl, oxathiazolyl, oxathiazolidinyl, dihydrooxadiazolyl, dioxazolidinyl, pyranyl, dihydropyranyl, tetrahydropyranyl, pyridinyl, dihydropyridinyl, tetrahydropyridinyl, piperidinyl, diazinyl, pyrazinyl, pyridazinyl, pyrimidinyl, dihydropyrazinyl, tetrahydropyrazinyl, piperazinyl, triazinyl, dihydrotriazinyl, tetrahydrotriazinyl, triazinanyl, oxazinyl, dihydrooxazinyl, morpholinyl, oxathiazinyl, dihydrooxathiazinyl, oxathiazinanyl, oxadiazinyl, dihydrooxadiazinyl, oxadiazinanyl, thiopyranyl, dihydrothiopyranyl, and tetrahydrothiopyranyl.

In some of the above embodiments, the optionally substituted 5-6-membered-heterocyclyl is 5-membered heterocyclyl. Examples of such 5-membered heterocyclyl include furanyl, dihydrofuranyl, tetrahydrofuranyl, thiophenyl (thiofuranyl), dihydrothiophenyl, tetrahydrothiophenyl, pyrrolyl, pyrrolinyl, pyrrolidinyl, oxazolyl, dihydrooxazolyl, isoxazolyl, dihydroisoxazolyl, oxazolidinyl, isoxazolidinyl, thiazolyl, thiazolinyl, isothiazolinyl, thiazolidinyl, isothiazolidinyl, imidazolyl, imidazolidinyl, pyrazolyl, pyrazolinyl, pyrazolidinyl, oxathiolyl, oxathiolanyl, triazolyl, oxadiazolyl, furazanyl, tetrazolyl, oxatriazolyl, dioxazolyl, oxathiazolyl, oxathiazolidinyl, dihydrooxadiazolyl, and dioxazolidinyl.

In other of the above embodiments, the optionally substituted 5-6-membered-heterocyclyl is 6-membered heterocyclyl. Examples of 6-membered heterocyclyls include pyranyl, dihydropyranyl, tetrahydropyranyl, pyridinyl, dihydropyridinyl, tetrahydropyridinyl, piperidinyl, diazinyl, pyrazinyl, pyridazinyl, pyrimidinyl, dihydropyrazinyl, tetrahydropyrazinyl, piperazinyl, triazinyl, dihydrotriazinyl, tetrahydrotriazinyl, triazinanyl, oxazinyl, dihydrooxazinyl, morpholinyl, oxathiazinyl, dihydrooxathiazinyl, oxathiazinanyl, oxadiazinyl, dihydrooxadiazinyl, oxadiazinanyl, thiopyranyl, dihydrothiopyranyl, and tetrahydrothiopyranyl.

In some of the above embodiments, the optionally substituted fused 2-ring carbocyclyl is selected from the group consisting of naphthalenyl, dihydronaphthalenyl, tetrahydronaphthalenyl, hexahydronaphthalenyl, octahydronaphthalenyl, decahydronaphthalenyl, indenyl, dihydroindenyl, hexahydroindenyl, octahydroindenyl, pentalenyl, octahydropentalenyl, and hexahydropentalenyl. In some such embodiments, the optionally substituted fused 2-ring carbocyclyl is selected from the group consisting of naphthalenyl and dihydroindenyl. In some such embodiments, the optionally substituted fused 2-ring carbocyclyl is naphthalenyl. In other such embodiments, the optionally substituted fused 2-ring carbocyclyl is dihydroindenyl. In further such embodiments, the optionally substituted fused 2-ring carbocyclyl is indenyl.

In some of the above embodiments, the optionally substituted fused 2-ring heterocyclyl is selected from the group consisting of

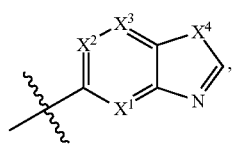

(H1)

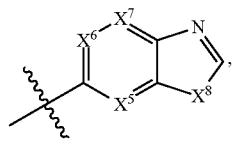

(H2)

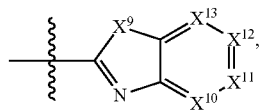

(H3)

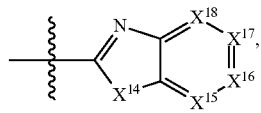

(H4)

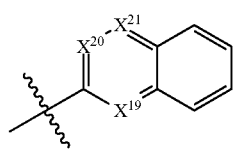

(H5)

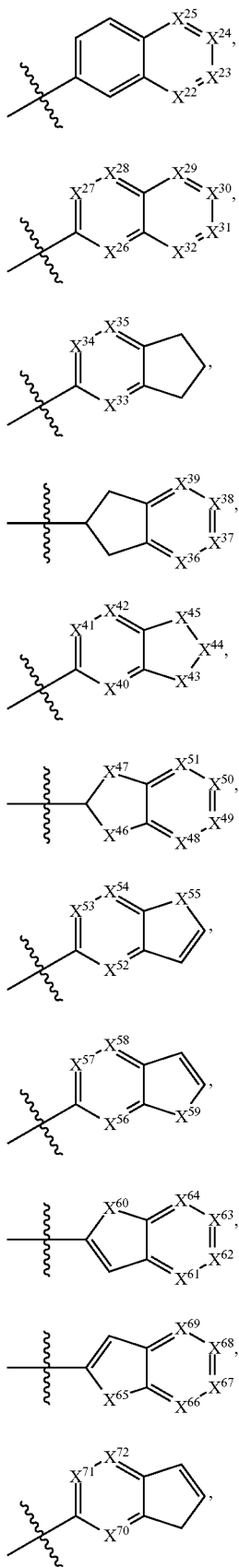
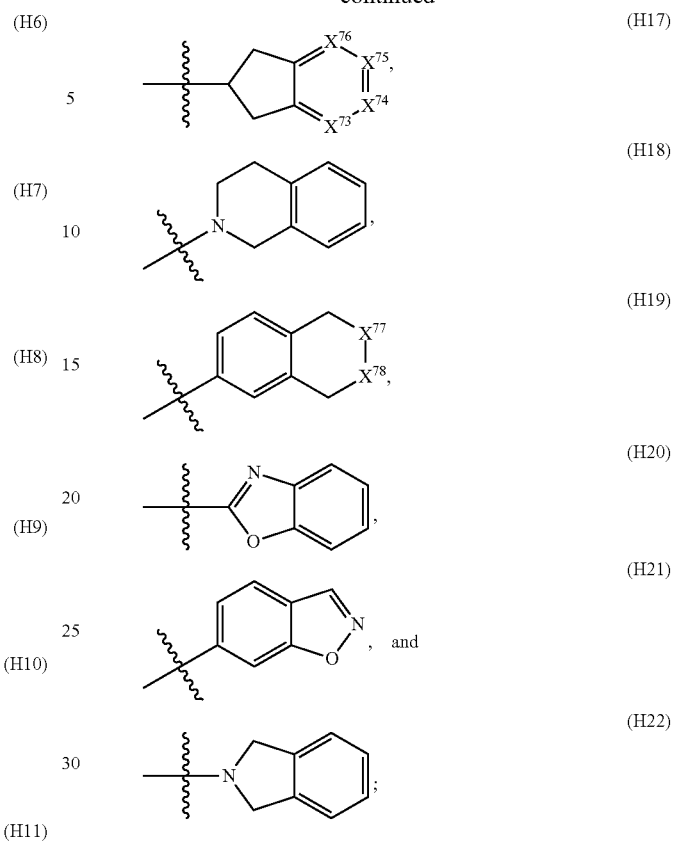

$X^1$, $X^2$, and $X^3$ are independently selected from the group consisting of N and C(H);
$X^4$ is selected from the group consisting of N(H), O, and S;
$X^5$, $X^6$, and $X^7$ are independently selected from the group consisting of N and C(H);
$X^8$ is selected from the group consisting of N(H), O, and S;
$X^9$ is selected from the group consisting of N(H), O, and S;
$X^{10}$, $X^{11}$, $X^{12}$, and $X^{13}$ are independently selected from the group consisting of N and C(H);
$X^{14}$ is selected from the group consisting of N(H), O, and S;
$X^{15}$, $X^{16}$, $X^{17}$, and $X^{18}$ are independently selected from the group consisting of N and C(H);
one or more of $X^{19}$, $X^{20}$, and $X^{21}$ is N, and the remaining one(s) is/are C(H);
one or more of $X^{22}$, $X^{23}$, $X^{24}$, and $X^{25}$ is N, and the remaining one(s) is/are C(H);
one or more of $X^{26}$, $X^{27}$, and $X^{28}$ is N, and the remaining one(s) is/are C(H);
one or more of $X^{29}$, $X^{30}$, $X^{31}$, and $X^{32}$ is N, and the remaining one(s) is/are C(H);
one or more of $X^{33}$, $X^{34}$, and $X^{35}$ is N, and the remaining one(s) is/are C(H);
one or more of $X^{36}$, $X^{37}$, $X^{38}$, and $X^{39}$ is N, and the remaining one(s) is/are C(H);
$X^{40}$, $X^{41}$, $X^{42}$ are independently selected from the group consisting of N and C(H);
one of $X^{43}$, $X^{44}$, and $X^{45}$ is selected from the group consisting of N(H), O, and S, and the remaining two are $C(H)_2$;
one of $X^{46}$ and $X^{47}$ is selected from the group consisting of N(H), O, and S, and the other one is $C(H)_2$;
$X^{48}$, $X^{49}$, $R^{50}$, and $X^{51}$ are independently selected from the group consisting of N and C(H);
$X^{52}$, $X^{53}$, and $X^{54}$ are independently selected from the group consisting of N and C(H);

$X^{55}$ is selected from the group consisting of N(H), O, and S;

$X^{56}$, $X^{57}$, and $X^{58}$ are independently selected from the group consisting of N and C(H);

$X^{59}$ is selected from the group consisting of N(H), O, and S;

$X^{60}$ is selected from the group consisting of N(H), O, and S;

$X^{61}$, $X^{62}$, $X^{63}$, and $X^{64}$ are independently selected from the group consisting of N and C(H);

$X^{65}$ is selected from the group consisting of N(H), O, and S;

$X^{66}$, $X^{67}$, $X^{68}$, and $X^{69}$ are independently selected from the group consisting of N and C(H);

one or more of $X^{70}$, $X^{71}$, and $X^{72}$ is N, and the remaining one(s) is/are C(H);

one or more of $X^{73}$, $X^{74}$, $X^{75}$, and $X^{76}$ is N, and the remaining one(s) is/are C(H); and one of $X^{77}$ and $X^{78}$ is N(H), and the remaining one is $C(H)_2$.

In some of the above embodiments, the optionally substituted fused 2-ring heterocyclyl is selected from the group consisting of

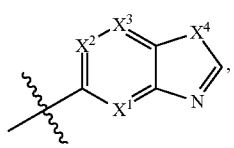 (H1)

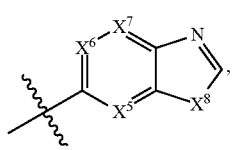 (H2)

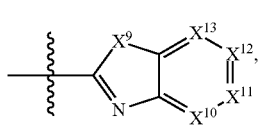 (H3)

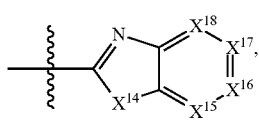 (H4)

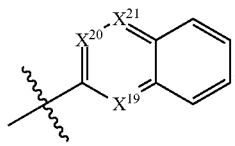 (H5)

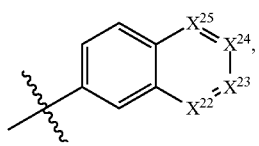 (H6)

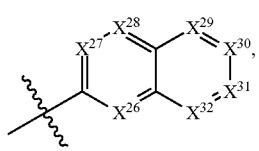 (H7)

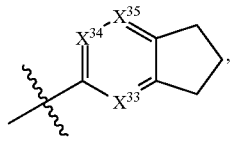 (H8)

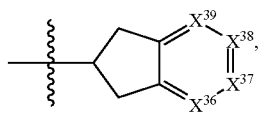 (H9)

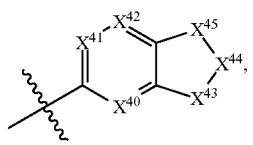 (H10)

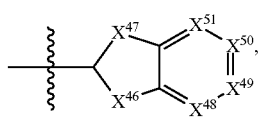 (H11)

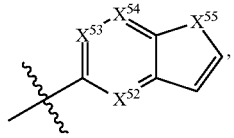 (H12)

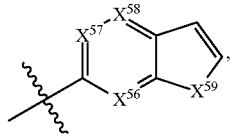 (H13)

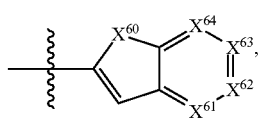 (H14)

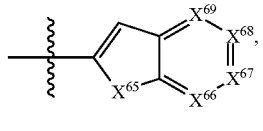 (H15)

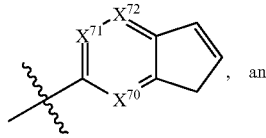, and (H16)

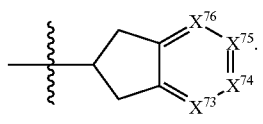 (H17)

In some of the above embodiments, the optionally substituted fused 2-ring heterocyclyl is selected from the group consisting of

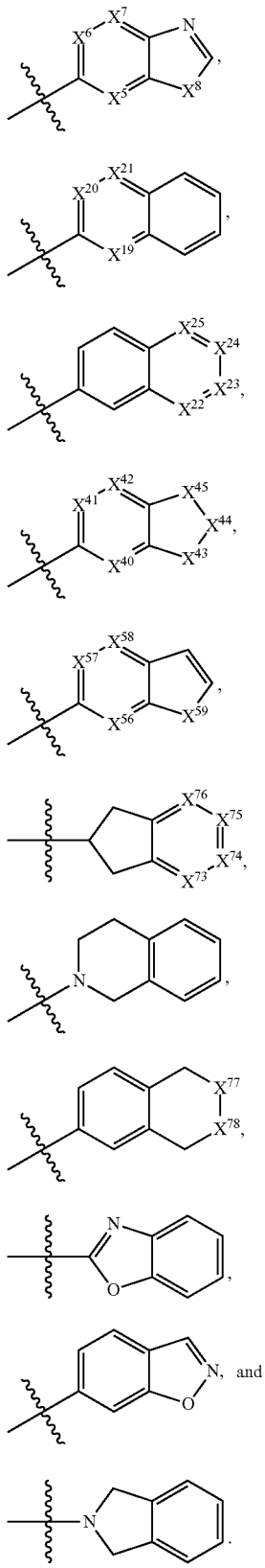

In some of the above embodiments, $X^1$, $X^2$, and $X^3$ are C(H).

In some of the above embodiments, $X^5$, $X^6$, and $X^7$ are C(H).

In some of the above embodiments, $X^{10}$, $X^{11}$, $X^{12}$, and $X^{13}$ are C(H).

In some of the above embodiments, $X^{15}$, $X^{16}$, $X^{17}$, and $X^{18}$ are C(H).

In some of the above embodiments, one of $X^{19}$, $X^{20}$, and $X^{21}$ is N.

In some of the above embodiments, one of $X^{22}$, $X^{23}$, $X^{24}$, and $X^{25}$ is N.

In some of the above embodiments, one of $X^{26}$, $X^{27}$, and $X^{28}$ is N, and one of $X^{29}$, $X^{30}$, $X^{31}$, and $X^{32}$ is N.

In some of the above embodiments, $X^{40}$, $X^{41}$, and $X^{42}$ are C(H).

In some of the above embodiments, $X^{48}$, $X^{49}$, $X^{50}$, and $X^{51}$ are C(H).

In some of the above embodiments, $X^{52}$, $X^{53}$, and $X^{54}$ are C(H).

In some of the above embodiments, $X^{56}$, $X^{57}$, and $X^{58}$ are C(H).

In some of the above embodiments, $X^{61}$, $X^{62}$, $X^{63}$, and $X^{64}$ are C(H).

In some of the above embodiments, $X^{66}$, $X^{67}$, $X^{68}$, and $X^{69}$ are C(H).

In some of the above embodiments, one or more of $X^{70}$, $X^{71}$, and $X^{72}$ is N, and the remaining one(s) is/are C(H).

In some of the above embodiments, one or more of $X^{73}$, $X^{74}$, $X^{75}$, and $X^{76}$ is N, and the remaining one(s) is/are C(H).

In some embodiments, $R^7$ is hydrogen.

B8. Substituent $R^E$

Each $R^E$ is independently selected from the group consisting of halo, nitro, hydroxy, oxo, carboxy, cyano, amino, imino, azido, and aldehydro, wherein the amino optionally is substituted with one or two substituents independently selected from the group consisting of alkyl, alkenyl, and alkynyl.

In some embodiment, each $R^E$ is independently selected from the group consisting of halo, nitro, hydroxy, oxo, carboxy, amino, imino, and aldehydro, wherein the amino optionally is substituted with one or two independently selected alkyl.

In some embodiment, each $R^E$ is independently selected from the group consisting of halo, nitro, hydroxy, oxo, carboxy, amino, imino, aldehydro, and alkylamino.

In some embodiment, each $R^E$ is independently selected from the group consisting of chloro, fluoro, nitro, hydroxy, oxo, carboxy, amino, imino, aldehydro, and alkylamino.

In some embodiment, each $R^E$ is independently selected from the group consisting of halo, nitro, hydroxy, oxo, carboxy, cyano, amino, imino, and azido. In some such embodiments, each $R^E$ is halo. In other such embodiments, each $R^E$ is nitro. In yet other such embodiments, each $R^E$ is hydroxy. In yet other such embodiments, each $R^E$ is oxo. In yet other such embodiments, each $R^E$ is carboxy. In yet other such embodiments, each $R^E$ is cyano. In yet other such embodiments, each $R^E$ is amino. In further such embodiments, each $R^E$ is imino. In yet further such embodiments, each $R^E$ is an azido.

In some embodiments, each $R^E$ is independently selected from the group consisting of halo, nitro, hydroxy, oxo, carboxy, cyano, amino, and imino.

B9. Substituent $R^F$

Each $R^E$ is independently selected from the group consisting of alkyl, alkenyl, and alkynyl, wherein;

each such substituent optionally is substituted with one or more substituents independently selected from the group consisting of carboxy, hydroxy, halo, amino, imino, nitro, azido, oxo, aminosulfonyl, alkylsulfonyl, alkyloxycarbonyl, alkenyloxycarbonyl, alkynyloxycarbonyl, alkylcarbonyloxy, alkenylcarbonyloxy, alkynylcarbonyloxy, alkyloxy, alkenyloxy, alkynyloxy, carbocyclyl, heterocyclyl, cyano, and aminocarbonyl, wherein:
the amino, imino, aminosulfonyl, aminocarbonyl, carbocyclyl, and heterocyclyl optionally are substituted with one or two substituents independently selected from the group consisting of alkyl, alkenyl, alkynyl, alkylsulfonyl, alkenylsulfonyl, alkynylsulfonyl, alkylsulfonylamino, hydroxy, and alkyloxy, wherein:
amino portion of the alkylsulfonylamino optionally is substituted with a substituent selected from the group consisting of alkyl, alkenyl, and alkynyl.

In some embodiment, each $R^E$ is independently selected from the group consisting of alkyl, alkenyl, and alkynyl, wherein:
each such substituent optionally is substituted with one or more substituents independently selected from the group consisting of carboxy, hydroxy, halo, amino, imino, nitro, azido, oxo, aminosulfonyl, alkylsulfonyl, alkyloxycarbonyl, alkenyloxycarbonyl, alkynyloxycarbonyl, alkylcarbonyloxy, alkenylcarbonyloxy, alkynylcarbonyloxy, alkyloxy, alkenyloxy, alkynyloxy, carbocyclyl, heterocyclyl, cyano, and aminocarbonyl, wherein:
the amino, imino, aminosulfonyl, and aminocarbonyl optionally are substituted with one or two substituents independently selected from the group consisting of alkyl, alkenyl, alkynyl, alkylsulfonyl, alkenylsulfonyl, alkynylsulfonyl, and alkylsulfonylamino, wherein:
amino portion of the alkylsulfonylamino optionally is substituted with a substituent selected from the group consisting of alkyl, alkenyl, and alkynyl.

In some of the above embodiments, each $R^F$ is independently selected from the group consisting of the alkyl, alkynyl, and alkynyl, wherein such substituents are not substituted.

In some embodiments, each $R^F$ is independently selected from the group consisting of alkyl, alkenyl, and alkynyl, wherein:
each such substituent optionally is substituted with one or two substituents independently selected from the group consisting of carboxy, hydroxy, halo, amino, imino, nitro, oxo, aminosulfonyl, alkylsulfonyl, alkyloxycarbonyl, alkylcarbonyloxy, alkyloxy, carbocyclyl, heterocyclyl, cyano, and aminocarbonyl, wherein:
the amino, imino, aminosulfonyl, and aminocarbonyl optionally are substituted with one or two substituents independently selected from the group consisting of alkyl, alkylsulfonyl, and alkylsulfonylamino, wherein:
amino portion of the alkylsulfonylamino optionally is substituted with alkyl.

In some embodiments, each $R^F$ is an independently selected alkyl optionally substituted with a substituent selected from the group consisting of carboxy, hydroxy, halo, amino, imino, nitro, oxo, aminosulfonyl, alkylsulfonyl, alkyloxycarbonyl, alkylcarbonyloxy, alkyloxy, carbocyclyl, heterocyclyl, cyano, and aminocarbonyl, wherein:
the amino, imino, aminosulfonyl, and aminocarbonyl optionally are substituted with one or two substituents independently selected from the group consisting of alkyl, alkylsulfonyl, and alkylsulfonylamino, wherein:
amino portion of the alkylsulfonylamino optionally is substituted with alkyl.

In some embodiments, each $R^F$ is an independently selected alkyl optionally substituted with a substituent selected from the group consisting of carboxy, halo, amino, imino, and aminosulfonyl, wherein:
the amino, imino, and aminosulfonyl optionally are substituted with one or two substituents independently selected from the group consisting of alkyl, alkylsulfonyl, and alkylsulfonylamino.

In some embodiments, each $R^F$ is an independently selected alkyl optionally substituted with amino, wherein the amino optionally is substituted with alkylsulfonyl.

In some embodiments, each $R^F$ is an independently selected alkyl substituted with amino, wherein the amino is substituted with alkylsulfonyl. In some such embodiments, each $R^F$ is methylsulfonylaminomethyl.

In some embodiments, each $R^F$ is independently selected from the group consisting of alkyl, alkenyl, and alkynyl, wherein:
each such substituent optionally is substituted with one, two, or three substituents independently selected from the group consisting of carboxy, hydroxy, halo, amino, imino, nitro, azido, oxo, aminosulfonyl, alkylsulfonyl, alkyloxycarbonyl, alkenyloxycarbonyl, alkynyloxycarbonyl, alkylcarbonyloxy, alkenylcarbonyloxy, alkynylcarbonyloxy, alkyloxy, alkenyloxy, alkynyloxy, carbocyclyl, heterocyclyl, cyano, and aminocarbonyl.

In some embodiments, each $R^F$ is independently selected alkyl substituted with one or more substituents independently selected from the group consisting of carboxy, hydroxy, halo, amino, imino, nitro, azido, oxo, aminosulfonyl, alkylsulfonyl, alkyloxycarbonyl, alkenyloxycarbonyl, alkynyloxycarbonyl, alkylcarbonyloxy, alkenylcarbonyloxy, alkynylcarbonyloxy, alkyloxy, alkenyloxy, alkynyloxy, carbocyclyl, heterocyclyl, cyano, and aminocarbonyl.

B10. Substituent $R^G$

Each $R^G$ is independently selected from the group consisting of carbocyclyl and heterocyclyl, wherein:
each such substituent optionally is substituted with one or more substituents independently selected from the group consisting of alkyl, alkenyl, alkynyl, carboxy, hydroxy, halo, amino, nitro, azido, oxo, aminosulfonyl, alkyloxycarbonyl, alkenyloxycarbonyl, alkynyloxycarbonyl, alkylcarbonyloxy, alkenylcarbonyloxy, alkynylcarbonyloxy, alkyloxy, alkenyloxy, alkynyloxy, carbocyclyl, heterocyclyl, cyano, and aminocarbonyl, wherein:
the amino, aminosulfonyl, and aminocarbonyl optionally are substituted with one or two substituents independently selected from the group consisting of alkyl, alkenyl, alkynyl, alkylsulfonyl, alkenylsulfonyl, and alkynylsulfonyl.

In some of the above embodiments, each $R^G$ is independently selected from the group consisting of carbocyclyl and heterocyclyl, wherein such substituents are not substituted.

In some embodiments, each $R^G$ is independently selected from the group consisting of carbocyclyl and heterocyclyl, wherein:
each such substituent optionally is substituted with one or two substituents independently selected from the group consisting of alkyl, carboxy, hydroxy, halo, amino, nitro, oxo, aminosulfonyl, alkyloxycarbonyl, alkylcarbonyloxy, alkyloxy, carbocyclyl, heterocyclyl, cyano, and aminocarbonyl, wherein:
the amino, aminosulfonyl, and aminocarbonyl optionally are substituted with one or two substituents independently selected from the group consisting of alkyl and alkylsulfonyl.

In some of the above embodiments, the carbocyclyl is $C_3$-$C_6$-carbocyclyl.

In some of the above embodiments, the heterocyclyl is 5-6-membered heterocyclyl.

B11. Substituent $R^H$

Each $R^H$ is independently selected from the group consisting of alkyloxy, alkenyloxy, alkynyloxy, alkylsulfonyloxy, alkenylsulfonyloxy, and alkynylsulfonyloxy, wherein:
each such substituent optionally is substituted with one or more substituents independently selected from the group consisting of carboxy, hydroxy, halo, amino, nitro, azido, oxo, aminosulfonyl, alkyloxycarbonyl, alkenyloxycarbonyl, alkynyloxycarbonyl, alkylcarbonyloxy, alkenylcarbonyloxy, alkynylcarbonyloxy, alkyloxy, alkenyloxy, alkynyloxy, carbocyclyl, heterocyclyl, cyano, and aminocarbonyl, wherein:
the amino, aminosulfonyl, and aminocarbonyl optionally are substituted with one or two substituents independently selected from the group consisting of alkyl, alkenyl, alkynyl, alkylsulfonyl, alkenylsulfonyl, and alkynylsulfonyl, In some of the above embodiments, each $R^H$ is independently selected from the group consisting of alkyloxy, alkenyloxy, alkynyloxy, alkylsulfonyloxy, alkenylsulfonyloxy, and alkynylsulfonyloxy, wherein such substituents are not substituted.

In some embodiments, each $R^H$ is independently selected from the group consisting of alkyloxy and alkylsulfonyloxy, wherein:
each such substituent optionally is substituted with one or two substituents independently selected from the group consisting of carboxy, hydroxy, halo, amino, nitro, oxo, aminosulfonyl, alkyloxycarbonyl, alkylcarbonyloxy, alkyloxy, carbocyclyl, heterocyclyl, cyano, and aminocarbonyl, wherein:
the amino, aminosulfonyl, and aminocarbonyl optionally are substituted with one or two substituents independently selected from the group consisting of alkyl and alkylsulfonyl.

In some embodiments, each $R^H$ is independently selected from the group consisting of alkyloxy and alkylsulfonyloxy, wherein:
each such substituent optionally is substituted with one or two substituents independently selected from the group consisting of carboxy, hydroxy, halo, amino, nitro, oxo, aminosulfonyl, alkyloxycarbonyl, alkylcarbonyloxy, alkyloxy, cyano, and aminocarbonyl, wherein:
the amino, aminosulfonyl, and aminocarbonyl optionally are substituted with one or two substituents independently selected from the group consisting of alkyl and alkylsulfonyl.

In some embodiments, each $R^H$ is independently selected from the group consisting of alkyloxy and alkylsulfonyloxy, wherein:
each such substituent optionally is substituted with one or two substituents independently selected from the group consisting of carboxy, hydroxy, halo, amino, nitro, oxo, aminosulfonyl, alkyloxycarbonyl, alkylcarbonyloxy, alkyloxy, cyano, and aminocarbonyl.

In some embodiments, each $R^H$ is independently selected alkyloxy.

In some embodiments, each $R^H$ is independently selected alkylsulfonyloxy.

B12. Substituent $R^I$

Each $R^I$ is independently selected from the group consisting of alkylcarbonyl, alkenylcarbonyl, alkynylcarbonyl, aminocarbonyl, alkyloxycarbonyl, carbocyclylcarbonyl, and heterocyclylcarbonyl, wherein:
(a) the alkylcarbonyl, alkenylcarbonyl, and alkynylcarbonyl optionally are substituted with one or more substituents independently selected from the group consisting of carboxy, hydroxy, halo, amino, nitro, azido, oxo, aminosulfonyl, alkyloxycarbonyl, alkenyloxycarbonyl, alkynyloxycarbonyl, alkylcarbonyloxy, alkenylcarbonyloxy, alkynylcarbonyloxy, alkyloxy, alkenyloxy, alkynyloxy, carbocyclyl, heterocyclyl, cyano, and aminocarbonyl, and
(b) the aminocarbonyl optionally is substituted with one or two substituents independently selected from the group consisting of alkyl, alkenyl, alkynyl, alkyloxyalkyl, carbocyclyl, heterocyclyl, alkylsulfonyl, and alkylsulfonylamino, wherein:
the carbocyclyl and heterocyclyl optionally are substituted with one or two substituents independently selected from the group consisting of halo, alkyl, and oxo.

In some embodiments, each $R^I$ is independently selected from the group consisting of alkylcarbonyl, alkenylcarbonyl, alkynylcarbonyl, aminocarbonyl, alkyloxycarbonyl, carbocyclylcarbonyl, and heterocyclylcarbonyl, wherein such substituents are not substituted.

In some embodiments, each $R^I$ is independently selected from the group consisting of alkylcarbonyl, aminocarbonyl, alkyloxycarbonyl, carbocyclylcarbonyl, and heterocyclylcarbonyl, wherein:
(a) the alkylcarbonyl optionally is substituted with a substituent selected from the group consisting of carboxy, hydroxy, halo, amino, nitro, oxo, aminosulfonyl, alkyloxycarbonyl, alkylcarbonyloxy, alkyloxy, and aminocarbonyl, and
(b) the aminocarbonyl optionally is substituted with a substituent selected from the group consisting of alkyl, alkyloxyalkyl, alkylsulfonyl, and alkylsulfonylamino.

In some embodiments, each $R^I$ is independently selected from the group consisting of alkylcarbonyl and aminocarbonyl, wherein:
the aminocarbonyl optionally is substituted with a substituent selected from the group consisting of alkyl, alkyloxyalkyl, alkylsulfonyl, and alkylsulfonylamino.

In some embodiment, each $R^I$ is independently selected from the group consisting of alkylcarbonyl, alkenylcarbonyl, alkynylcarbonyl, and aminocarbonyl, wherein:
(a) the alkylcarbonyl, alkenylcarbonyl, and alkynylcarbonyl optionally are substituted with one or more substituents independently selected from the group consisting of carboxy, hydroxy, halo, amino, nitro, azido, oxo, aminosulfonyl, alkyloxycarbonyl, alkenyloxycarbonyl, alkynyloxycarbonyl, alkylcarbonyloxy, alkenylcarbonyloxy, alkynylcarbonyloxy, alkyloxy, alkenyloxy, alkynyloxy, carbocyclyl, heterocyclyl, cyano, and aminocarbonyl, and (b) the aminocarbonyl optionally is substituted with one or two substituents independently selected from the group consisting of alkyl, alkenyl, alkynyl, and alkylsulfonylamino.

In some of the above embodiments, each $R^I$ is independently selected from the group consisting of alkylcarbonyl, alkenylcarbonyl, alkynylcarbonyl, and aminocarbonyl, wherein such substituents are not substituted.

In some embodiments, each $R^I$ is independently selected from the group consisting of alkylcarbonyl and aminocarbonyl, wherein:
  (a) the alkylcarbonyl optionally is substituted with one or two substituents independently selected from the group consisting of carboxy, hydroxy, halo, amino, nitro, azido, oxo, aminosulfonyl, alkyloxycarbonyl, alkylcarbonyloxy, alkyloxy, carbocyclyl, heterocyclyl, cyano, and aminocarbonyl, and
  (b) the aminocarbonyl optionally is substituted with one or two substituents independently selected from the group consisting of alkyl and alkylsulfonylamino.

In some embodiments, each $R^I$ is independently selected from the group consisting of alkylcarbonyl and aminocarbonyl, wherein:
  (a) the alkylcarbonyl optionally is substituted with one or two substituents independently selected from the group consisting of carboxy, hydroxy, halo, amino, nitro, oxo, aminosulfonyl, alkyloxycarbonyl, alkylcarbonyloxy, alkyloxy, cyano, and aminocarbonyl, and
  (b) the aminocarbonyl optionally is substituted with one or two substituents independently selected from the group consisting of alkyl and alkylsulfonylamino.

In some embodiments, each $R^I$ is independently selected from the group consisting of alkylcarbonyl and aminocarbonyl, wherein:
  the alkylcarbonyl optionally is substituted with one or two substituents independently selected from the group consisting of carboxy, hydroxy, halo, amino, nitro, azido, oxo, aminosulfonyl, alkyloxycarbonyl, alkylcarbonyloxy, alkyloxy, carbocyclyl, heterocyclyl, cyano, and aminocarbonyl.

In some embodiments, each $R^I$ is independently selected alkylcarbonyl.

In some embodiments, each $R^I$ is independently selected aminocarbonyl.

B13. Substituent $R^J$

Each $R^J$ is independently selected from the group consisting of carbocyclylsulfonylamino, heterocyclylsulfonylamino, alkylcarbonylamino, alkenylcarbonylamino, alkynylcarbonylamino, alkyloxycarbonylamino, alkenyloxycarbonylamino, alkynyloxycarbonylamino, alkylsulfonylamino, alkenylsulfonylamino, alkynylsulfonylamino, aminocarbonylamino, alkyloxycarbonylaminoimino, alkylsulfonylaminoimino, alkenylsulfonylaminoimino, and alkynylsulfonylaminoimino, wherein:
  (a) the amino portion of such substituents optionally is substituted with a substituent independently selected from the group consisting of carbocyclylalkyl, heterocyclylalkyl, alkylcarbonyloxy, aminocarbonylalkyl, alkyl, alkenyl, alkynyl, alkylcarbonyl, alkenylcarbonyl, alkynylcarbonyl, alkyloxycarbonyl, alkyloxyalkyloxycarbonyl, alkylcarbonyloxyalkyl, and alkylsulfonyl, wherein:
    (1) the carbocyclyl portion of the carbocyclylalkyl and the heterocyclyl portion of the heterocyclylalkyl optionally are substituted with one or more substituents independently selected from the group consisting of alkyl, alkenyl, alkynyl, carboxy, hydroxy, alkyloxy, alkenyloxy, alkynyloxy, halo, nitro, cyano, azido, oxo, and amino, and
    (2) the amino portion of the aminocarbonylalkyl optionally is substituted with one or two substituents independently selected from the group consisting of alkyl, alkenyl, and alkynyl,
  (b) the alkyl, alkenyl, and alkynyl portion of such substituents optionally is substituted with one or more substituents independently selected from the group consisting of carboxy, halo, oxo, amino, alkyloxycarbonyl, alkylcarbonyloxy, hydroxy, alkyloxy, carbocyclyl, heterocyclyl, and cyano, wherein:
    the amino optionally is substituted with one or two substituents independently selected from the group consisting of alkyl, alkenyl, alkynyl, alkyloxy, alkenyloxy, and alkynyloxy, wherein:
      the alkyl optionally is substituted with one or more hydroxy;
  (c) the carbocyclyl and heterocyclyl portions of such substituents optionally are substituted with one or more substituents independently selected from the group consisting of alkyl, alkenyl, alkynyl, carboxy, hydroxy, alkyloxy, alkenyloxy, alkynyloxy, halo, nitro, cyano, azido, and amino, wherein:
    the amino optionally is substituted with one or two substituents independently selected from the group consisting of alkyl, alkenyl, and alkynyl.

In some embodiment, each $R^J$ is independently selected from the group consisting of carbocyclylsulfonylamino, heterocyclylsulfonylamino, alkylcarbonylamino, alkenylcarbonylamino, alkynylcarbonylamino, alkyloxycarbonylamino, alkenyloxycarbonylamino, alkynyloxycarbonylamino, alkylsulfonylamino, alkenylsulfonylamino, alkynylsulfonylamino, aminocarbonylamino, alkylsulfonylaminoimino, alkenylsulfonylaminoimino, and alkynylsulfonylaminoimino, wherein:
  (a) the amino portion of such substituents optionally is substituted with a substituent independently selected from the group consisting of carbocyclylalkyl, heterocyclylalkyl, alkylcarbonyloxy, aminocarbonylalkyl, alkyl, alkenyl, alkynyl, alkylcarbonyl, alkenylcarbonyl, alkynylcarbonyl, alkyloxycarbonyl, alkyloxyalkyloxycarbonyl, alkylcarbonyloxyalkyl, and alkylsulfonyl, wherein:
    (1) the carbocyclyl portion of the carbocyclylalkyl and the heterocyclyl portion of the heterocyclylalkyl optionally are substituted with one or more substituents independently selected from the group consisting of alkyl, alkenyl, alkynyl, carboxy, hydroxy, alkyloxy, alkenyloxy, alkynyloxy, halo, nitro, cyano, azido, oxo, and amino, and
    (2) the amino portion of the aminocarbonylalkyl optionally is substituted with one or two substituents independently selected from the group consisting of alkyl, alkenyl, and alkynyl,
  (b) the alkyl, alkenyl, and alkynyl portion of such substituents optionally is substituted with one or more substituents independently selected from the group consisting of carboxy, halo, oxo, amino, alkyloxycarbonyl, alkylcarbonyloxy, hydroxy, alkyloxy, carbocyclyl, heterocyclyl, and cyano, wherein:
    the amino optionally is substituted with one or two substituents independently selected from the group consisting of alkyl, alkenyl, alkynyl, alkyloxy, alkenyloxy, and alkynyloxy, wherein:
the alkyl optionally is substituted with one or more hydroxy;
(c) the carbocyclyl and heterocyclyl portions of such substituents optionally are substituted with one or more substituents independently selected from the group consisting of alkyl, alkenyl, alkynyl, carboxy, hydroxy, alkyloxy, alkenyloxy, alkynyloxy, halo, nitro, cyano, azido, and amino, wherein:
the amino optionally is substituted with one or two substituents independently selected from the group consisting of alkyl, alkenyl, and alkynyl; and In some of the above embodiments, each $R^J$ is independently selected from the group consisting of carbocyclylsulfonylamino, heterocyclylsulfonylamino, alkylcarbonylamino, alkenylcarbonylamino, alkynylcarbonylamino, alkyloxycarbonylamino, alkenyloxycarbonylamino, alkynyloxycarbonylamino, alkylsulfonylamino, alkenylsulfonylamino, alkynylsulfonylamino, aminocarbonylamino, alkylsulfonylaminoimino, alkenylsulfonylaminoimino, and alkynylsulfonylaminoimino, wherein such substituents are not substituted.

In some embodiments, each $R^J$ is independently selected from the group consisting of carbocyclylsulfonylamino, heterocyclylsulfonylamino, alkylcarbonylamino, alkyloxycarbonylamino, alkylsulfonylamino, aminocarbonylamino, and alkylsulfonylaminoimino, wherein:
(a) the amino portion of such substituents optionally is substituted with a substituent independently selected from the group consisting of carbocyclylalkyl, heterocyclylalkyl, alkylcarbonyloxy, aminocarbonylalkyl, alkyl, alkylcarbonyl, alkyloxycarbonyl, alkyloxyalkyloxycarbonyl, alkylcarbonyloxyalkyl, and alkylsulfonyl, wherein:
(1) the carbocyclyl portion of the carbocyclylalkyl and the heterocyclyl portion of the heterocyclylalkyl optionally are substituted with one or two substituents independently selected from the group consisting of alkyl, carboxy, hydroxy, alkyloxy, halo, nitro, cyano, oxo, and amino, and
(2) the amino portion of the aminocarbonylalkyl optionally is substituted with one or two substituents independently selected from the group consisting of alkyl, alkenyl, and alkynyl,
(b) the alkyl portion of such substituents optionally is substituted with one or two substituents independently selected from the group consisting of carboxy, halo, oxo, amino, alkyloxycarbonyl, alkylcarbonyloxy, hydroxy, alkyloxy, carbocyclyl, heterocyclyl, and cyano, wherein:
the amino optionally is substituted with one or two substituents independently selected from the group consisting of alkyl and alkyloxy, wherein:
the alkyl optionally is substituted with one or more hydroxy;
(c) the carbocyclyl and heterocyclyl portions of such substituents optionally are substituted with one or two substituents independently selected from the group consisting of alkyl, carboxy, hydroxy, alkyloxy, halo, nitro, cyano, and amino, wherein:
the amino optionally is substituted with one or two substituents independently selected alkyl.

In some embodiments, each $R^J$ is independently selected from the group consisting of carbocyclylsulfonylamino, heterocyclylsulfonylamino, alkylsulfonylamino, and alkylsulfonylaminoimino, wherein:
the amino portion of such substituents optionally is substituted with a substituent independently selected from the group consisting of carbocyclylalkyl, heterocyclylalkyl, alkylcarbonyloxy, aminocarbonylalkyl, alkyl, alkylcarbonyl, alkyloxycarbonyl, alkyloxyalkyloxycarbonyl, alkylcarbonyloxyalkyl, and alkylsulfonyl, wherein:
(1) the carbocyclyl portion of the carbocyclylalkyl and the heterocyclyl portion of the heterocyclylalkyl optionally are substituted with one or two substituents independently selected from the group consisting of alkyl, carboxy, hydroxy, alkyloxy, halo, nitro, cyano, oxo, and amino, and
(2) the amino portion of the aminocarbonylalkyl optionally is substituted with one or two substituents independently selected from the group consisting of alkyl, alkenyl, and alkynyl.

In some embodiments, each $R^J$ is independently selected from the group consisting of carbocyclylsulfonylamino, heterocyclylsulfonylamino, alkylsulfonylamino, and alkylsulfonylaminoimino, wherein:
the alkyl portion of the alkylsulfonylamino and alkylsulfonylaminoimino optionally is substituted with one or two substituents independently selected from the group consisting of carboxy, halo, oxo, amino, alkyloxycarbonyl, alkylcarbonyloxy, hydroxy, alkyloxy, carbocyclyl, heterocyclyl, and cyano, wherein:

the amino optionally is substituted with one or two substituents independently selected from the group consisting of alkyl and alkyloxy, wherein:
the alkyl optionally is substituted with one or more hydroxy.

In some embodiments, each $R^J$ is independently selected from the group consisting of carbocyclylsulfonylamino, heterocyclylsulfonylamino, alkylsulfonylamino, and alkylsulfonylaminoimino, wherein:
the carbocyclyl and heterocyclyl portions of such substituents optionally are substituted with one or two substituents independently selected from the group consisting of alkyl, carboxy, hydroxy, alkyloxy, halo, nitro, cyano, and amino.

In some embodiments, each $R^J$ is independently selected from the group consisting of carbocyclylsulfonylamino and heterocyclylsulfonylamino, wherein:
the carbocyclyl and heterocyclyl portions of such substituents optionally are substituted with one or two substituents independently selected from the group consisting of alkyl, carboxy, hydroxy, alkyloxy, halo, nitro, cyano, and amino.

In some embodiments, each $R^J$ is independently selected from the group consisting of alkylsulfonylamino, alkenylsulfonylamino, alkynylsulfonylamino, and alkylsulfonylaminoimino, wherein:
(a) the amino portion of such substituents optionally is substituted with a substituent independently selected from the group consisting of carbocyclylalkyl, heterocyclylalkyl, alkylcarbonyloxy, aminocarbonylalkyl, alkyl, alkylcarbonyl, alkyloxycarbonyl, alkyloxyalkyloxycarbonyl, alkylcarbonyloxyalkyl, and alkylsulfonyl, wherein:
(1) the carbocyclyl portion of the carbocyclylalkyl and the heterocyclyl portion of the heterocyclylalkyl optionally are substituted with one or two substituents independently selected from the group consisting of alkyl, carboxy, hydroxy, alkyloxy, halo, nitro, cyano, oxo, and amino, and
(2) the amino portion of the aminocarbonylalkyl optionally is substituted with one or two substituents independently selected from the group consisting of alkyl, alkenyl, and alkynyl,
(b) the alkyl, alkenyl, and alkynyl portion of such substituents optionally is substituted with one or two substituents independently selected from the group consisting of carboxy, halo, oxo, amino, alkyloxycarbonyl, alkylcarbonyloxy, hydroxy, alkyloxy, carbocyclyl, heterocyclyl, and cyano, wherein:
the amino optionally is substituted with one or two substituents independently selected from the group consisting of alkyl and alkyloxy, wherein:
the alkyl optionally is substituted with one or more hydroxy.

In some embodiments, each $R^J$ is an independently selected alkylsulfonylamino, wherein:
(a) the amino portion of the alkylsulfonylamino optionally is substituted with a substituent independently selected from the group consisting of carbocyclylalkyl, heterocyclylalkyl, alkylcarbonyloxy, aminocarbonylalkyl, alkyl, alkylcarbonyl, alkyloxycarbonyl, alkyloxyalkyloxycarbonyl, alkylcarbonyloxyalkyl, and alkylsulfonyl, wherein:
(1) the carbocyclyl portion of the carbocyclylalkyl and the heterocyclyl portion of the heterocyclylalkyl optionally are substituted with one or two substituents independently selected from the group consisting of alkyl, carboxy, hydroxy, alkyloxy, halo, nitro, cyano, oxo, and amino, and
(2) the amino portion of the aminocarbonylalkyl optionally is substituted with one or two substituents independently selected from the group consisting of alkyl, alkenyl, and alkynyl,
(b) the alkyl portion of the alkylsulfonylamino optionally is substituted with one or two substituents independently selected from the group consisting of carboxy, halo, oxo, amino, alkyloxycarbonyl, alkylcarbonyloxy, hydroxy, alkyloxy, carbocyclyl, heterocyclyl, and cyano, wherein:
the amino optionally is substituted with one or two substituents independently selected from the group consisting of alkyl and alkyloxy, wherein:
the alkyl optionally is substituted with one or more hydroxy.

In some embodiments, each $R^J$ is an independently selected alkylsulfonylamino, wherein:
the amino portion of the alkylsulfonylamino optionally is substituted with a substituent independently selected from the group consisting of carbocyclylalkyl, heterocyclylalkyl, alkylcarbonyloxy, aminocarbonylalkyl, alkyl, alkylcarbonyl, alkyloxycarbonyl, alkyloxyalkyloxycarbonyl, alkylcarbonyloxyalkyl, and alkylsulfonyl, wherein:
(1) the carbocyclyl portion of the carbocyclylalkyl and the heterocyclyl portion of the heterocyclylalkyl optionally are substituted with one or two substituents independently selected from the group consisting of alkyl, carboxy, hydroxy, alkyloxy, halo, nitro, cyano, oxo, and amino, and
(2) the amino portion of the aminocarbonylalkyl optionally is substituted with one or two substituents independently selected from the group consisting of alkyl, alkenyl, and alkynyl.

In some embodiments, each $R^J$ is an independently selected alkylsulfonylamino, wherein:
the amino portion of the alkylsulfonylamino optionally is substituted with a substituent independently selected from the group consisting of carbocyclylalkyl, heterocyclylalkyl, alkylcarbonyloxy, aminocarbonylalkyl, alkyl, alkylcarbonyl, alkyloxycarbonyl, alkyloxyalkyloxycarbonyl, alkylcarbonyloxyalkyl, and alkylsulfonyl.

In some embodiments, each $R^J$ is an independently selected alkylsulfonylamino, wherein:
the alkyl portion of the alkylsulfonylamino optionally is substituted with one or two substituents independently selected from the group consisting of carboxy, halo, oxo, amino, alkyloxycarbonyl, alkylcarbonyloxy, hydroxy, alkyloxy, carbocyclyl, heterocyclyl, and cyano, wherein:
the amino optionally is substituted with one or two substituents independently selected from the group consisting of alkyl and alkyloxy, wherein:
the alkyl optionally is substituted with one or more hydroxy.

In some embodiments, each $R^J$ is an independently selected alkylsulfonylamino, wherein:
the alkyl portion of the alkylsulfonylamino optionally is substituted with one or two substituents independently selected from the group consisting of carboxy, halo, oxo, amino, alkyloxycarbonyl, alkylcarbonyloxy, hydroxy, alkyloxy, carbocyclyl, heterocyclyl, and cyano.

In some embodiments, each $R^J$ is an independently selected alkylsulfonylamino. In some such embodiments, each $R^J$ is methylsulfonylamino.

In some embodiments, each $R^J$ is an independently selected alkylsulfonylaminoimino, wherein:
(a) the amino portion of the alkylsulfonylaminoimino optionally is substituted with a substituent independently selected from the group consisting of carbocyclylalkyl, heterocyclylalkyl, alkylcarbonyloxy, aminocarbonylalkyl, alkyl, alkylcarbonyl, alkyloxycarbonyl, alkyloxyalkyloxycarbonyl, alkylcarbonyloxyalkyl, and alkylsulfonyl, wherein:
 (1) the carbocyclyl portion of the carbocyclylalkyl and the heterocyclyl portion of the heterocyclylalkyl optionally are substituted with one or two substituents independently selected from the group consisting of alkyl, carboxy, hydroxy, alkyloxy, halo, nitro, cyano, cow, and amino, and
 (2) the amino portion of the aminocarbonylalkyl optionally is substituted with one or two substituents independently selected from the group consisting of alkyl, alkenyl, and alkynyl,
(b) the alkyl portion of the alkylsulfonylaminoimino optionally is substituted with one or two substituents independently selected from the group consisting of carboxy, halo, oxo, amino, alkyloxycarbonyl, alkylcarbonyloxy, hydroxy, alkyloxy, carbocyclyl, heterocyclyl, and cyano, wherein:
 the amino optionally is substituted with one or two substituents independently selected from the group consisting of alkyl and alkyloxy, wherein:
  the alkyl optionally is substituted with one or more hydroxy.

In some embodiments, each $R^J$ is an independently selected alkylsulfonylaminoimino, wherein:
the amino portion of the alkylsulfonylaminoimino optionally is substituted with a substituent independently selected from the group consisting of carbocyclylalkyl, heterocyclylalkyl, alkylcarbonyloxy, aminocarbonylalkyl, alkyl, alkylcarbonyl, alkyloxycarbonyl, alkyloxyalkyloxycarbonyl, alkylcarbonyloxyalkyl, and alkylsulfonyl, wherein:
 (1) the carbocyclyl portion of the carbocyclylalkyl and the heterocyclyl portion of the heterocyclylalkyl optionally are substituted with one or two substituents independently selected from the group consisting of alkyl, carboxy, hydroxy, alkyloxy, halo, nitro, cyano, oxo, and amino, and
 (2) the amino portion of the aminocarbonylalkyl optionally is substituted with one or two substituents independently selected from the group consisting of alkyl, alkenyl, and alkynyl.

In some embodiments, each $R^J$ is an independently selected alkylsulfonylaminoimino, wherein:
the amino portion of the alkylsulfonylaminoimino optionally is substituted with a substituent independently selected from the group consisting of carbocyclylalkyl, heterocyclylalkyl, alkylcarbonyloxy, aminocarbonylalkyl, alkyl, alkylcarbonyl, alkyloxycarbonyl, alkyloxyalkyloxycarbonyl, alkylcarbonyloxyalkyl, and alkylsulfonyl.

In some embodiments, each $R^J$ is an independently selected alkylsulfonylaminoimino, wherein:
the alkyl portion of the alkylsulfonylaminoimino optionally is substituted with one or two substituents independently selected from the group consisting of carboxy, halo, oxo, amino, alkyloxycarbonyl, alkylcarbonyloxy, hydroxy, alkyloxy, carbocyclyl, heterocyclyl, and cyano, wherein:
 the amino optionally is substituted with one or two substituents independently selected from the group consisting of alkyl and alkyloxy, wherein:
  the alkyl optionally is substituted with one or more hydroxy.

In some embodiments, each $R^J$ is an independently selected alkylsulfonylaminoimino, wherein:
the alkyl portion of the alkylsulfonylaminoimino optionally is substituted with one or two substituents independently selected from the group consisting of carboxy, halo, oxo, amino, alkyloxycarbonyl, alkylcarbonyloxy, hydroxy, alkyloxy, carbocyclyl, heterocyclyl, and cyano.

In some embodiments, each $R^J$ is an independently selected alkylsulfonylaminoimino. In some such embodiments, each $R^J$ is methylsulfonylaminoimino.

In some embodiments, each $R^J$ is independently selected from the group consisting of alkylcarbonylamino and alkyloxycarbonylamino, wherein:
the alkyl portion of such substituents optionally is substituted with one or two substituents independently selected from the group consisting of carboxy, halo, oxo, amino, alkyloxycarbonyl, alkylcarbonyloxy, hydroxy, alkyloxy, carbocyclyl, heterocyclyl, and cyano.

B14. Substituent $R^K$

Each $R^K$ is independently selected from the group consisting of aminosulfonyl, alkylsulfonyl, alkenylsulfonyl, and alkynylsulfonyl, wherein:
(a) the alkylsulfonyl, alkenylsulfonyl, and alkynylsulfonyl optionally are substituted with one or more substituents independently selected from the group consisting of carboxy, hydroxy, halo, amino, nitro, azido, oxo, aminosulfonyl, alkyloxycarbonyl, alkenyloxycarbonyl, alkynyloxycarbonyl, alkylcarbonyloxy, alkenylcarbonyloxy, alkynylcarbonyloxy, alkyloxy, alkenyloxy, alkynyloxy, carbocyclyl, heterocyclyl, cyano, and aminocarbonyl, wherein:
 the amino, aminosulfonyl, and aminocarbonyl optionally are substituted with one or two substituents independently selected from the group consisting of alkyl, alkenyl, and alkynyl; and
(b) the aminosulfonyl optionally is substituted with one or two substituents independently selected from the group consisting of alkyl, alkenyl, and alkynyl.

In some of the above embodiments, each $R^K$ is independently selected from the group consisting of aminosulfonyl, alkylsulfonyl, alkenylsulfonyl, and alkynylsulfonyl, wherein such substituents are not substituted.

In some embodiments, each $R^K$ is independently selected from the group consisting of aminosulfonyl and alkylsulfonyl, wherein:
(a) the alkylsulfonyl optionally is substituted with one or two substituents independently selected from the group consisting of carboxy, hydroxy, halo, amino, nitro, oxo, aminosulfonyl, alkyloxycarbonyl, alkylcarbonyloxy, alkyloxy, carbocyclyl, heterocyclyl, cyano, and aminocarbonyl; and
(b) the aminosulfonyl optionally is substituted with one or two substituents independently selected alkyl.

In some embodiments, each $R^K$ is independently selected from the group consisting of aminosulfonyl and alkylsulfonyl.

C. Embodiments of Compounds of Formula (I)

Various embodiments of substituents $R^1$, $R^2$, $R^3$, $R^4$, $R^5$, $R^6$, $R^7$, $R^E$, $R^F$, $R^G$, $R^H$, $R^I$, $R^J$, and $R^K$ have been discussed above. These substituent embodiments can be combined to form various embodiments of compounds of formula (I). All embodiments of compounds of formula (I) formed by combining the substituent embodiments discussed above are within the scope of Applicants' invention, and some illustrative embodiments of the compounds of formula (I) are provided below.

In some embodiments, the compounds of formula (I) correspond in structure to formula (I-2), wherein:

⁑ is a double carbon-carbon bond;
$R^1$ is hydrogen;
$R^2$ is hydrogen;
$R^3$ is hydrogen;
$R^5$ is $C_1$-$C_4$-alkyl;
$R^6$ is alkyloxy;
$R^7$ is selected from the group consisting of hydrogen and $C_5$-$C_6$-carbocyclyl substituted with one, two, or three substituents independently selected from the group consisting of $R^F$ and $R^J$;
  each $R^F$ is an independently selected alkyl optionally substituted with a substituent selected from the group consisting of carboxy, halo, amino, imino, and aminosulfonyl, wherein:
    the amino, imino, and aminosulfonyl optionally are substituted with one or two substituents independently selected from the group consisting of alkyl, alkylsulfonyl, and alkylsulfonylamino; and
  each $R^J$ is independently selected from the group consisting of alkylsulfonylamino, alkenylsulfonylamino, alkynylsulfonylamino, and alkylsulfonylaminoimino, wherein:
    (a) the amino portion of such substituents optionally is substituted with a substituent independently selected from the group consisting of carbocyclylalkyl, heterocyclylalkyl, alkylcarbonyloxy, aminocarbonylalkyl, alkyl, alkylcarbonyl, alkyloxycarbonyl, alkyloxyalkyloxycarbonyl, alkylcarbonyloxyalkyl, and alkylsulfonyl, wherein:
      (1) the carbocyclyl portion of the carbocyclylalkyl and the heterocyclyl portion of the heterocyclylalkyl optionally are substituted with one or two substituents independently selected from the group consisting of alkyl, carboxy, hydroxy, alkyloxy, halo, nitro, cyano, oxo, and amino, and
      (2) the amino portion of the aminocarbonylalkyl optionally is substituted with one or two substituents independently selected from the group consisting of alkyl, alkenyl, and alkynyl,
    (b) the alkyl, alkenyl, and alkynyl portion of such substituents optionally is substituted with one or two substituents independently selected from the group consisting of carboxy, halo, oxo, amino, alkyloxycarbonyl, alkylcarbonyloxy, hydroxy, alkyloxy, carbocyclyl, heterocyclyl, and cyano, wherein:
      the amino optionally is substituted with one or two substituents independently selected from the group consisting of alkyl and alkyloxy, wherein:
        the alkyl optionally is substituted with one or more hydroxy.

In some embodiments, the compounds of formula (I) correspond in structure to formula (I-6), wherein:

⁑ is selected from the group consisting of single carbon-carbon bond and double carbon-carbon bond;
$R^1$ is hydrogen;
$R^2$ is hydrogen;
$R^3$ is hydrogen;
$R^5$ is $C_1$-$C_4$-alkyl;
$R^7$ is selected from the group consisting of $C_5$-$C_6$-carbocyclyl and 5-6-membered heterocyclyl, wherein each such substituent is substituted with one, two, or three substituents independently selected from the group consisting of $R^E$, $R^F$, $R^J$, and $R^K$;
  each $R^E$ is independently selected from the group consisting of chloro, fluoro, nitro, hydroxy, oxo, carboxy, amino, imino, aldehydro, and alkylamino;
  each $R^F$ is an independently selected alkyl optionally substituted with a substituent selected from the group consisting of carboxy, halo, amino, imino, and aminosulfonyl, wherein:
    the amino, imino, and aminosulfonyl optionally are substituted with one or two substituents independently selected from the group consisting of alkyl, alkylsulfonyl, and alkylsulfonylamino;
  each $R^J$ is independently selected from the group consisting of alkylsulfonylamino, alkenylsulfonylamino, alkynylsulfonylamino, and alkylsulfonylaminoimino, wherein:
    (a) the amino portion of such substituents optionally is substituted with a substituent independently selected from the group consisting of carbocyclylalkyl, heterocyclylalkyl, alkylcarbonyloxy, aminocarbonylalkyl, alkyl, alkylcarbonyl, alkyloxycarbonyl, alkyloxyalkyloxycarbonyl, alkylcarbonyloxyalkyl, and alkylsulfonyl, wherein:
      (1) the carbocyclyl portion of the carbocyclylalkyl and the heterocyclyl portion of the heterocyclylalkyl optionally are substituted with one or two substituents independently selected from the group consisting of alkyl, carboxy, hydroxy, alkyloxy, halo, nitro, cyano, oxo, and amino, and
      (2) the amino portion of the aminocarbonylalkyl optionally is substituted with one or two substituents independently selected from the group consisting of alkyl, alkenyl, and alkynyl,
    (b) the alkyl, alkenyl, and alkynyl portion of such substituents optionally is substituted with one or two substituents independently selected from the group consisting of carboxy, halo, oxo, amino, alkyloxycarbonyl, alkylcarbonyloxy, hydroxy, alkyloxy, carbocyclyl, heterocyclyl, and cyano, wherein:
      the amino optionally is substituted with one or two substituents independently selected from the group consisting of alkyl and alkyloxy, wherein:
        the alkyl optionally is substituted with one or more hydroxy; and
  each $R^K$ is independently selected from the group consisting of aminosulfonyl and alkylsulfonyl, wherein:
    (a) the alkylsulfonyl optionally is substituted with one or two substituents independently selected from the group consisting of carboxy, hydroxy, halo, amino, nitro, oxo, aminosulfonyl, alkyloxycarbonyl, alkylcarbonyloxy, alkyloxy, carbocyclyl, heterocyclyl, cyano, and aminocarbonyl; and
    (b) the aminosulfonyl optionally is substituted with one or two substituents independently selected alkyl.

In some embodiments,

In some embodiments, the compounds of formula (I) correspond in structure to formula (I-10), wherein:

⸗ is a double carbon-carbon bond;

$R^1$ is hydrogen;

$R^2$ is hydrogen;

$R^3$ is hydrogen;

$R^7$ is selected from the group consisting of $C_5$-$C_6$-carbocyclyl and 5-6-membered heterocyclyl, wherein each such substituent is substituted with one, two, or three substituents independently selected from the group consisting of $R^E$, $R^F$, $R^I$, $R^J$, and $R^K$;

each $R^E$ is independently selected from the group consisting of chloro, fluoro, nitro, hydroxy, oxo, carboxy, amino, imino, aldehydro, and alkylamino;

each $R^F$ is an independently selected alkyl optionally substituted with a substituent selected from the group consisting of carboxy, halo, amino, imino, and aminosulfonyl, wherein:
  the amino, imino, and aminosulfonyl optionally are substituted with one or two substituents independently selected from the group consisting of alkyl, alkylsulfonyl, and alkylsulfonylamino;

each $R^I$ is independently selected from the group consisting of alkylcarbonyl and aminocarbonyl, wherein:
  the aminocarbonyl optionally is substituted with a substituent selected from the group consisting of alkyl, alkyloxyalkyl, alkylsulfonyl, and alkylsulfonylamino;

each $R^J$ is independently selected from the group consisting of alkylsulfonylamino, alkenylsulfonylamino, alkynylsulfonylamino, and alkylsulfonylaminoimino, wherein:
  (a) the amino portion of such substituents optionally is substituted with a substituent independently selected from the group consisting of carbocyclylalkyl, heterocyclylalkyl, alkylcarbonyloxy, aminocarbonylalkyl, alkyl, alkylcarbonyl, alkyloxycarbonyl, alkyloxyalkyloxycarbonyl, alkylcarbonyloxyalkyl, and alkylsulfonyl, wherein:
    (1) the carbocyclyl portion of the carbocyclylalkyl and the heterocyclyl portion of the heterocyclylalkyl optionally are substituted with one or two substituents independently selected from the group consisting of alkyl, carboxy, hydroxy, alkyloxy, halo, nitro, cyano, oxo, and amino, and
    (2) the amino portion of the aminocarbonylalkyl optionally is substituted with one or two substituents independently selected from the group consisting of alkyl, alkenyl, and alkynyl,
  (b) the alkyl, alkenyl, and alkynyl portion of such substituents optionally is substituted with one or two substituents independently selected from the group consisting of carboxy, halo, oxo, amino, alkyloxycarbonyl, alkylcarbonyloxy, hydroxy, alkyloxy, carbocyclyl, heterocyclyl, and cyano, wherein:
    the amino optionally is substituted with one or two substituents independently selected from the group consisting of alkyl and alkyloxy, wherein:
      the alkyl optionally is substituted with one or more hydroxy; and each $R^K$ is independently selected from the group consisting of aminosulfonyl and alkylsulfonyl, wherein:
  (a) the alkylsulfonyl optionally is substituted with one or two substituents independently selected from the group consisting of carboxy, hydroxy, halo, amino, nitro, oxo, aminosulfonyl, alkyloxycarbonyl, alkylcarbonyloxy, alkyloxy, carbocyclyl, heterocyclyl, cyano, and aminocarbonyl; and
  (b) the aminosulfonyl optionally is substituted with one or two substituents independently selected alkyl.

In some embodiments, the compounds of formula (I) correspond in structure to formula (I-11); wherein:

⸗ is selected from the group consisting of single carbon-carbon bond and double carbon-carbon bond;

$R^1$ is hydrogen;

$R^2$ is hydrogen;

$R^3$ is hydrogen;

$R^7$ is selected from the group consisting of hydrogen, $C_5$-$C_6$-carbocyclyl, 5-6-membered heterocyclyl, fused 2-ring heterocyclyl, and fused 2-ring carbocyclyl, wherein each such substituent is substituted with one, two, or three substituents independently selected from the group consisting of $R^E$, $R^F$, $R^I$, $R^J$, and $R^K$;

each $R^E$ is independently selected from the group consisting of chloro, fluoro, nitro, hydroxy, oxo, carboxy, amino, imino, aldehydro, and alkylamino;

each $R^F$ is an independently selected alkyl optionally substituted with a substituent selected from the group consisting of carboxy, halo, amino, imino, and aminosulfonyl, wherein:
  the amino, imino, and aminosulfonyl optionally are substituted with one or two substituents independently selected from the group consisting of alkyl, alkylsulfonyl, and alkylsulfonylamino;

each $R^I$ is independently selected from the group consisting of alkylcarbonyl and aminocarbonyl, wherein:
  the aminocarbonyl optionally is substituted with a substituent selected from the group consisting of alkyl, alkyloxyalkyl, alkylsulfonyl, and alkylsulfonylamino;

each $R^J$ is independently selected from the group consisting of alkylsulfonylamino, alkenylsulfonylamino, alkynylsulfonylamino, and alkylsulfonylaminoimino, wherein:
  (a) the amino portion of such substituents optionally is substituted with a substituent independently selected from the group consisting of carbocyclylalkyl, heterocyclylalkyl, alkylcarbonyloxy, aminocarbonylalkyl, alkyl, alkylcarbonyl, alkyloxycarbonyl, alkyloxyalkyloxycarbonyl, alkylcarbonyloxyalkyl, and alkylsulfonyl, wherein:
    (1) the carbocyclyl portion of the carbocyclylalkyl and the heterocyclyl portion of the heterocyclylalkyl optionally are substituted with one or two substituents independently selected from the group consisting of alkyl, carboxy, hydroxy, alkyloxy, halo, nitro, cyano, oxo, and amino, and
    (2) the amino portion of the aminocarbonylalkyl optionally is substituted with one or two substituents independently selected from the group consisting of alkyl, alkenyl, and alkynyl,
  (b) the alkyl, alkenyl, and alkynyl portion of such substituents optionally is substituted with one or two substituents independently selected from the group consisting of carboxy, halo, oxo, amino, alkyloxycarbonyl, alkylcarbonyloxy, hydroxy, alkyloxy, carbocyclyl, heterocyclyl, and cyano, wherein:
    the amino optionally is substituted with one or two substituents independently selected from the group consisting of alkyl and alkyloxy, wherein:
      the alkyl optionally is substituted with one or more hydroxy; and each $R^K$ is independently selected from the group consisting of aminosulfonyl and alkylsulfonyl, wherein:
  (a) the alkylsulfonyl optionally is substituted with one or two substituents independently selected from the group consisting of carboxy, hydroxy, halo, amino, nitro, oxo, aminosulfonyl, alkyloxycarbonyl, alkylcarbonyloxy, alkyloxy, carbocyclyl, heterocyclyl, cyano, and aminocarbonyl; and (b) the aminosulfonyl optionally is substituted with one or two substituents independently selected alkyl.

D. Isomers

This invention also is directed, in part, to all isomers of the compounds of formula (I) (and their salts) (i.e., structural and stereoisomers). Structural isomers include chain and position isomers. Stereoisomers include E/Z isomers (i.e., isomers with regard to one or more double bonds), enantiomers (i.e., stereo-isomers that have opposite configurations at all stereogenic centers), and diastereoisomers (i.e., stereo-isomers that have the same configuration at one or more stereogenic centers, but differ at other stereogenic centers).

E. Salts

This invention also is directed, in part, to all salts of the compounds of formula (I). A salt of a compound may be advantageous due to one or more of the salt's properties, such as, for example, enhanced pharmaceutical stability in differing temperatures and humidities, or a desirable solubility in water or other solvents. Where a salt is intended to be administered to a patient (as opposed to, for example, being in use in an in vitro context), the salt preferably is pharmaceutically acceptable and/or physiologically compatible. The term "pharmaceutically acceptable" is used adjectivally in this patent application to mean that the modified noun is appropriate for use as a pharmaceutical product or as a part of a pharmaceutical product. Pharmaceutically acceptable salts include salts commonly used to form alkali metal salts and to form addition salts of free acids or free bases. In general, these salts typically may be prepared by conventional means by reacting, for example, the appropriate acid or base with a compound of the invention.

Pharmaceutically acceptable acid addition salts of the compounds of formula (I) can be prepared from an inorganic or organic acid. Examples of often suitable inorganic acids include hydrochloric, hydrobromic, hydroiodic, nitric, carbonic, sulfuric, and phosphoric acid. Suitable organic acids generally include, for example, aliphatic, cycloaliphatic, aromatic, araliphatic, heterocyclic, carboxylic, and sulfonic classes of organic acids. Specific examples of often suitable organic acids include acetate, trifluoroacetate, formate, propionate, succinate, glycolate, gluconate, digluconate, lactate, malate, tartaric acid, citrate, ascorbate, glucuronate, maleate, fumarase, pyruvate, aspartate, glutamate, benzoate, anthranilic acid, mesylate, stearate, salicylate, p-hydroxybenzoate, phenylacetate, mandelate, embonate (pamoate), ethanesulfonate, benzenesulfonate, pantothenate, 2-hydroxyethanesulfonate, sulfanilate, cyclohexylaminosulfonate, algenic acid, beta-hydroxybutyric acid, galactarate, galacturonate, adipate, alginate, bisulfate, butyrate, camphorate, camphorsulfonate, cyclopentanepropionate, dodecylsulfate, glycoheptanoate, glycerophosphate, heptanoate, hexanoate, nicotinate, oxalate, palmoate, pectinate, 2-naphthalesulfonate, 3-phenylpropionate, picrate, pivalate, thiocyanate, tosylate, and undecanoate.

Pharmaceutically acceptable base addition salts of the compounds of formula (I) include, for example, metallic salts and organic salts. Preferred metallic salts include alkali metal (group Ia) salts, alkaline earth metal (group IIa) salts, and other physiologically acceptable metal salts. Such salts may be made from aluminum, calcium, lithium, magnesium, potassium, sodium, and zinc. Preferred organic salts can be made from amines, such as tromethamine, diethylamine, N,N'-dibenzylethylenediamine, chloroprocaine, choline, diethanolamine, ethylenediamine, meglumine (N-methylglucamine), and procaine. Basic nitrogen-containing groups can be quaternized with agents such as lower alkyl ($C_1$-$C_6$) halides (e.g., methyl, ethyl, propyl, and butyl chlorides, bromides, and iodides), dialkyl sulfates (e.g., dimethyl, diethyl, dibutyl, and diamyl sulfates), long chain halides (e.g., decyl, lauryl, myristyl, and stearyl chlorides, bromides, and iodides), arylalkyl halides (e.g., benzyl and phenethyl bromides), and others.

F. Purity

Compounds of formula (I) (and salts thereof) with any level of purity (including pure and substantially pure) are within the scope of Applicants' invention. The term "substantially pure" in reference to a compound/salt/isomer, means that the preparation/composition containing the compound/salt/isomer contains more than about 85% by weight of the compound/salt/isomer, preferably more than about 90% by weight of the compound/salt/isomer, preferably more than about 95% by weight of the compound/salt/isomer, preferably more than about 97% by weight of the compound/salt/isomer, and preferably more than about 99% by weight of the compound/salt/isomer.

G. Compositions

This invention also is directed, in part, to compositions comprising one or more compounds and/or salts of the invention (including the crystalline compounds and salts discussed in section E above). In some embodiments, the compositions comprise one or more substantially phase pure crystalline forms (compounds/salts/solvates/hydrates) discussed in section E above. The compositions can be pharmaceutical compositions.

In some embodiments, the compositions further comprise one or more additional therapeutic agents. Such therapeutic agents can, but need not be, additional HCV inhibitors.

The preferred composition depends on the method of administration, and typically comprises one or more conventional pharmaceutically acceptable carriers, adjuvants, and/or vehicles (together referred to as "excipients"). Formulation of drugs is generally discussed in, for example, Hoover, J., Remington's Pharmaceutical Sciences (Mack Publishing Co., 1975) and Ansel's Pharmaceutical Dosage Forms and Drug Delivery Systems (Lippincott Williams & Wilkins, 2005).

Solid dosage forms for oral administration include, for example, capsules, tablets, pills, powders, and granules. In such solid dosage forms, the compounds or salts are ordinarily combined with one or more excipients. If administered per os, the compounds or salts can be mixed with, for example, lactose, sucrose, starch powder, cellulose esters of alkanoic acids, cellulose alkyl esters, talc, stearic acid, magnesium stearate, magnesium oxide, sodium and calcium salts of phosphoric and sulfuric acids, gelatin, acacia gum, sodium alginate, polyvinylpyrrolidone, and/or polyvinyl alcohol, and then tableted or encapsulated for convenient administration. Such capsules or tablets can contain a controlled-release formulation, as can be provided in, for example, a dispersion of the compound or salt in hydroxypropylmethyl cellulose. In the case of capsules, tablets, and pills, the dosage forms also can comprise buffering agents, such as sodium citrate, or magnesium or calcium carbonate or bicarbonate. Tablets and pills additionally can be prepared with enteric coatings.

Liquid dosage forms for oral administration include, for example, pharmaceutically acceptable emulsions (including both oil-in-water and water-in-oil emulsions), solutions (including both aqueous and non-aqueous solutions), suspensions (including both aqueous and non-aqueous suspensions), syrups, and elixirs containing inert diluents commonly used in the art (e.g., water). Such compositions also can comprise, for example, wetting, emulsifying, suspending, flavoring (e.g., sweetening), and/or perfuming agents.

Parenteral administration includes subcutaneous injections, intravenous injections, intramuscular injections, intrasternal injections, and infusion. Injectable preparations (e.g., sterile injectable aqueous or oleaginous suspensions) can be formulated according to the known art using suitable dispersing, wetting agents, and/or suspending agents. Acceptable vehicles and solvents include, for example, water, 1,3-butanediol, Ringer's solution, isotonic sodium chloride solution, bland fixed oils (e.g., synthetic mono- or diglycerides), fatty acids (e.g., oleic acid), dimethyl acetamide, surfactants (e.g., ionic and non-ionic detergents), and/or polyethylene glycols.

Formulations for parenteral administration may, for example, be prepared from sterile powders or granules having one or more of the excipients mentioned for use in the formulations for oral administration. A compound or salt of the invention can be dissolved in water, polyethylene glycol, propylene glycol, ethanol, corn oil, cottonseed oil, peanut oil, sesame oil, benzyl alcohol, sodium chloride, and/or various buffers. The pH may be adjusted, if necessary, with a suitable acid, base, or buffer.

Suppositories for rectal administration can be prepared by, for example, mixing a compound or salt of the invention with a suitable nonirritating excipient that is solid at ordinary temperatures, but liquid at the rectal temperature, and will therefore melt in the rectum to release the drug. Suitable excipients include, for example, cocoa butter; synthetic mono-, di-, or triglycerides, fatty acids, and/or polyethylene glycols.

Topical administration includes the use of transdermal administration, such as transdermal patches or iontophoresis devices.

Other excipients and modes of administration known in the pharmaceutical art also may be used.

The preferred total daily dose of the compound or salt (administered in single or divided doses) is typically from about 0.001 to about 100 mg/kg, more preferably from about 0.001 to about 30 mg/kg, and even more preferably from about 0.01 to about 10 mg/kg (i.e., mg of the compound or salt per kg body weight). Dosage unit compositions can contain such amounts or submultiples thereof to make up the daily dose. In many instances, the administration of the compound or salt will be repeated a plurality of times. Multiple doses per day typically may be used to increase the total daily dose, if desired.

Factors affecting the preferred dosage regimen include the type, age, weight, sex, diet, and condition of the patient; the severity of the pathological condition; the severity of the pathological condition; the route of administration; pharmacological considerations, such as the activity, efficacy, pharmacokinetic, and toxicology profiles of the particular compound or salt used; whether a drug delivery system is utilized; and whether the compound or salt is administered as part of a drug combination. Thus, the dosage regimen actually employed can vary widely, and therefore, can derive from the preferred dosage regimen set forth above.

H. Kits

This invention also is directed, in part, to a kit comprising one or more compounds and/or salts of the in invention. The kit can optionally contain one or more additional therapeutic agents and/or instructions for, for example, using the kit.

L Methods of Use

This invention also is directed, in part, to a method for inhibiting replication of an RNA virus. The method comprises exposing the virus to one or more compounds and/or salts of this invention. In some embodiments, replication of the RNA virus is inhibited in vitro. In other embodiments, replication of the RNA virus is inhibited in vivo. In some embodiments, the RNA virus whose replication is being inhibited is a single-stranded, positive sense RNA virus. In some such embodiments, the RNA virus whose replication is being inhibited is a virus from the Flaviviridae family. In some such embodiments, the RNA virus whose replication is being inhibited is HCV.

This invention also is directed, in part, to a method for inhibiting HCV RNA polymerase. The method comprises exposing the polymerase with one or more compounds and/or salts of this invention. In some embodiments, HCV RNA polymerase activity is inhibited in vitro. In other embodiments, HCV RNA polymerase activity is inhibited in vivo.

The term "inhibiting" means reducing the level of RNA virus replication/HCV polymerase activity either in vitro or in vivo. For example, if a compound/salt of the invention reduces the level of RNA virus replication by at least about 10% compared to the level of RNA virus replication before the virus was exposed to the compound/salt, then the compound/salt inhibits RNA virus replication. In some embodiments, the compound/salt can inhibit RNA virus replication by at least about 20%, at least about 30%, at least about 40%, at least about 50%, at least about 60%, at least about 70%, at least about 80%, at least about 90%, or at least about 95%.

This invention also is directed, in part, to a method for treating a disease that can be treated by inhibiting HCV RNA polymerase. Thus, this invention also is directed, in part, to a method for treating hepatitis C in an animal in need of such treatment. These methods comprise administering to the animal one or more compounds and/or salts of the invention, and, optionally, one or more additional therapeutic agents. In some embodiments, a therapeutically effective amount of the compound(s) and/or salt(s) is administered to the animal. "Treating" means ameliorating, suppressing, eradicating, preventing, reducing the risk of, and/or delaying the onset of the disease being treated. Applicants specifically intend that the term "treating" encompass administration of the compounds and/or salts of the invention to an HCV-negative patient that is a candidate for an organ transplant. The methods of treatment are particularly suitable for use with humans, but may be used with other animals, particularly mammals. A "therapeutically-effective amount" or "effective amount" is an amount that will achieve the goal of treating the targeted condition.

In some embodiments, the methods comprise combination therapy, wherein the compound(s) and/or salt(s) of the invention is/are co-administered with a second (or even a third, fourth, etc.) compound, such as, for example, another therapeutic agent used to treat hepatitis C (e.g., interferon or interferon/ribavirin combination, or an HCV inhibitor such as, for example, an HCV polymerase inhibitor or an HCV protease inhibitor). The compound(s) and/or salt(s) of this invention can also be co-administered with therapeutic agents other than therapeutic agents used to treat hepatitis C (e.g., anti-HIV agents). In these co-administration embodiments, the compound(s) and/or salt(s) of the invention and the second, etc. therapeutic agent(s) may be administered in a substantially simultaneous manner (e.g., or within about 5 minutes of each other), in a sequential manner, or both. It is contemplated that such combination therapies may include administering one therapeutic agent multiple times between the administrations of the other. The time period between the administration of each agent may range from a few seconds (or less) to several hours or days, and will depend on, for example, the properties of each composition and active ingredient (e.g., potency, solubility, bioavailability, half-life, and kinetic profile), as well as the condition of the patient. The compound(s) and/or salt(s) of this invention and the second, etc. therapeutic agent may also be administered in a single formulation.

This invention also is directed, in part, to a use of one or more compounds and/or salts of the invention, and, optionally one or more additional therapeutic agents to prepare a medicament. In some embodiments, the medicament is for co-administration with one or more additional therapeutic agents.

In some embodiments, the medicament is for inhibiting replication of an RNA virus.

In some embodiments, the medicament is for treating hepatitis C.

This invention also is directed, in part, to one or more compounds and/or salts of the invention, and, optionally one or more additional therapeutic agents, for use as a medicament. In some embodiments, the medicament is for inhibiting replication of an RNA virus. In other embodiments, the medicament is for treating hepatitis C.

J. Methods for Preparation

Additional information about the preparation of compounds of formulas (I) (and their salts) is provided in the general discussion and/or specific synthesis examples below. In the discussion below, $R^1$, $R^2$, $R^3$, $R^4$, $R^5$, $R^6$, $R^7$, $R^E$, $R^F$, $R^G$, $R^H$, $R^I$, $R^J$, and $R^K$ have the meaning discussed above unless otherwise stated.

Scheme 1

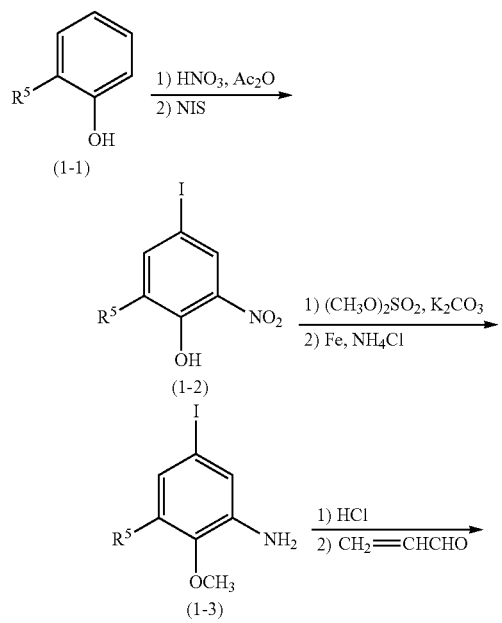

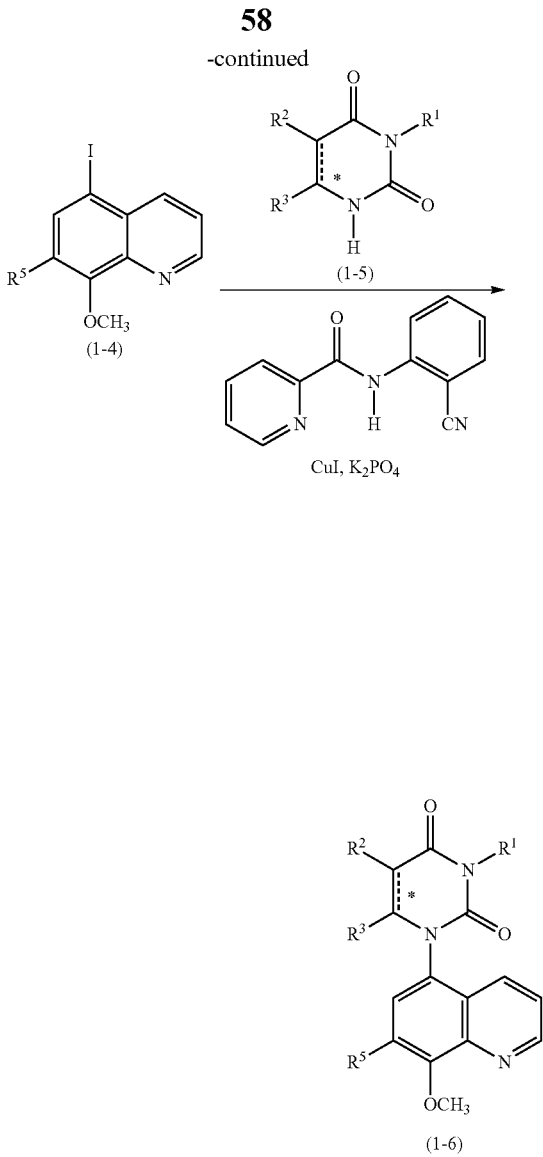

As described in Scheme 1, compounds of formula (1-6), wherein $R^1$, $R^2$, $R^3$ and $R^5$ are as described in the Summary of the Invention can be prepared from compounds of formula (1-1). Compounds of formula (1-1) can be reacted first with nitric acid in acetic anhydride and then with N-iodosuccinimide (NIS) to give compounds of formula (1-2). The phenol of compounds of formula (1-2) can be alkylated with dimethyl sulfate in the presence of base and then the nitro moiety can be reduced to the corresponding aniline with iron in the presence of ammonium chloride to give compounds of formula (1-3). Compounds of formula (1-3) can be converted to compounds of formula (1-4) by treating first with acid and then with acrolein. Compounds of formula (1-4) can be coupled with compounds of formula (1-5) with copper(I) iodide in the presence of a base and ligand such as N-(2-cyanophenyl)picolinamide to give compounds of formula (1-6). Compounds of formula (I-6) are representative of compounds of formula (I).

Scheme 2

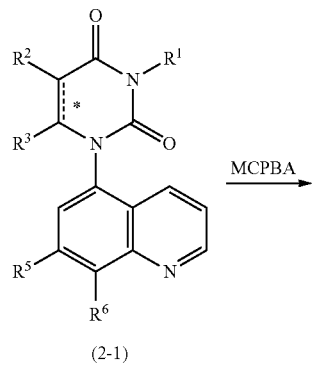

(2-1)

MCPBA →

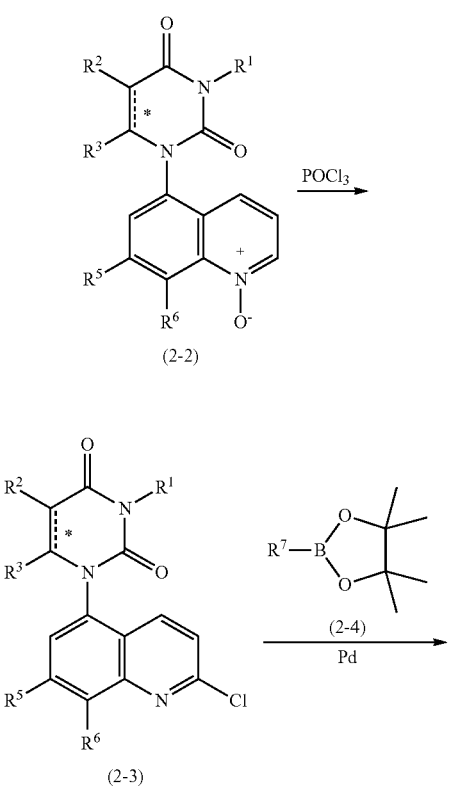

(2-2) POCl₃ →

(2-3) (2-4)/Pd →

(2-5) 1) acid 2) MsCl →

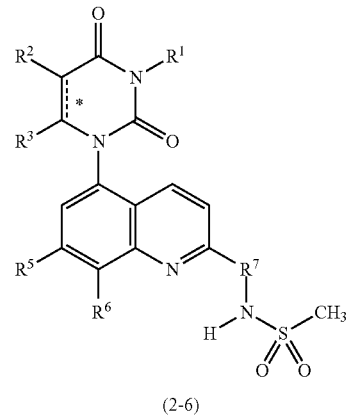

(2-6)

As described in Scheme 2, compounds of formula (2-6), wherein $R^1$, $R^2$, $R^3$, $R^5$ and $R^6$ are as described in the Summary of the Invention and $R^7$ is $C_5$-$C_6$-carbocyclyl, 5-6-membered heterocyclyl, fused 2-ring carbocyclyl or fused 2-ring heterocyclyl can be prepared from compounds of formula (2-1). Compounds of formula (2-1) can be reacted with m-chloroperoxybenzoic acid (MCPBA) to give compounds of formula (2-2). Compounds of formula (2-2) are converted to compounds of formula (2-3) upon treatment with phosphorus oxychloride. A Suzuki reaction between compounds of formulas (2-3) and (2-4) (or the corresponding boronic acid) delivers compounds of formula (2-5). In some instances, $R^7$ is substituted with $R^J$ which can be alkyloxycarbonylamino or in particular, tert-butoxycarbonylamino. In those instances wherein in $R^J$ is tert-butoxycarbonylamino, compounds of formula (1-5) can be treated first with an acid such as hydrochloric acid or trifluoroacetic acid to remove the tert-butoxycarbonyl group and subsequently sulfonylated with a reagent such as methanesulfonyl chloride (MSCl) to give compounds of formula (2-6). Compounds of formula (2-6) are representative of compounds of formula (I).

Scheme 3

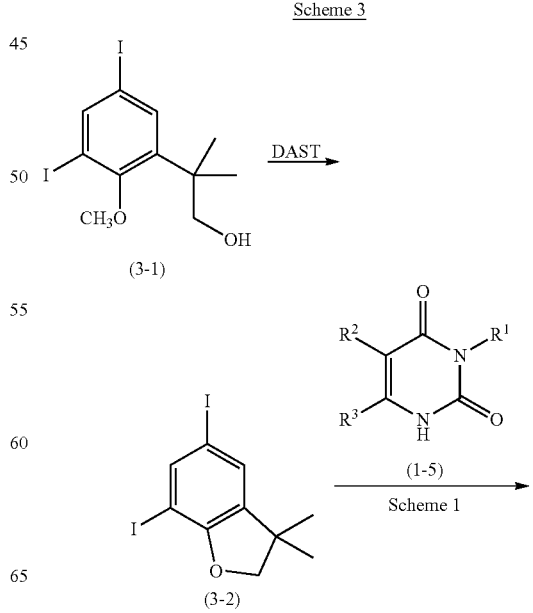

(3-1) DAST →

(3-2) (1-5) Scheme 1 →

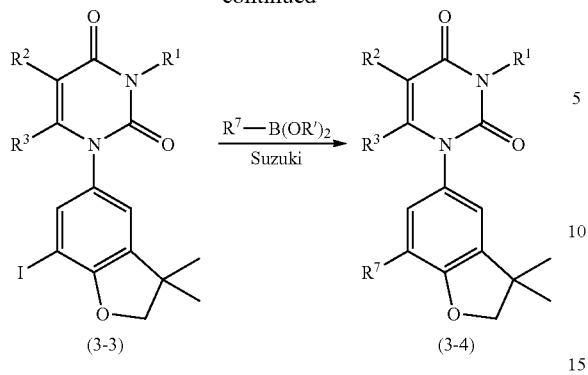

As described in Scheme 3, compounds of formula (3-4), wherein $R^1$, $R^2$, and $R^3$ are as described in the Summary of the Invention and $R^7$ is $C_5$-$C_6$-carbocyclyl, 5-6-membered heterocyclyl, fused 2-ring carbocyclyl or fused 2-ring heterocyclyl can be prepared from a compound of formula (3-1). A compounds of formula (3-1) can be reacted with diethylaminosulfur trifluoride (DAST) to give the compound of formula (3-2). Compounds of formula (1-5) can be coupled to a compound of formula (3-2) using the methodology described in Scheme 1 to give compounds of formula (3-3). Compounds of formula (3-3) can be reacted with compounds of formula $R^7$—$B(OR')_2$, wherein R' is hydrogen, alkyl or taken to together with the boron and oxygen atoms form 4,4,5,5-tetramethyl-1,3,2-dioxaborolane, under Suzuki reaction conditions to give compounds of formula (3-4). Compounds of formula (3-4) are representative of compounds of formula (I).

As described in Scheme 4, compounds of formula (4-4), wherein $R^2$ and $R^3$ are as described in the Summary of the Invention can be prepared from a compound of formula (4-1). A compounds of formula (4-1) can be nitrated with nitric acid in a mixture of acetic acid and sulfuric acid. Subsequent reduction with iron in the presence of ammonium chloride gives a compound of formula (4-2). A compound of formula (4-2) can be reacted with an acrylic acid of formula (4-3). Subsequent treatment with urea under acidic conditions furnishes compounds of formula (4-4). Compounds of formula (4-4) are representative of compounds of formula (I).

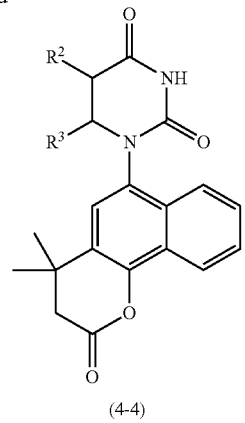

Scheme 5

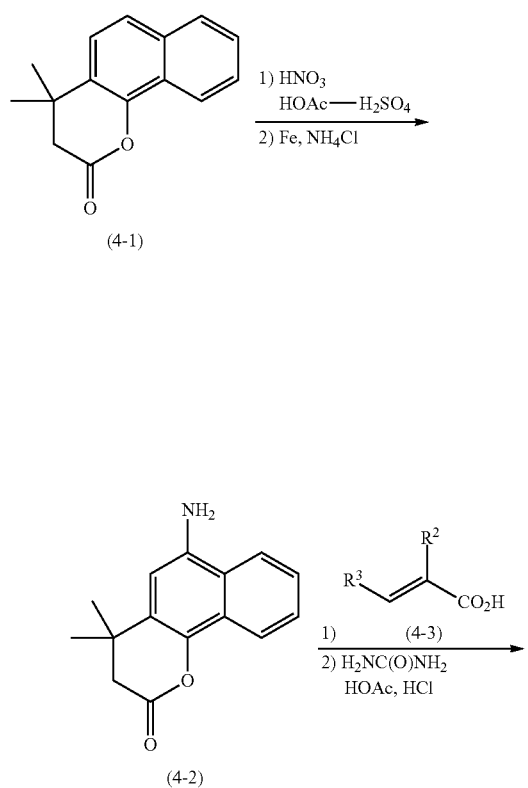

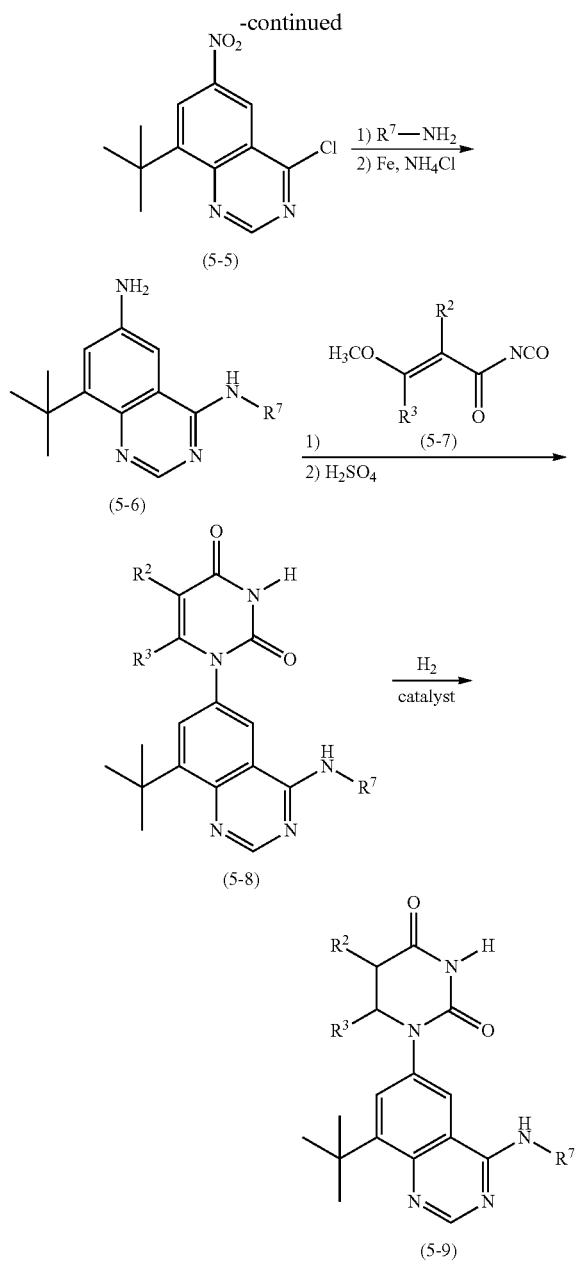

of the chlorine in a compound of formula (5-5) with an amine of formula $R^7—NH_2$ and subsequent reduction of the nitro group gives compounds of formula (5-6). Reaction of compounds of formula (5-6) with a 3-methoxyacryloyl isocyanate of formula (5-7) and subsequent cyclization under acidic conditions give compounds of formula (5-8). Catalytic hydrogenation of compounds of formula (5-8) delivers compounds of formula (5-9). Compounds of formulas (5-8) and (5-9) are representative of compounds of formula (I).

EXAMPLES

The following examples are merely illustrative, and not limiting to this disclosure in any way.

Example 1

Preparation of 1-(7-tert-butyl-8-methoxyquinolin-5-yl)pyrimidine-2,4(1H,3H)-dione

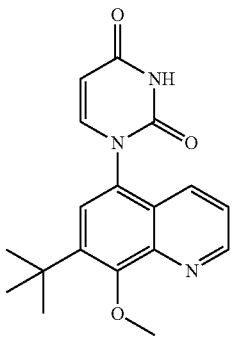 [SMILES: COc1c(C(C)(C)C)cc(-n2ccc(=O)[nH]c2=O)c2cccnc12]

Part A. Preparation of 2-tert-butyl-6-nitrophenol.

Nitric acid (0.595 mL, 13.31 mmole, 70%) was added dropwise to a chilled stirred flask containing acetic anhydride (1.26 mL, 13.31 mmole). The resulting light yellow solution was stirred for 5 minutes then added dropwise over 5 minutes to a cold (0-5° C.) acetonitrile solution containing 2-t-butylphenol (2 g, 13.31 mmole). The mixture was stirred for 10 minutes after addition was complete and then diluted with 100 mL of water. The mixture was extracted with ether. The combined organic extracts were washed with water and brine, dried (magnesium sulfate), filtered and concentrated in vacuo. The dark red oil was purified by flash column chromatography on silica gel eluting with 3:1 hexane/acetone to give the title compound as a clear oil (0.64 g, 25%). $^1$H NMR (300 MHz, DMSO-$d_6$) δ ppm 1.43 (s, 9H), 6.99 (dd, J=7.7, 8.4, 1H), 7.62 (dd, J=1.6, 7.7, 1H), 7.91 (dd, J=1.8, 8.4, 1H), 10.92 (s, 1H).

Part B. Preparation of 2-tert-butyl-4-iodo-6-nitrophenol.

2-tert-Butyl-6-nitrophenol (2.68 g, 13.73 mmole) was dissolved in 90 mL of acetonitrile. The flask was covered in foil, and N-iodosuccinimide (3.90 g, 16.47 mmole) was added in portions at approximately 15 minute intervals over a 1 hour period. The reaction was stirred at room temperature for 2 hours and then concentrated in vacuo. The oily residue was dissolved in 100 mL of ether and treated with 70 mL of 10% sodium thiosulfate solution with stirring for 30 minutes. The layers were separated. The organic layer was washed with water and brine, dried (sodium sulfate), filtered and concentrated in vacuo. The brown oily residue was purified by flash column chromatography on silica gel eluting with 2% ethyl acetate/hexane to give title compound as a yellow solid (2.80

As described in Scheme 5, compounds of formula (5-8) and (5-9), wherein $R^2$ and $R^3$ are as described in the Summary of the Invention and $R^7$ is $C_5$-$C_6$-carbocyclyl, 5-6-membered heterocyclyl, fused 2-ring carbocyclyl or fused 2-ring heterocyclyl can be prepared from a compound of formula (5-1). A heated acidic mixture of a compound of formula (5-1), hydroxylamine hydrochloride, and a dehydrating reagent can be treated with 2,2,2-trichloro-1-ethoxyethanol to give a compound of formula (5-2). A compound of formula (5-2) is converted to a compound of formula (5-3) upon treatment with acid. A compound of formula (5-3) can be nitrated with potassium nitrate in the presence of acid and then hydrolyzed with hydrogen peroxide in the presence of a base to give a compound of formula (5-4). A compound of formula (5-4) can be heated conventionally or in a microwave reactor in the presence of formamide to generate a quinazolin-4(3H)-one. Reaction of the quinazolin-4(3H)-one with phosphorus oxychloride provides a compound of formula (5-5). Substitution g, 64%). ¹H NMR (300 MHz, DMSO-d₆) δ ppm 1.39 (s, 9H) 7.73 (d, J=2.21 Hz, 1H) 8.15 (d, J=1.84 Hz, 1H) 10.89 (s, 1H).

Part C. Preparation of 1-tert-butyl-5-iodo-2-methoxy-3-nitrobenzene.

2-tert-Butyl-4-iodo-6-nitrophenol (0.32 g, 0.997 mmole), potassium carbonate (0.21 g, 1.495 mmole) and dimethyl sulfate (0.105 mL, 1.096 mmole) were combined and heated at reflux for 16 hours. The reaction mixture was filtered, washed with acetone and concentrated in vacuo. The oily residue was dissolved in ethyl acetate, washed with water and brine, dried (sodium sulfate), filtered and concentrated in vacuo to give the title compound as a light yellow oil (0.25 g, 75%). ¹H NMR (300 MHz, DMSO-d₆) δ ppm 1.45 (s, 9H), 3.73 (s, 3H), 7.79 (d, J=2.2, 1H), 8.08 (d, J=2.2, 1H).

Part D. Preparation of 3-tert-butyl-5-iodo-2-methoxyaniline.

1-tert-Butyl-5-iodo-2-methoxy-3-nitrobenzene (0.25 g, 0.746 mmole), iron powder (0.167 g, 2.98 mmole) and ammonium chloride (0.048 g, 0.895 mmole) were combined in a 3 mL:3 mL:1 mL mixture of tetrahydrofuran:ethanol:water and heated at reflux for 2 hours. The mixture was filtered and washed twice with hot methanol, and the solvent was concentrated in vacuo. The oily residue was dissolved in ethyl acetate, washed with water and brine, dried (sodium sulfate), filtered and concentrated in vacuo to give the title compound as a yellow oil (0.2 g, 88%). ¹H NMR (300 MHz, DMSO-d₆) δ ppm 1.41 (s, 9H), 3.69 (s, 3H), 5.02 (s, 2H), 6.65 (d, J=2.4, 1H), 6.95 (d, J=2.2, 1H).

Part E. Preparation of 7-tert-butyl-5-iodo-8-methoxyquinoline.

3-tert-Butyl-5-iodo-2-methoxyaniline (0.2 g, 0.655 mmole) was treated with 6 N hydrochloric acid (7 mL) and heated to reflux. Acrolein (0.263 mL, 3.93 mmole) was added dropwise over 2 minutes to the refluxing solution. The initial thick slurry became dark and homogeneous over 5 minutes after addition. Heating of the reaction mixture was continued for 20 minutes. The reaction mixture was then cooled, diluted with 20 mL of water, and extracted with ether. The aqueous layer was made basic with 15% sodium hydroxide, and extracted with dichloromethane. The combined organic extracts were washed with brine, dried (magnesium sulfate), filtered and concentrated in vacuo. The brown oil was purified by flash column chromatography on silica gel eluting with dichloromethane to give the title compound as a tan solid (50 mg, 22%). ¹H NMR (300 MHz, DMSO-d₆) δ ppm 1.41 (s, 9H), 4.14 (s, 3H), 7.60 (dd, J=4.2, 8.6, 1H), 8.05 (s, 1H), 8.36-8.20 (m, 11-1), 9.00-8.82 (m, 1H).

Part F. Preparation of 1-(7-tert-butyl-8-methoxyquinolin-5-yl)pyrimidine-2,4(1H,3H)-dione.

7-tert-Butyl-5-iodo-8-methoxyquinoline (50 mg, 0.147 mmole), potassium phosphate (2.1 equivalents, 0.308 mmole), copper(I) iodide (0.1 equivalents, 0.015 mmole), uracil (1.2 equivalents, 0.176 mmole) and N-(2-cyanophenyl)picolinamide (0.2 equivalents, 0.029 mmole) were combined and heated in dimethyl sulfoxide (0.6 mL) for 16 hours at 70° C. The reaction mixture was cooled to room temperature, 5 mL of water was added followed by extraction with 25 mL of ethyl acetate. The aqueous layer was extracted with another 25 mL of ethyl acetate and the combined organic extracts were washed with water and brine, dried (sodium sulfate), filtered and concentrated in vacuo. The green oily residue was purified by flash column chromatography on silica gel eluting with 2% methanol/dichloromethane to give 6 mg of title compound containing a colored impurity. The material was repurified on a 1 g silica gel cartridge eluting with 1% methanol/dichloromethane to give the title compound (2.2 mg, 5%). ¹H NMR (300 MHz, DMSO-d₆) δ ppm 1.47 (s, 9H) 4.22 (s, 3H) 5.71 (d, J=7.72 Hz, 1H) 7.56 (dd, J=8.46, 4.04 Hz, 1H) 7.65 (s, 1H) 7.70 (d, J=7.72 Hz, 1H) 8.09 (dd, J=8.46, 1.84 Hz, 1H) 8.96 (dd, J=4.23, 1.65 Hz, 1H) 11.50 (s, 1H).

Example 2

Preparation of N-(4-(7-tert-butyl-5-(2,4-dioxo-3,4-dihydropyrimidin-1(2H)-yl)-8-methoxyquinolin-2-yl)phenyl)methanesulfonamide

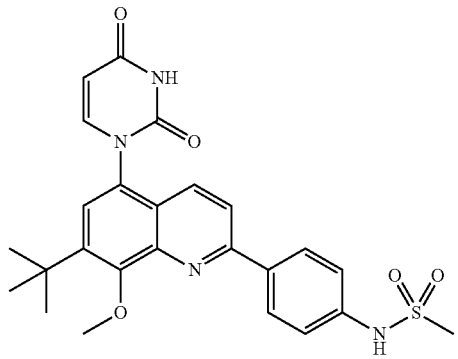 [SMILES: COc1c(C(C)(C)C)cc(-n2ccc(=O)[nH]c2=O)c2ccc(-c3ccc(NS(C)(=O)=O)cc3)nc12]

Part A. Preparation of 7-tert-butyl-5-(2,4-dioxo-3,4-dihydropyrimidin-1(2H)-yl)-8-methoxyquinoline 1-oxide.

To a 50 mL round-bottomed flask containing 1-(7-tert-butyl-8-methoxyquinolin-5-yl)pyrimidine-2,4(1H,3H)-dione (400 mg, 1.229 mmol, Example 1) in dichloromethane (10 mL) was added m-chloroperoxybenzoic acid (551 mg, 2.459 mmol), and the mixture was stirred at room temperature for 28 hours. The reaction mixture was then diluted with dichloromethane and extracted with saturated aqueous sodium bicarbonate. The aqueous layer was concentrated in vacuo. Methanol (100 mL) was added to the residue, and the solution was stirred for 30 minutes and then filtered. The filtrate was concentrated in vacuo. The crude product was purified by reverse phase (C18) column chromatography eluting with 5% to 40% acetonitrile/water containing 0.1% trifluoroacetic acid to give the title compound as a solid (101 mg, 24%).

Part B. Preparation of 1-(7-tert-butyl-2-chloro-8-methoxyquinolin-5-yl)pyrimidine-2,4(1H,3H)-dione.

To a 25 mL round-bottomed flask containing the product from Part A (61 mg, 0.179 mmol) was added phosphorus oxychloride (2 mL, 21.46 mmol). The mixture was heated at 100° C. for 10 minutes, cooled to room temperature, poured into ice-water and stirred for 10 minutes. The mixture was extracted with ethyl acetate, and the combined organic extracts were washed with water and brine, dried (sodium sulfate), filtered and concentrated in vacuo. The crude product was purified by flash column chromatography on silica gel eluting with methanol/dichloromethane (2%-5%) to give the title compound as a solid (27 mg, 42%).

Part C. Preparation of tert-butyl 4-(7-tert-butyl-5-(2,4-dioxo-3,4-dihydropyrimidin-1(2H)-yl)-8-methoxyquinolin-2-yl)phenylcarbamate.

In a 5 mL microwave tube were combined the product from Part B (25 mg, 0.069 mmol), tert-butyl-4-(4,4,5,5-tetramethyl-1,3,2-dioxaborolan-2-yl)phenylcarbamate (24.40 mg, 0.076 mmol), tetrakis(triphenylphosphine)palladium(0) (4.01 mg, 3.47 mop, 2.0 M sodium carbonate (0.139 mL, 0.278 mmol) and N,N-dimethylformamide (2 mL). The mixture was purged with nitrogen for 5 minutes, the tube was sealed and heated in a microwave (Personal Chemistry (Biotage), Emrys Creator, 300 W) at 80° C. for 30 minutes followed by heating at 100° C. for 1 hour. The mixture was partitioned between ethyl acetate and 1 M hydrochloric acid. The organic layer was washed with saturated sodium bicarbonate and brine, dried (sodium sulfate), filtered and concentrated in vacuo. The crude product was purified by flash column chromatography on silica gel eluting with methanol/dichloromethane (0%-2%) to give the title compound as a solid (19 mg, 53%).

Part D. Preparation of N-(4-(7-tert-butyl-5-(2,4-dioxo-3,4-dihydropyrimidin-1(2H)-yl)-8-methoxyquinolin-2-yl)phenyl)methanesulfonamide.

To a 10 mL round-bottomed flask containing the product from Part C (18 mg, 0.035 mmol) was added 4 M hydrochloric acid in dioxane (2 mL, 8.00 mmol). The mixture was stirred at room temperature for 1 hour, concentrated in vacuo, and azeotroped with toluene. The crude residue was dissolved in pyridine (2 mL) followed by the addition of methanesulfonyl chloride (3.26 µL, 0.042 mmol), and the mixture was stirred at room temperature for 2 hours. Methanesulfonyl chloride (3.26 µL, 0.042 mmol) was added again and the mixture was stirred at room temperature for another 2 hours followed by another addition of methanesulfonyl chloride (3.26 µL, 0.042 mmol). After an additional 2 hours of stirring, the reaction mixture was partitioned between ethyl acetate and 1 M hydrochloric acid. The organic layer was washed with saturated sodium bicarbonate and brine, dried (sodium sulfate), filtered and concentrated in vacuo. The product was triturated with methanol/dichloromethane to give the title compound as a solid (7 mg, 41%). $^1$H NMR (300 MHz, DMSO-d$_6$) δ ppm 1.48 (s, 9H) 3.07 (s, 3H) 4.34 (s, 3H) 5.72 (d, J=7.72 Hz, 1H) 7.38 (d, J=8.82 Hz, 2H) 7.59 (s, 1H) 7.74 (d, J=8.09 Hz, 1H) 8.13 (s, 2H) 8.29 (d, J=8.82 Hz, 2H) 10.10 (s, 1H) 11.52 (s, 1H).

Example 3

Preparation of N-(6-(5-(2,4-dioxo-3,4-dihydropyrimidin-1(2H)-yl)-3,3-dimethyl-2,3-dihydrobenzofuran-7-yl)naphthalen-2-yl)methanesulfonamide

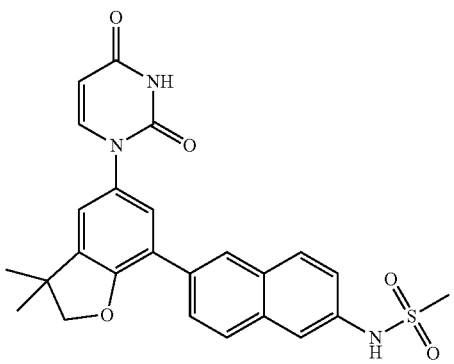

Part A. Preparation of 2-(2-hydroxy-3,5-diiodophenyl) acetic acid.

To a 250 mL round bottom flask was added 2-(2-hydroxyphenyl)acetic acid (Aldrich, 3.04 g, 20 mmol) in acetonitrile (50 mL) to give a colorless solution. N-Iodosuccinimide (9.00 g, 40.0 mmol) was added portionwise over 15 minutes to give a red/brown transparent solution that was stirred for 16 hours. The mixture was concentrated and the resulting solid was triturated in 75 mL of water and filtered to collect an orange solid that was dried under vacuum. The crude solid was recrystallized from toluene to give the title compound as a light orange powder (6.0 g, 74%).

Part B. Preparation of methyl 2-(3,5-diiodo-2-methoxyphenyl)acetate.

To a 250 mL round-bottom flask was added the product from Part A (6 g, 14.85 mmol), potassium carbonate (6.16 g, 44.6 mmol), and dimethyl sulfate (4.12 g, 32.7 mmol) in acetone (49.5 mL) to give a brown suspension. The suspension was heated at reflux for 16 hours, cooled, and concentrated. The residue was partitioned between ethyl acetate and water. The ethyl acetate layer was washed with brine, dried (Na$_2$SO$_4$) and concentrated to a brown oil that was chromatographed on a 40 g silica cartridge eluting with 3:1 hexane/ethyl acetate to give the title compound as a yellow oil (6.0 g, 94%).

Part C. Preparation of methyl 2-(3,5-diiodo-2-methoxyphenyl)-2-methylpropanoate.

To a 100 mL round-bottom flask under nitrogen was added the product from Part B (1.728 g, 4 mmol) in anhydrous tetrahydrofuran (20 mL) and hexamethylphosphoramide (2 lA) to give a colorless solution. Methyl iodide (1.251 mL, 20.00 mmol) was added and the solution was cooled to −40° C. Potassium t-butoxide (12.00 mL, 12.00 mmol) was added dropwise and the mixture was stirred at −40 to −20° C. for 30 minutes and quenched with 1 M HCl to a pH of 1. The mixture was extracted 3×40 ml with ethyl acetate. The extracts were combined, washed with brine, dried (Na$_2$SO$_4$) and concentrated. The crude product was flash chromatographed on a 40 g ISCO silica cartridge eluting with 9:1 hexane/ethyl acetate to give the title compound as a yellow oil (1.63 g, 89%).

Part D. Preparation of 2-(3,5-diiodo-2-methoxyphenyl)-2-methylpropanoic acid.

A suspension of the product from Part C (2.63 g, 5.72 mmol) in methanol (40 mL) and tetrahydrofuran (40 mL) was treated with 4.0 M sodium hydroxide (28 mL, 112 mmol) and heated at 80° C. for 48 hours. The organic solvent was evaporated and the remaining aqueous solution was acidified with 1 M HCl producing a solid that was collected by filtration, washed with water and dried to give the title compound (2.46 g, 96%).

Part E. Preparation of 2-(3,5-diiodo-2-methoxyphenyl)-2-methylpropan-1-ol.

A solution of the product from Part D (1.00 g, 2.242 mmol) in tetrahydrofuran (40 mL) was treated dropwise with borane tetrahydrofuran complex solution (1.0 M, 20 mL, 20 mmol) and then heated at 50° C. for 24 hours, The mixture was treated with methanol (20 mL), refluxed for 30 minutes and concentrated. The resulting residue was washed with water and brine, dried with sodium sulfate, filtered and evaporated. The residue was chromatographed on silica gel eluting with hexane/ethyl acetate (4:1) to give the title compound (810 mg, 84%).

Part F. Preparation of 5,7-diiodo-3,3-dimethyl-2,3-dihydrobenzofuran

Into a 25 mL round-bottomed flask was added the product from Part E, (259 mg, 0.6 mmol) in dichloromethane (5 mL). Diethylaminosulfur trifluoride (0.079 mL, 0.600 mmol) was added at −78° C. under nitrogen and the mixture was warmed to room temperature followed by stirring for 1 hour. Then the reaction mixture was treated with 5% aqueous sodium carbonate. The mixture was extracted with dichloromethane, dried (sodium sulfate), filtered and concentrated in vacuo. The crude product was purified by flash column chromatography on silica gel eluting with 5% ethyl acetate/hexane to give the title compound as an oil (150 mg, 62%).

Part G. Preparation of 1-(7-iodo-3,3-dimethyl-2,3-dihydrobenzofuran-5-yl)pyrimidine-2,4(1H,3H)-dione.

In a 20 mL microwave tube under a nitrogen flush was added the product from Part F (0.14 g, 0.350 mmol), 1H-pyrimidine-2,4-dione (0.047 g, 0.420 mmol), and potassium phosphate tribasic (0.156 g, 0.735 mmol) in dimethyl sulfoxide (1.5 mL) to give a colorless suspension. N-(2-Cyanophenyl)picolinamide (0.016 g, 0.070 mmol) was added and the mixture was sparged with nitrogen for 10 minutes. Copper(I) iodide (6.67 mg, 0.035 mmol) was added and the mixture was sparged once again for 10 minutes, placed under nitrogen and heated at 60° C. for 18 hours. The mixture was cooled and partitioned between ethyl acetate and water, adjusting the pH to 1 with hydrochloric acid (1 M). The aqueous layer was extracted with ethyl acetate. The organic washes were combined, washed with water and saturated sodium bicarbonate and brine, dried (sodium sulfate), stirred with 3-mercaptopropyl functionalized silica gel for 1 hour, filtered and concentrated in vacuo. The crude product was purified by chromatography on an ISCO 12 g silica get cartridge eluting with 2% methanol/dichloromethane to give the title compound as a white powder (33 mg, 24%).

Part H. Preparation of 6-bromo-2-naphthoic acid.

A solution of methyl 6-bromo-2-naphthoate (7.70 g, 29.0 mmol) in 2:1 tetrahydrofuran:water (150 mL) was treated with lithium hydroxide hydrate (2.44 g, 58.1 mmol) followed by stirring at room temperature for 48 hours. The mixture was concentrated under vacuum, diluted with water and cooled to 0° C. The mixture was acidified to pH3 with 4 N HCl. Solids were collected by filtration, dissolved in toluene-ethyl acetate (ca. 2 L) and washed with brine. The organic layer was dried over $Na_2SO_4$, filtered and concentrated under vacuum. The brown solid was triturated with ether, collected by filtration, and dried under vacuum to give the title compound as a nearly white solid (5.07 g, 70%).

Part I. Preparation of 6-bromonaphthalen-2-amine.

A solution of the product Part H (5.07 g, 20.19 mmol) and triethylamine (4.22 mL, 3.07 g, 30.3 mmol) in dry N,N-dimethylformamide (155 mL) was treated with the diphenylphosphoroyl azide (6.55 mL, 8.34 g, 30.3 mmol) followed by stirring at room temperature for 3 hours. The solution was then treated with water (20 mL) followed by warming at 100° C. for 1 hour. The solution was cooled and the flask fitted with a short-path distillation head and the N,N-dimethylformamide was removed by distillation under high vacuum. The solid residue was dissolved in ethyl acetate and washed with saturated sodium bicarbonate solution. The organic layer was filtered through diatomaceous earth, and the filtrate was washed with water (3×) and then with brine. The organic layer was dried over $Na_2SO_4$, filtered and concentrated under vacuum to give the title compound as a beige solid (4.48 g, 100%).

Part J. Preparation of N-(6-bromonaphthalen-2-yl)methanesulfonamide.

A solution of the product from Part I (4.48 g, 20.17 mmol) in pyridine (100 mL) was treated drop wise with methanesulfonyl chloride (1.97 mL, 2.89 g, 25.2 mmol) followed by stirring at room temperature for 1 hour. The reaction mixture was diluted with toluene and concentrated under vacuum twice. The residue was extracted with ethyl acetate and washed with water, 1 M citric acid and brine. The organic layer was treated with Darco G-60, dried over $Na_2SO_4$, filtered through diatomaceous earth and concentrated under vacuum. The solid was triturated with ether-hexane, collected by filtration and dried under vacuum to give the title compound as a faint pink solid (3.32 g, 55%).

Part K. Preparation of N-(6-(4,4,5,5-tetramethyl-1,3,2-dioxaborolan-2-yl)naphthalen-2-yl)methanesulfonamide.

A mixture of the product from Part J (1.00 g, 3.33 mmol), bis(pincolato)diboron (1.27 g, 5.00 mmol), potassium acetate (0.98 g, 9.99 mmol) and Combiphos Pd6 (84 mg, 0.17 mmol) in toluene (22 mL) was heated at reflux for 3 hours. The reaction mixture was cooled and diluted with ethyl acetate and water. The mixture was treated with Darco G-60 and filtered through diatomaceous earth. The filtrate was washed with water and brine, dried over $Na_2SO_4$, filtered and concentrated under vacuum. The oil residue was dissolved in ether and precipitated by the addition of hexanes. The product was collected by filtration and washed with hexanes. Evaporation of the filtrate and purification of the residue by silica gel column chromatography eluting with 10-60% ethyl acetate/hexanes provided additional product. The title compound obtained from both the crystallization and the chromatography was isolated as a white solid (927 mg, 80%).

Part L. Preparation of N-(6-(5-(2,4-dioxo-3,4-dihydropyrimidin-1(2H)-yl)-3,3-dimethyl-2,3-dihydrobenzofuran-7-yl)naphthalen-2-yl)methanesulfonamide.

In a 5 mL microwave tube was added the product from Part G (0.03 g, 0.078 mmol), the product from Part K (0.027 g, 0.078 mmol), potassium phosphate tribasic (0.033 g, 0.156 mmol) and 1,1'-bis(di-tert-butylphosphino)ferrocene palladium dichloride (2.54 mg, 3.90 μmol) in tetrahydrofuran (3 mL) and water (1 mL). The mixture was sparged for 10 minutes with nitrogen, sealed and heated at 50° C. for 4 hours. The mixture was cooled, diluted with ethyl acetate, washed with 1 M hydrochloric acid and saturated sodium bicarbonate and brine, dried (sodium sulfate) and treated simultaneously with mercaptopropyl silica gel, filtered and concentrated in vacuo. The crude product was purified on a 12 g Isco silica gel cartridge eluting with 2% methanol/dichloromethane followed by a final purification by C18 reverse phase chromatography (acetonitrile/0.1% trifluoroacetic acid in water) to give the title compound as a single peak on HPLC that has an NMR indicative of a 2:1 mix of conformational isomers (10 mg, 26%). $^1$H NMR (300 MHz, DMSO-$d_6$) δ ppm 1.38 (s, 6H) 3.08 (s, 3H) 4.40 (s, 2H) 5.66 (dd, J=8.09, 2.21 Hz, 1H) 7.24-8.31 (m, 9H) 10.03 (s, 1H) 11.42 (d, J=2.21 Hz, 1H).

Example 4

Preparation of 1-(4,4-dimethyl-2-oxo-3,4-dihydro-2H-benzo[h]chromen-6-yl)dihydropyrimidine-2,4(1H,3H)-dione

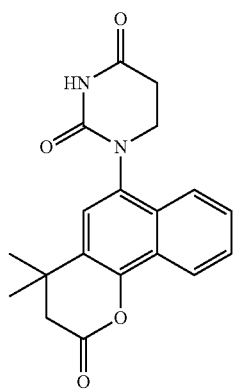 [SMILES: CC1(C)CC(=O)Oc2c1cc(N1CCC(=O)NC1=O)c1ccccc21]

Part A. Preparation of 4,4-dimethyl-3,4-dihydro-2H-benzo[h]chromen-2-one.

To a 100 mL round bottomed flask was added 1-naphthol (10.0 g, 69.35 mmol), 3,3-dimethylacrylic acid (7.29 g, 72.82 mmol), and methanesulfonic acid (50 mL). The mixture was heated at 70° C. for 3.5 hours, cooled to room temperature, poured into water (500 mL), and stirred for 1 hour. The solution was extracted with ethyl acetate and the resultant organic extracts were combined and washed with water and 1 N sodium hydroxide, dried (magnesium sulfate), filtered and concentrated in vacuo. The crude product was purified by flash column chromatography on silica gel eluting with 10% ethyl acetate/hexane to give the title compound as a light yellow solid (11.86 g, 76%).

Part B. Preparation of 4,4-dimethyl-6-nitro-3,4-dihydro-2H-benzo[h]chromen-2-one.

To a 50 mL round bottomed flask was added the product from Part A (5.0 g, 22.12 mmol), acetic acid (7 mL) and concentrated sulfuric acid (10 mL). The mixture was cooled to 0° C., and then a mixture of concentrated sulfuric acid (2 mL) and concentrated nitric acid (2 mL) was added dropwise over 15 minutes. The resultant solution was stirred at room temperature for 0.5 hour, poured into ice water, and extracted with ethyl acetate. The resultant organic extracts were combined and washed with saturated sodium bicarbonate, dried (magnesium sulfate), filtered and concentrated in vacuo. The crude product was purified by flash column chromatography on silica gel eluting with 25% ethyl acetate/hexane to provide the title compound as a light yellow solid (1.66 g, 28%).

Part C. Preparation of 6-amino-4,4-dimethyl-3,4-dihydro-2H-benzo[h]chromen-2-one.

To a 50 mL round bottomed flask was added the product from Part B (500 mg, 1.84 mmol), iron (514 mg, 9.22 mmol) and ammonium chloride (148 mg, 1.5 mmol). To the mixture was added tetrahydrofuran (10 mL), water (3 mL) and ethanol (10 mL), and the resultant solution was heated to 90° C. for 2 hours. The mixture was filtered through a pad of diatomaceous earth and rinsed with methanol. The filtrate was concentrated in vacuo. The crude product was partitioned between water and ethyl acetate. The combined organic extracts were dried (magnesium sulfate), filtered and concentrated in vacuo. The crude product was purified by flash column chromatography on silica gel eluting with 25% ethyl acetate/hexanes to provide the title compound as an orange oil (420 mg, 94%).

Part D. Preparation of 3-(4,4-dimethyl-2-oxo-3,4-dihydro-2H-benzo[h]chromen-6-ylamino)propanoic acid.

To a 10 mL round bottomed flask was added the product from Part C (85 mg, 0.353 mmol), toluene (5 mL) and acrylic acid (0.027 mL, 0.388 mmol). The mixture was heated to reflux for 56 hours, cooled to room temperature and concentrated in vacuo. The crude product was purified by flash column chromatography on silica gel eluting with methanol/dichloromethane (0-20%) to provide the title compound as a reddish brown solid (33 mg, 30%).

Part E. Preparation of 1-(4,4-dimethyl-2-oxo-3,4-dihydro-2H-benzo[h]chromen-6-yl)dihydropyrimidine-2,4(1H,3H)-dione.

To a 10 mL round bottomed flask was added the product from Part D (30 mg, 0.096 mmol) and urea (12.7 mg, 0.211 mmol). To the mixture was added acetic acid (3 mL) and concentrated hydrochloric acid (0.5 mL). The resultant solution was heated to 110° C. for 5 hours, cooled to room temperature and then water was added. The mixture was extracted with dichloromethane, the combined organic extracts dried (magnesium sulfate), filtered and concentrated in vacuo. The crude product was purified by flash column chromatography on silica gel eluting with methanol/dichloromethane (0-10%) to provide the title compound (11 mg, 34%). $^1$H NMR (300 MHz, DMSO-$d_6$) δ ppm 1.55 (s, 6H), 2.73 (m, 1H), 2.94 (m, 3H), 3.62 (m, 1H), 3.89 (m, 1H), 7.65 (m, 1H), 7.72 (m, 2H), 7.93 (d, J=8.1 Hz, 1H), 8.32 (d, J=8.1 Hz, 1H), 10.43 (s, 1H).

Example 5

Preparation of N-(4-(8-tert-butyl-6-(2,4-dioxo-3,4-dihydropyrimidin-1(2H)-yl)quinazolin-4-ylamino)phenyl)methanesulfonamide

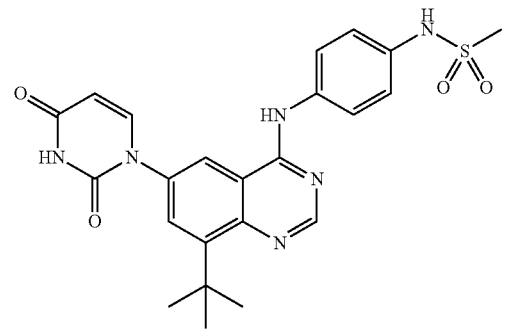 [SMILES: CC(C)(C)c1cc(-n2ccc(=O)[nH]c2=O)cc2c(Nc3ccc(NS(C)(=O)=O)cc3)ncnc12]

Part A. Preparation of N-(2-tert-butylphenyl)-2-(hydroxyimino)acetamide.

To a boiling solution of 2-tert-butylaniline (1.0 g, 6.70 mmol), hydroxylamine hydrochloride (1.513 g, 21.78 mmol), and sodium sulfate (6.2 g, 43.6 mmol) in 1 N hydrochloric acid (6.7 mL) and water (20 mL) was added a hot solution of 2,2,2-trichloro-1-ethoxyethanol (1.556 g, 8.04 mmol) in water (20 mL). The mixture was refluxed for 40 minutes, cooled to room temperature, and extracted with diethyl ether. The combined ethereal extracts were washed with brine, dried (magnesium sulfate), filtered, and concentrated in vacuo. The residue was co-evaporated with diethyl ether/benzene to give a brown solid which was purified by flash column chromatography on silica gel eluting with 3% methanol/dichloromethane to give the title compound as a dark yellow solid (600 mg, 41%).

Part B. Preparation of 7-tert-butylisatin

To a stirred solution of concentrated sulfuric acid (9 mL) and water (0.9 mL) at 65° C. was added the product of Part A (2.112 g, 9.59 mmol) over 10 minutes with formation of a deep purple color. The reaction was heated to 80° C. and maintained at this temperature for 10 minutes. Then the reaction mixture was cooled to room temperature, added to ice, and extracted with diethyl ether. The combined ethereal extracts were washed with water and brine, dried (magnesium sulfate), filtered, and concentrated in vacuo to give the title compound as an orange solid (1.825 g, 94%).

Part C. Preparation of 7-tert-butyl-5-nitroisatin.

A solution of potassium nitrate (1.04 g, 10.29 mmol) and concentrated sulfuric acid (25 mL) at 0° C. was treated with a solution of the product of Part B (2.092 g, 10.3 mmol) in concentrated sulfuric acid (25 mL) over 1 hour, then stirring was continued at 0° C. for 1 hour. The reaction mixture was poured onto ice and extracted with ethyl acetate. The combined organic extracts were washed with brine, dried (magnesium sulfate), filtered, and concentrated in vacuo to give the title product as a dark yellow solid (2.55 g, 100%).

Part D. Preparation of 2-amino-3-tert-butyl-5-nitrobenzoic acid.

A mixture of the product of Part C (1.0 g, 4.03 mmol) in 1.016 N sodium hydroxide (8.8 mL, 8.94 mmol) and water (5 mL) was treated with 30% hydrogen peroxide solution (0.93 mL, 9.06 mmol) dropwise over 15 minutes at room temperature, and the mixture was stirred at room temperature for 1 hour. The reaction mixture was diluted with water (100 mL) and the pH was adjusted to 3 with 1 N hydrochloric acid. The resultant mixture was extracted with ethyl acetate. The combined organic extracts were washed with brine, dried (magnesium sulfate), filtered, and concentrated in vacuo to give the title compound as a yellow solid (840 mg, 88%).

Part E. Preparation of 8-tert-butyl-6-nitroquinazolin-4(3H)-one.

A mixture of the product of Part D (350 mg, 1.469 mmol) and formamide (2 mL, 50.2 mmol) in a 5-mL microwave tube was heated in a microwave (Personal Chemistry (Biotage), Emrys Creator, 300 W) at 180° C. for 2.5 hours with stirring. The solvent was removed in vacuo and the residue dried further on a vacuum pump. The crude product was purified by flash column chromatography on silica gel eluting with 3% methanol/dichloromethane to afford the title compound as a yellow solid (189 mg, 52%).

Part F. Preparation of 8-tert-butyl-4-chloro-6-nitroquinazoline.

A mixture of the product of Part E (200 mg, 0.809 mmol) and phosphorus oxychloride (3 mL, 32.2 mmol) was heated under a nitrogen atmosphere at reflux for 30 minutes. The reaction was cooled to room temperature and dried further on a vacuum pump. The residue was taken up in dichloromethane (50 mL), washed with saturated sodium bicarbonate and water and brine, dried (magnesium sulfate), filtered, and concentrated in vacuo. Drying the resulting brown oil in vacuo afforded the title compound as a crystalline tan solid (213 mg, 99%).

Part G. Preparation of N-(4-(8-tert-butyl-6-nitroquinazolin-4-ylamino)phenyl)methanesulfonamide.

N-(4-Aminophenyl)methanesulfonamide hydrochloride (178 mg, 0.798 mmol) was taken up in 2-propanol (8 mL) and treated with triethylamine (0.334 mL, 2.394 mmol) and a solution of the product of Part F (212 mg, 0.798 mmol) in dichloromethane (2 mL) at room temperature. Then the resultant reaction mixture was heated at reflux for 18 hours. After being cooled to room temperature, the reaction mixture was concentrated in vacuo. The amber oil was purified by flash column chromatography on silica gel eluting with 2.5% methanol/dichloromethane to afford the title compound as a yellow solid (286 mg, 86%).

Part H. Preparation of N-(4-(6-amino-8-tert-butylquinazolin-4-ylamino)phenyl)methanesulfonamide.

A solution of the product of Part G (296 mg, 0.712 mmol) in tetrahydrofuran (3 mL) and absolute ethanol (3 mL) was treated with a solution of ammonium chloride (250 mg, 4.67 mmol) in water (1.5 mL) and iron powder (245 mg, 4.38 mmol). The resulting mixture was heated at 80° C. for 1 hour. After cooling to room temperature, the reaction mixture was diluted with ethyl acetate, washed with water and brine, dried (magnesium sulfate), filtered, and concentrated in vacuo to afford the title compound (160 mg, 58%).

Part I. Preparation of (E)-N-(8-tert-butyl-4-(4-(methylsulfonamido)phenylamino)quinazolin-6-ylcarbamoyl)-3-methoxyacrylamide.

A solution of the product of Pert H (50 mg, 0.13 mmol) in anhydrous N,N-dimethylformamide (1 mL) in a flame-dried flask under a nitrogen atmosphere was treated with freshly activated 4 Å molecular sieve powder and cooled to −25° C. A solution of 0.55 M(E)-3-methoxyacryloyl isocyanate in benzene (0.472 mL, 0.259 mmol), freshly prepared according to the procedure in *Synthesis* (2) 239 (2001), was added dropwise via a gas-tight syringe to the reaction. The reaction mixture was then warmed to room temperature and stirred for 6 hours. The molecular sieve powder was removed by filtration. The collected sieve powder was thoroughly washed with ethanol and toluene. The combined filtrate and washings were concentrated in vacuo. The crude product was purified by flash column chromatography on silica gel eluting with 6% methanol/dichloromethane to give the title compound as a yellow solid (63 mg, 93%).

Part J. Preparation of N-(4-(8-tert-butyl-6-(2,4-dioxo-3,4-dihydropyrimidin-1(2H)-yl)quinazolin-4-ylamino)phenyl) methanesulfonamide.

A solution of the product of Part I (30 mg, 0.059 mmol) in 1:1:0.1 (v/v/v) ethanol/water/concentrated sulfuric acid (2 mL) was heated from room temperature to 100° C. and stirred for 20 minutes. The reaction mixture was cooled to room temperature, concentrated in vacuo, and the residue azeotroped with toluene to give a golden oil. The oil was taken up in water (10 mL), and the pH was adjusted to 3 with 6 N sodium hydroxide. The mixture was extracted with ethyl acetate, The combined organic extracts were washed with brine, dried (magnesium sulfate), filtered, and concentrated in vacuo to afford the title compound as a light yellow solid (24.7 mg, 81%). $^1$H NMR (300 MHz, DMSO-d$_6$) δ ppm 1.60 (s, 9H), 2.99 (s, 3H), 5.78 (d, J=7.72 Hz, 1H), 7.24 (d, J=8.82 Hz, 2H), 7.75 (d, J=8.82 Hz, 2H), 7.78 (d, J=1.84 Hz, 1H), 7.90 (d, J=7.72 Hz, 1H), 8.48 (d, J=2.21 Hz, 1H), 8.67 (s, 1H), 9.65 (br s, 1H), 9.75 (s, 1H), 11.58 (br s, 1H).

Example 6

Preparation of N-(4-(8-tert-butyl-6-(2,4-dioxotetrahydropyrimidin-1(2H)-yl)quinazolin-4-ylamino) phenyl)methanesulfonamide

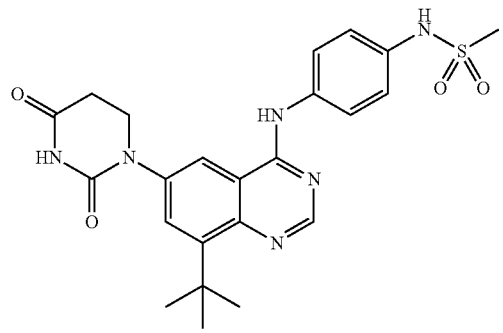 [SMILES: CC(C)(C)c1cc(N2CCC(=O)NC2=O)cc2c(Nc3ccc(NS(C)(=O)=O)cc3)ncnc12]

A nitrogen-purged flask was charged with the product of Example 5 (22 mg, 0.046 mmol), anhydrous N,N-dimethylformamide (2 mL), anhydrous methanol (2 mL), and 5% rhodium on alumina (22 mg). The system was evacuated and filled with hydrogen from a balloon. The evacuation/fill cycle was repeated three times. The reaction mixture was stirred vigorously at room temperature for 4.5 hours (reaction ~30% complete). Additional 5% rhodium on alumina (22 mg) was added, and the reaction mixture was stirred at room temperature for another 22 hours under hydrogen (1 atm). The reaction was vacuum filtered through a pad of diatomaceous earth. The pad and collected catalyst were thoroughly washed with N,N-dimethylformamide. The filtrate and washes were concentrated in vacuo and dried further on a vacuum pump. Trituration of the resulting solid with 10% methanol/dichloromethane afforded the title compound as an off-white solid (16 mg, 67%). $^1$H NMR (300 MHz, DMSO-$d_6$) δ ppm 1.59 (s, 9H), 2.79 (t, J=6.62 Hz, 2H), 2.98 (s, 3H), 3.95 (t, J=6.62 Hz, 2H), 7.23 (d, J=9.19 Hz, 2H), 7.71 (d, J=8.82 Hz, 2H), 7.78 (d, J=1.84 Hz, 1H), 8.27 (d, J=1.84 Hz, 1H), 8.60 (s, 1H), 9.65 (s, 1H), 9.68 (s, 1H), 10.51 (s, 1H).

Example 7

Preparation of N-((5-(8-tert-butyl-6-(2,4-dioxo-3,4-dihydropyrimidin-1(2H)-yl)quinazolin-4-ylamino)thiophen-3-yl)methyl)methanesulfonamide

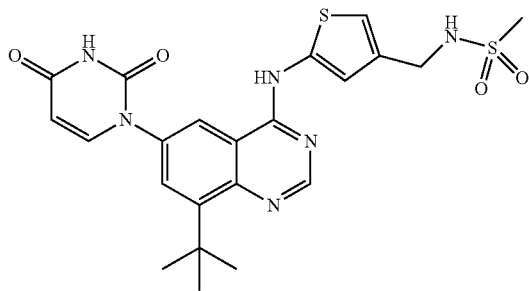 [SMILES: CC(C)(C)c1cc(-n2ccc(=O)[nH]c2=O)cc2c(Nc3cc(CNS(C)(=O)=O)cs3)ncnc12]

Part A. Preparation of (5-nitrothiophen-3-yl)methanol.

In a 250 mL round-bottomed flask was added 5-nitrothiophene-3-carboxylic acid (Alfa, 693 mg, 4.0 mmol) in tetrahydrofuran (20 mL) to give a colorless solution. Borane tetrahydrofuran complex solution (8.0 mL, 1 M) was added at a fast drip and the resulting mixture was heated at gentle reflux for 45 minutes, cooled and then poured into ice water. The pH of the mixture was adjusted to 3 with 1 M HCl and extracted into ethyl acetate. The ethyl acetate layer was washed with water and brine. The organic layer was dried over anhydrous $Na_2SO_4$, filtered to remove drying agent and concentrated in vacuo leaving a yellow residue. The residue was purified by silica gel chromatography eluting with 2% $CH_3OH/CH_2Cl_2$ to give a yellow oil, (0.61 g, 96%).

Part B. Preparation of 4-(chloromethyl)-2-nitrothiophene.

To a 25 mL round-bottomed flask was added thionyl chloride (0.330 mL, 4.52 mmol) to tetrahydrofuran (10 mL) to give a colorless solution. N,N-Dimethylformamide (0.356 mL, 4.60 mmol) was added and the clear solution was heated at 40° C. for 2 hours and concentrated. The residue was redissolved in tetrahydrofuran (5 mL) and the compound prepared in Part A (600 mg, 3.77 mmol) was added dropwise as a solution in tetrahydrofuran (5 mL). The mixture was stirred for 1 hour and quenched with brine. The aqueous layer was back extracted with ethyl acetate (2×15 mL). The combined organic layers were washed with water and brine. The organic layer was dried over anhydrous $Na_2SO_4$, the drying reagent was removed by filtration, and the filtrate was concentrated in vacuo to give an oily residue. The residue was purified by silica gel chromatography eluting with 5:1 hexane/ethyl acetate to give the title compound as a yellow oil, (0.39 g, 58%).

Part C. Preparation of tert-butyl methylsulfonyl((5-nitrothiophen-3-yl)methyl)carbamate.

In a 50 mL round-bottomed flask was added the compound prepared in Part B (390 mg, 2.196 mmol), tert-butyl methylsulfonylcarbamate (514 mg, 2.64 mmol), and potassium carbonate (303 mg, 2.196 mmol) in dimethylacetamide (10 mL) to give a brown suspension. The suspension was heated at 50° C. for 16 hours under nitrogen. The reaction mixture was cooled and partitioned between ethyl acetate and water. The ethyl acetate layer was washed with water and brine. The organic layer was dried over anhydrous $Na_2SO_4$, filtered and concentrated in vacuo leaving a brown residue. The residue was purified by silica gel chromatography eluting with 1:1 hexane/ethyl acetate and the title compound was obtained as a tan solid (0.55 g, 74%).

Part D. Preparation of N-((5-nitrothiophen-3-yl)methyl)methanesulfonamide.

In a 50 mL round-bottomed flask was added the product from Part C (1.009 g, 3.0 mmol) to a solution of 4 M HCl in dioxane (10 mL). The mixture was stirred at room temperature for 5 hours. The solvent was evaporated and the residue was partitioned between water and ethyl acetate. The organic layer was dried with sodium sulfate, filtered and evaporated to give the title compound as a yellow oil (0.691 g, 97%); MS (DCl+) m/z 254 $(M+NH_4)^+$.

Part E. Preparation of N-((5-aminothiophen-3-yl)methyl)methanesulfonamide.

The product from Part D (277 mg, 1.172 mmol) was dissolved in a mixture of tetrahydrofuran (10 mL) and ethanol (10 mL) under nitrogen. Iron powder (327 mg, 5.86 mmol) and a solution of ammonium chloride (94 mg, 1.759 mmol) in water (5.00 mL) were added, and the resultant mixture was heated at 90° C. for 1 hour. The reaction mixture was cooled to room temperature, and the reaction mixture was partitioned between water (50 mL) and ethyl acetate (100 mL). The separated organic layer was washed with water (2×50 mL) and brine. The organic layer was dried over anhydrous magnesium sulfate, filtered, and concentrated in vacuo. The residue was purified by flash chromatography on silica gel eluting with 6% $CH_3OH/CH_2Cl_2$ to afford the product as a goldenrod-colored solid (105 mg, 43%).

Part F. Preparation of N-((5-(8-tert-butyl-6-nitroquinazolin-4-ylamino)thiophen-3-yl)methyl)methanesulfonamide.

A solution of the compound prepared in Part E (88.3 mg, 0.428 mmol) in 2-propanol (2 mL) was treated with triethylamine (0.18 mL, 1.284 mmol) and a solution of the product of Example 5 Part F (114 mg, 0.428 mmol) in dichloromethane (1 mL) at room temperature. The resultant reaction mixture was then heated at 100° C. for 18 hours, cooled to room temperature, concentrated in vacuo and further dried on a vacuum pump. The amber colored oil was purified by flash column chromatography on silica gel eluting with 3% methanol/dichloromethane to afford the title compound as an orange solid (97 mg, 52%).

Part G. Preparation of N-((5-(6-amino-8-tert-butylquinazolin-4-ylamino)thiophen-3-yl)methyl)methanesulfonamide.

A solution of the product of Part F (93 mg, 0.214 mmol) in tetrahydrofuran (2 mL) and ethanol (2 mL) was treated with a solution of ammonium chloride (17.13 mg, 0.32 mmol) in water (1 mL) and iron powder (59.6 mg, 1.068 mmol). The mixture was heated at 80° C. for 1 hour and then cooled to room temperature. The reaction mixture was then diluted with ethyl acetate, washed with water and brine, dried (magnesium sulfate), filtered, and concentrated in vacuo. The crude product was purified by flash column chromatography on silica gel eluting with 5% methanol/dichloromethane to give the title compound as a dark yellow solid (79 mg, 91%).

Part H. Preparation of (E)-N-(8-tert-butyl-4-(4-(methylsulfonamidomethyl)thiophen-2-ylamino)quinazolin-6-yl-carbamoyl)-3-methoxyacrylamide.

The product from Part G (77 mg, 0.19 mmol) was reacted following the procedure for Example 5 Part I and purified by flash column chromatography on silica gel eluting with 5% methanol/dichloromethane to give the title compound as a yellow solid (68 mg, 67%).

Part I. Preparation of N-((5-(8-tert-butyl-6-(2,4-dioxo-3,4-dihydropyrimidin-1(2H)-yl)quinazolin-4-ylamino)thiophen-3-yl)methyl)methanesulfonamide.

The product from Part H (63 mg, 0.118 mmol) was reacted following the procedure for Example 5 Part J. The crude product residue was triturated with a small volume of 4% methanol/dichloromethane to give the title compound as a tan solid (33 mg, 56%). $^1$H NMR (300 MHz, DMSO-d$_6$) δ ppm 1.61 (s, 9H), 2.87 (s, 3H), 4.11 (d, J=5.88 Hz, 2H), 5.79 (d, J=8.09 Hz, 1H), 6.92 (s, 1H), 7.05 (s, 1H), 7.54 (t, J=6.25 Hz, 1H), 7.79 (s, 1H), 7.90 (d, J=7.72 Hz, 1H), 8.50 (s, 1H), 8.80 (s, 11-1), 11.02 (s, 1H), 11.59 (s, 11-1H).

HCV Polymerase Inhibition Assay

Either two-fold serial dilutions (fractional inhibition assay) or a narrower range of dilutions spanning the IC$_{50}$ of the inhibitor (tight binding assay) of the inhibitors were incubated with 20 mM Tris-Cl pH 7.4, 2 mM MnCl$_2$, 1 mM dithiothreitol, 1 mM ethylene diamine tetraacetic acid (EDTA), 60 to 125 µM GTP and 20 to 50 nM Δ21 NS5B (HCV Strain 1B (BK, Genbank accession number M58335, or H77, Genbank accession number AF011751)) for 15 minutes at room temperature. The reaction was initiated by the addition of 20 µM CTP, 20 µM ATP, 1 µM $^3$H-UTP (10 mCi/µmol), 5 nM template RNA and 0.1 U/µL RNase inhibitor (RNasin, Promega), and allowed to proceed for 2 to 4 hours at room temperature. Reaction volume was 50 µL. The reaction was terminated by the addition of 1 volume of 4 mM spermine in 10 mM Tris-Cl pH 8.0, 1 mM EDTA. After incubation for at least 15 minutes at room temperature, the precipitated RNA was captured by filtering through a GF/B filter (Millipore) in a 96 well format. The filter plate was washed three times with 200 µL each of 2 mM spermine, 10 mM Tris-Cl pH 8.0, 1 mM EDTA, and 2 times with ethanol. After air-drying, 30 µL of Microscint 20 scintillation cocktail (Packard) was added to each well, and the retained cpm were determined by scintillation counting. IC$_{50}$ values were calculated by a two-variable nonlinear regression equation using an uninhibited control and a fully inhibited control sample to determine the minimum and maximum for the curve. Tight-binding assays were performed on those compounds exhibiting IC$_{50}$ values less than 0.005 µM in the fractional inhibition assay in order to more precisely measure the IC$_{50}$ values. Retained cpm were plotted vs. inhibitor concentration and fit to equation 1 using non-linear regression (ref. 1) to obtain the IC$_{50}$ values:

$$\text{Retained cpm} = A[sqrt\{(IC_{50}+I_t-E_t)^2+4*IC_{50}*E_t\}-(IC_{50}+I_t-E_t)] \quad \text{(equation 1)}$$

where A=Vmax[S]/2(Km+[S]); It=total inhibitor concentration and Et=total active concentration of enzyme.

Ref. Morrison, J. F. and S. R. Stone. 1985. Approaches to the study and analysis of the inhibition of enzymes by slow- and tight-binding inhibitors. Comments Mol. Cell. Biophys. 2: 347-368.

The sequence of the template RNA used was: 5'-GGGC-GAAUUG GGCCCUCUAG AUGCAUGCUC GAGCGGC-CGC CAGUGUGAUG GAUAUCUGCA GAAUUCGCCC UUGGUGGCUC CAUCUUAGCC CUAGUCACGG CUAGCUGUGA AAGGUCCGUG AGCCGCUUGA CUG-CAGAGAG UGCUGAUACU GGCCUCUCUG CAGAUCAAGUC-3' (SEQ ID NO: 1).

When tested by the above method, the compounds of this invention inhibit HCV polymerase 1A and/or 1B. The legend in the table below is as follows: A—IC$_{50}$≤0.01 µM; B—0.1 µM≥IC$_{50}$>0.01 µM; C—1 µM≥IC$_{50}$>0.1 µM; and D—IC$_{50}$>1 µM; ND—not determined.

TABLE IC$_{50}$

| compound | 1a | 1b | compound | 1a | 1b |
|---|---|---|---|---|---|
| 1 | B | B | 2 | D | D |
| 3 | A | B | 4 | D | C |
| 5 | B | B | 6 | B | B |
| 7 | B | A | | | |

HCV Polymerase Replicon Assay

Two stable subgenomic replicon cell lines were used for compound characterization in cell culture: one derived from genotype 1a-H77 and one derived from genotype 1b-Con1 (obtained from Apath, LLC, St. Louis, Mo.). All replicon constructs were bicistronic subgenomic replicons similar to those described by S$_{CIENCE}$ 285:110-3 (1999). The genotype 1a replicon construct contains NS3-NS5B coding region derived from the H77 strain of HCV (1a-H77) (J. V$_{IROL.}$ 77:3181-90 (2003)). The replicon also has a firefly luciferase reporter and a neomycin phosphotransferase (Neo) selectable marker. These two coding regions, separated by the FMDV 2a protease, comprise the first cistron of the bicistronic replicon construct, with the second cistron containing the NS3-NS5B coding region with addition of adaptive mutations E1202G, K1691R, K2040R and S2204I. The 1b-Con1 replicon construct is identical to the 1a-H77 replicon, except that the NS3-NS5B coding region was derived from the 1b-Con1 strain, and the adaptive mutations are E1202G, T12801 and 522041. Replicon cell lines were maintained in Dulbecco's modified Eagles medium (DMEM) containing 10% (v/v) fetal bovine serum (PBS), 100 IU/ml, penicillin, 100 mg/mL streptomycin (Invitrogen), and 200 mg/mL G418 (Invitrogen).

The inhibitory effects of compounds on HCV replication were determined by measuring activity of the luciferase reporter gene. Briefly, replicon-containing cells were seeded into 96 well plates at a density of 5000 cells per well in 100 µl DMEM containing 5% FBS. 16-24 hours later, the compounds were diluted in dimethyl sulfoxide (DMSO) to generate a 200× stock in a series of eight half-log dilutions. The dilution series was then further diluted 100-fold in the medium containing 5% FBS. Medium with the inhibitor was added to the overnight cell culture plates already containing 100 µL of DMEM with 5% FBS. In assays measuring inhibitory activity in the presence of human plasma, the medium from the overnight cell culture plates was replaced with DMEM containing 40% human plasma and 5% FBS. The cells were incubated for three days in the tissue culture incubators and were then lysed for RNA extraction. For the luciferase assay, 30 µL of Passive Lysis buffer (Promega) was added to each well, and then the plates were incubated for 15 minutes with rocking to lyse the cells. Luciferin solution (50 to 100 µL, Promega) was added to each well, and luciferase activity was measured with a Victor II luminometer (Perkin-Elmer). The percent inhibition of HCV RNA replication was calculated for each compound concentration and the EC$_{50}$ value was calculated using nonlinear regression curve fitting to the 4-parameter logistic equation and GraphPad Prism 4 software.

When tested by the above method, the compounds of this invention inhibit HCV polymerase 1A and/or 1B. The legend in the table below is as follows; A—EC$_{50}$≤0.01 µM; B—0.1 µM≥EC$_{50}$>0.01 µM; C—1 µM≥EC$_{50}$>0.1 µM; and D—EC$_{50}$>1 µM; ND—not determined.

TABLE EC$_{50}$

| compound | 1a | 1b | compound | 1a | 1b |
|---|---|---|---|---|---|
| 1 | C | A | 2 | ND | ND |
| 3 | C | B | 4 | ND | ND |
| 5 | D | C | 6 | C | C |
| 7 | D | C | | | |

All references (patent and non-patent) cited above are incorporated by reference into this patent application. The discussion of those references is intended merely to summarize the assertions made by their authors. No admission is made that any reference (or a portion of ay reference) is relevant prior art (or prior art at all). Applicants reserve the right to challenge the accuracy and pertinence of the cited references.

We claim:

1. A compound or salt thereof, wherein:

the compound corresponds in structure to formula (I):

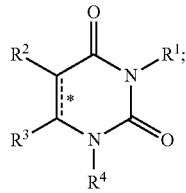

⸺*⸺ is selected from the group consisting of single carbon-carbon bond and double carbon-carbon bond;

$R^1$ is selected from the group consisting of hydrogen, methyl, and nitrogen-protecting group;

$R^2$ is selected from the group consisting of hydrogen, halo, hydroxy, methyl, cyclopropyl, and cyclobutyl;

$R^3$ is selected from the group consisting of hydrogen, halo, oxo, and methyl;

$R^4$ is selected from the group consisting of

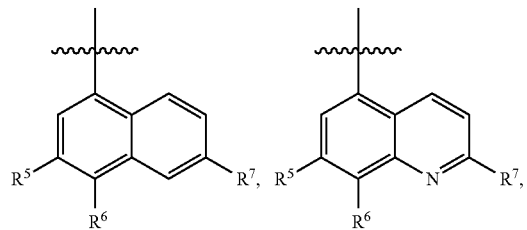

-continued

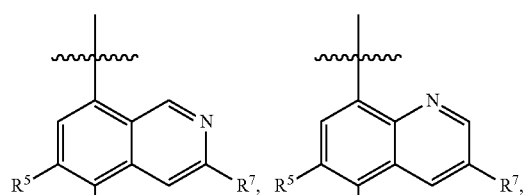

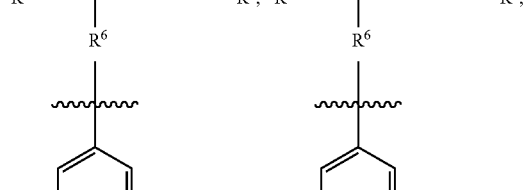

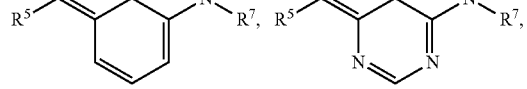

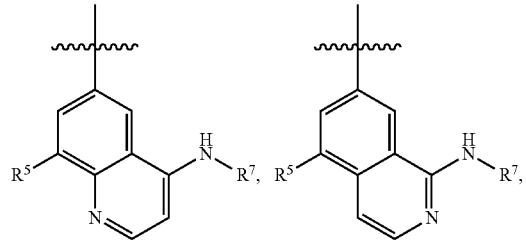

-continued

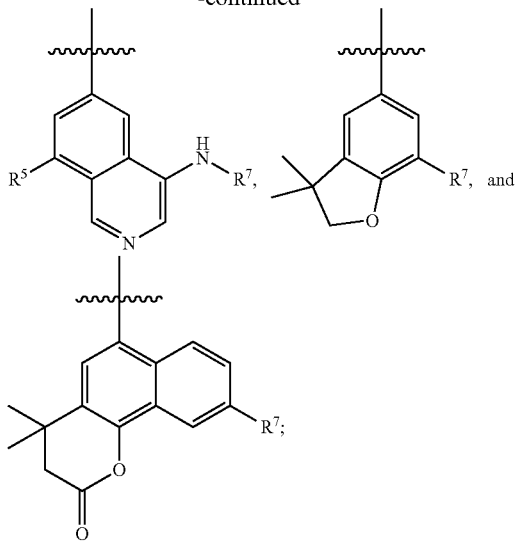

R⁵ is selected from the group consisting of halo, alkyl, alkenyl, alkynyl, nitro, cyano, azido, alkyloxy, alkenyloxy, alkynyloxy, amino, aminocarbonyl, aminosulfonyl, alkylsulfonyl, carbocyclyl, and heterocyclyl, wherein:
(a) the amino, aminocarbonyl, and aminosulfonyl optionally are substituted with:
  (1) one or two substituents independently selected from the group consisting of alkyl, alkenyl, alkynyl, and alkylsulfonyl, or
  (2) two substituents that, together with the amino nitrogen, form a single-ring heterocyclyl, and
(b) the alkyl, alkenyl, alkynyl, alkyloxy, alkenyloxy, alkynyloxy, and alkylsulfonyl, optionally are substituted with one or more substituents independently selected from the group consisting of halo, oxo, nitro, cyano, azido, hydroxy, amino, alkyloxy, trimethylsilyl, carbocyclyl, and heterocyclyl, wherein:
  the amino optionally is substituted with:
  (1) one or two substituents independently selected from the group consisting of alkyl, alkenyl, alkynyl, alkylcarbonyl, alkylsulfonyl, alkyloxycarbonyl, carbocyclyl, heterocyclyl, carbocyclylalkyl, and heterocyclylalkyl, or
  (2) two substituents that, together with the amino nitrogen, form a single-ring heterocyclyl, and
(c) the carbocyclyl and heterocyclyl optionally are substituted with up to three substituents independently selected from the group consisting of alkyl, alkenyl, alkynyl, halo, oxo, nitro, cyano, azido, hydroxy, amino, alkyloxy, trimethylsilyl, carbocyclyl, and heterocyclyl, wherein:
  the amino optionally is substituted with:
  (1) one or two substituents independently selected from the group consisting of alkyl, alkenyl, alkynyl, alkylcarbonyl, alkylsulfonyl, alkyloxycarbonyl, carbocyclyl, heterocyclyl, carbocyclylalkyl, and heterocyclylalkyl, or
  (2) two substituents that, together with the amino nitrogen, form a single-ring heterocyclyl;
R⁶ is selected from the group consisting of hydrogen, hydroxy, alkyl, alkenyl, alkynyl, alkyloxy, alkenyloxy, alkynyloxy, alkylsulfonyloxy, amino, carbocyclylsulfonyloxy, haloalkylsulfonyloxy, and halo;

R⁷ is selected from the group consisting of hydrogen, $C_5$-$C_6$-carbocyclyl, 5-6-membered heterocyclyl, fused 2-ring carbocyclyl, and fused 2-ring heterocyclyl, wherein:
  the $C_5$-$C_6$-carbocyclyl, 5-6-membered heterocyclyl, fused 2-ring carbocyclyl, and fused 2-ring heterocyclyl optionally are substituted with one or more substituents independently selected from the group consisting of $R^E$, $R^F$, $R^G$, $R^H$, $R^I$, $R^J$, and $R^K$;
each $R^E$ is independently selected from the group consisting of halo, nitro, hydroxy, oxo, carboxy, cyano, amino, imino, azido, and aldehydro, wherein:
  the amino optionally is substituted with one or two substituents independently selected from the group consisting of alkyl, alkenyl, and alkynyl;
each $R^F$ is independently selected from the group consisting of alkyl, alkenyl, and alkynyl, wherein:
  each such substituent optionally is substituted with one or more substituents independently selected from the group consisting of carboxy, hydroxy, halo, amino, imino, nitro, azido, oxo, aminosulfonyl, alkylsulfonyl, alkyloxycarbonyl, alkenyloxycarbonyl, alkynyloxycarbonyl, alkylcarbonyloxy, alkenylcarbonyloxy, alkynylcarbonyloxy, alkyloxy, alkenyloxy, alkynyloxy, carbocyclyl, heterocyclyl, cyano, and aminocarbonyl, wherein:
    the amino, imino, aminosulfonyl, aminocarbonyl, carbocyclyl, and heterocyclyl optionally are substituted with one or two substituents independently selected from the group consisting of alkyl, alkenyl, alkynyl, alkylsulfonyl, alkenylsulfonyl, alkynylsulfonyl, alkylsulfonylamino, hydroxy, and alkyloxy, wherein:
      the amino portion of the alkylsulfonylamino optionally is substituted with a substituent selected from the group consisting of alkyl, alkenyl, and alkynyl;
each $R^G$ is independently selected from the group consisting of carbocyclyl and heterocyclyl, wherein:
  each such substituent optionally is substituted with one or more substituents independently selected from the group consisting of alkyl, alkenyl, alkynyl, carboxy, hydroxy, halo, amino, nitro, azido, oxo, aminosulfonyl, alkyloxycarbonyl, alkenyloxycarbonyl, alkynyloxycarbonyl, alkylcarbonyloxy, alkenylcarbonyloxy, alkynylcarbonyloxy, alkyloxy, alkenyloxy, alkynyloxy, carbocyclyl, heterocyclyl, cyano, and aminocarbonyl, wherein:
    the amino, aminosulfonyl, and aminocarbonyl optionally are substituted with one or two substituents independently selected from the group consisting of alkyl, alkenyl, alkynyl, alkylsulfonyl, alkenylsulfonyl, and alkynylsulfonyl;
each $R^H$ is independently selected from the group consisting of alkyloxy, alkenyloxy, alkynyloxy, alkylsulfonyloxy, alkenylsulfonyloxy, and alkynylsulfonyloxy, wherein:
  each such substituent optionally is substituted with one or more substituents independently selected from the group consisting of carboxy, hydroxy, halo, amino, nitro, azido, oxo, aminosulfonyl, alkyloxycarbonyl, alkenyloxycarbonyl, alkynyloxycarbonyl, alkylcarbonyloxy, alkenylcarbonyloxy, alkynylcarbonyloxy, alkyloxy, alkenyloxy, alkynyloxy, carbocyclyl, heterocyclyl, cyano, and aminocarbonyl, wherein:
    the amino, aminosulfonyl, and aminocarbonyl optionally are substituted with one or two substituents independently selected from the group consisting of alkyl, alkenyl, alkynyl, alkylsulfonyl, alkenylsulfonyl, and alkynylsulfonyl;

each $R^I$ is independently selected from the group consisting of alkylcarbonyl, alkenylcarbonyl, alkynylcarbonyl, aminocarbonyl, alkyloxycarbonyl, carbocyclylcarbonyl, and heterocyclylcarbonyl, wherein:
(a) the alkylcarbonyl, alkenylcarbonyl, and alkynylcarbonyl optionally are substituted with one or more substituents independently selected from the group consisting of carboxy, hydroxy, halo, amino, nitro, azido, oxo, aminosulfonyl, alkyloxycarbonyl, alkenyloxycarbonyl, alkynyloxycarbonyl, alkylcarbonyloxy, alkenylcarbonyloxy, alkynylcarbonyloxy, alkyloxy, alkenyloxy, alkynyloxy, carbocyclyl, heterocyclyl, cyano, and aminocarbonyl, and
(b) the aminocarbonyl optionally is substituted with one or two substituents independently selected from the group consisting of alkyl, alkenyl, alkynyl, alkyloxyalkyl, carbocyclyl, heterocyclyl, alkylsulfonyl, and alkylsulfonylamino, wherein:
the carbocyclyl and heterocyclyl optionally are substituted with one or two substituents independently selected from the group consisting of halo, alkyl, and oxo;

each $R^J$ is independently selected from the group consisting of carbocyclylsulfonylamino, heterocyclylsulfonylamino, alkylcarbonylamino, alkenylcarbonylamino, alkynylcarbonylamino, alkyloxycarbonylamino, alkenyloxycarbonylamino, alkynyloxycarbonylamino, alkylsulfonylamino, alkenylsulfonylamino, alkynylsulfonylamino, aminocarbonylamino, alkyloxycarbonylaminoimino, alkylsulfonylaminoimino, alkenylsulfonylaminoimino, and alkynylsulfonylaminoimino, wherein:
(a) the amino portion of such substituents optionally is substituted with a substituent independently selected from the group consisting of carbocyclylalkyl, heterocyclylalkyl, alkylcarbonyloxy, aminocarbonylalkyl, alkyl, alkenyl, alkynyl, alkylcarbonyl, alkenylcarbonyl, alkynylcarbonyl, alkyloxycarbonyl, alkyloxyalkyloxycarbonyl, alkylcarbonyloxyalkyl, and alkylsulfonyl, wherein:
(1) the carbocyclyl portion of the carbocyclylalkyl and the heterocyclyl portion of the heterocyclylalkyl optionally are substituted with one or more substituents independently selected from the group consisting of alkyl, alkenyl, alkynyl, carboxy, hydroxy, alkyloxy, alkenyloxy, alkynyloxy, halo, nitro, cyano, azido, oxo, and amino, and
(2) the amino portion of the aminocarbonylalkyl optionally is substituted with one or two substituents independently selected from the group consisting of alkyl, alkenyl, and alkynyl,
(b) the alkyl, alkenyl, and alkynyl portion of such substituents optionally is substituted with one or more substituents independently selected from the group consisting of carboxy, halo, oxo, amino, alkyloxycarbonyl, alkylcarbonyloxy, hydroxy, alkyloxy, carbocyclyl, heterocyclyl, and cyano, wherein:
the amino optionally is substituted with one or two substituents independently selected from the group consisting of alkyl, alkenyl, alkynyl, alkyloxy, alkenyloxy, and alkynyloxy, wherein:
the alkyl optionally is substituted with one or more hydroxy;

(c) the carbocyclyl and heterocyclyl portions of such substituents optionally are substituted with one or more substituents independently selected from the group consisting of alkyl, alkenyl, alkynyl, carboxy, hydroxy, alkyloxy, alkenyloxy, alkynyloxy, halo, nitro, cyano, azido, and amino, wherein:
the amino optionally is substituted with one or two substituents independently selected from the group consisting of alkyl, alkenyl, and alkynyl; and each $R^K$ is independently selected from the group consisting of aminosulfonyl, alkylsulfonyl, alkenylsulfonyl, and alkynylsulfonyl, wherein:
(a) the alkylsulfonyl, alkenylsulfonyl, and alkynylsulfonyl optionally are substituted with one or more substituents independently selected from the group consisting of carboxy, hydroxy, halo, amino, nitro, azido, oxo, aminosulfonyl, alkyloxycarbonyl, alkenyloxycarbonyl, alkynyloxycarbonyl, alkylcarbonyloxy, alkenylcarbonyloxy, alkynylcarbonyloxy, alkyloxy, alkenyloxy, alkynyloxy, carbocyclyl, heterocyclyl, cyano, and aminocarbonyl, wherein:
the amino, aminosulfonyl, and aminocarbonyl optionally are substituted with one or two substituents independently selected from the group consisting of alkyl, alkenyl, and alkynyl; and
(b) the aminosulfonyl optionally is substituted with one or two substituents independently selected from the group consisting of alkyl, alkenyl, and alkynyl.

2. The compound or salt of claim 1, wherein the compound corresponds in structure to formula I-2:

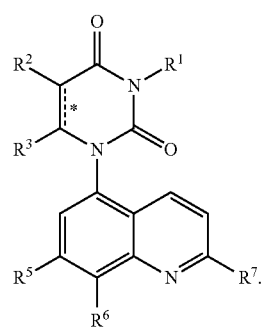

(I-2)

3. The compound or salt of claim 1, wherein the compound corresponds in structure to formula I-6:

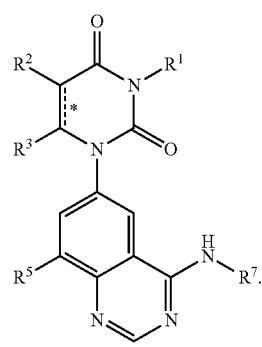

(I-6)

4. The compound or salt of claim 1, wherein the compound corresponds in structure to formula I-10:

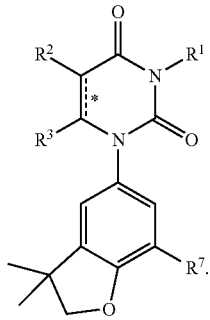

(I-10)

5. The compound or salt of claim 1, wherein the compound corresponds in structure to formula I-11:

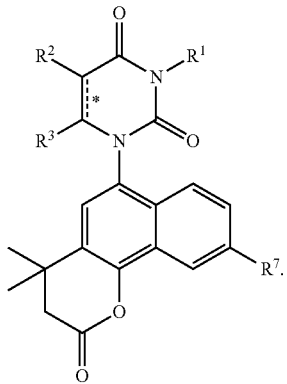

(I-11)

6. The compound or salt of claim 1, wherein ═*═ is a single carbon-carbon bond.

7. The compound or salt of claim 1, wherein ═*═ is a double carbon-carbon bond.

8. The compound or salt of claim 1, wherein $R^1$ is selected from the group consisting of hydrogen and methyl.

9. The compound or salt of claim 1, wherein $R^2$ is selected from the group consisting of hydrogen, methyl, hydroxy, and halo.

10. The compound or salt of claims 1, wherein $R^3$ is selected from the group consisting of hydrogen, halo, and oxo.

11. The compound or salt of claim 1, wherein $R^5$ is selected from the group consisting of halo, alkyl, and alkyloxy.

12. The compound or salt of claim 1, wherein $R^5$ is tert-butyl.

13. The compound or salt of claim 1, wherein $R^5$ is selected from the group consisting of $C_1$-$C_4$-alkyl and 5-6-membered heterocyclyl, wherein:
   (a) the $C_1$-$C_4$-alkyl optionally is substituted with one or more independently selected halo substituents; and
   (b) the 5-6-membered heterocyclyl optionally is substituted with one or more independently selected $C_1$-$C_4$-alkyl substituents.

14. The compound or salt of claim 1, wherein $R^5$ is selected from the group consisting of tert-butyl, trifluoromethyl, and 5-6-membered heterocyclyl optionally substituted with methyl.

15. The compound or salt of claim 1, wherein $R^6$ is selected from the group consisting of hydrogen, hydroxy, alkenyl, alkyl, alkyloxy, amino, and halo.

16. The compound or salt of claim 1, wherein $R^6$ is selected from the group consisting of methyl, ethenyl, ethyl, hydroxy, methoxy, amino, and iodo.

17. The compound or salt of claim 1, wherein $R^7$ is hydrogen or $C_5$-$C_6$-carbocyclyl substituted with a substituent selected from the group consisting of $R^E$, $R^F$, $R^G$, $R^H$, $R^I$, $R^J$, and $R^K$.

18. The compound or salt of claim 1, wherein $R^7$ is 5-6-membered heterocyclyl substituted with a substituent selected from the group consisting of $R^F$ and $R^J$.

19. The compound or salt of claim 1, wherein $R^F$ is alkylsulfonylamino.

20. The compound or salt of claim 1, wherein the compound is selected from the group consisting of

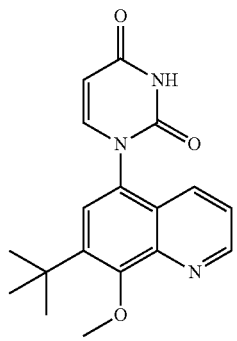

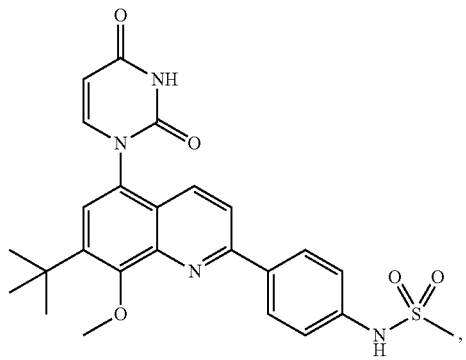

,

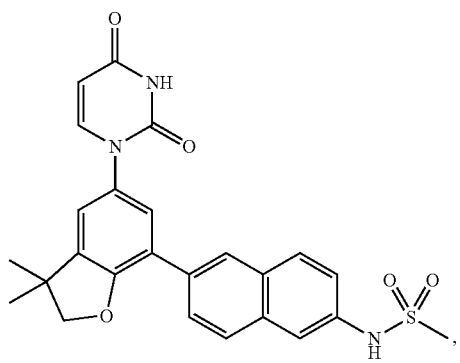

,

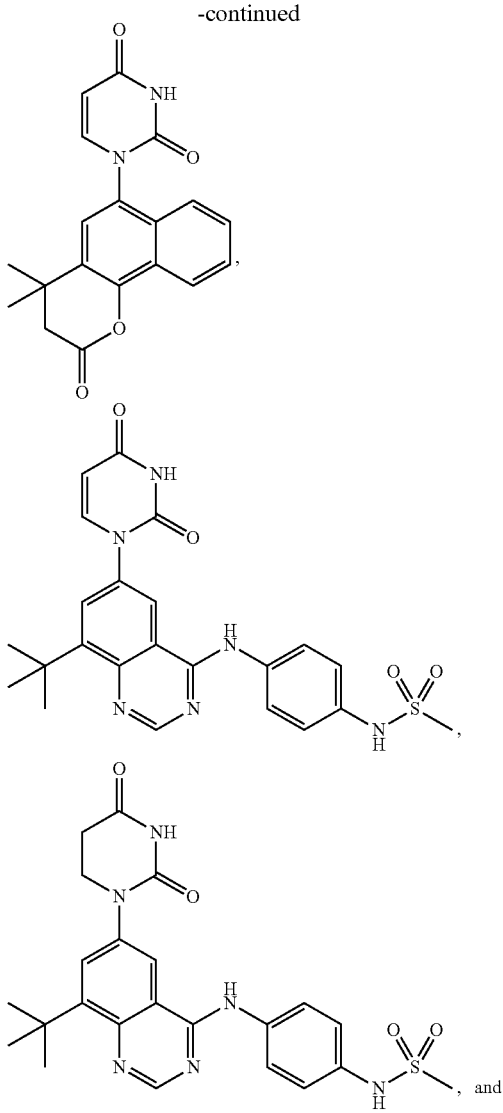

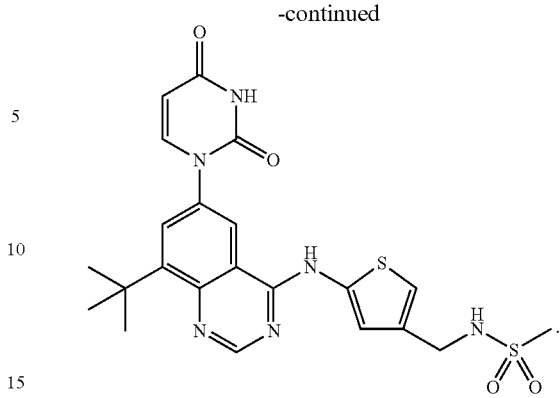

21. A pharmaceutical composition comprising one or more compounds and/or salts recited in claim 1 and one or more excipients.

22. The pharmaceutical composition of claim 21, wherein the pharmaceutical composition further comprises one or more additional therapeutic agents.

23. A method for inhibiting replication of a hepatitis C ribonucleic acid (RNA) virus, wherein the method comprises exposing the virus to one or more compounds and/or salts recited in claim 1.

24. A method for treating hepatitis C in a mammal in need of such treatment, wherein the method comprises administering to the mammal one or more compounds and/or salts recited in claim 1.

25. The method of claim 24, wherein the mammal is human.

26. The method of claim 24, wherein the method further comprises administering to the mammal one or more additional therapeutic agents.

27. The method of claim 24, wherein one or more additional therapeutic agents are selected from the group consisting of interferon agent, ribavirin, HCV inhibitor, and HIV inhibitor.

* * * * *